(12) United States Patent
Kawakami et al.

(10) Patent No.: US 8,546,320 B2
(45) Date of Patent: Oct. 1, 2013

(54) HSP90-TARGETED ANTI-CANCER CHIMERIC PEPTIDE

(75) Inventors: Koji Kawakami, Kyoto (JP); Masayuki Kohno, Kyoto (JP); Tomohisa Horibe, Kyoto (JP)

(73) Assignee: Kyoto University, Kyoto-shi, Kyoto (JP)

( * ) Notice: Subject to any disclaimer, the term of this patent is extended or adjusted under 35 U.S.C. 154(b) by 89 days.

(21) Appl. No.: 13/129,350

(22) PCT Filed: Nov. 13, 2009

(86) PCT No.: PCT/JP2009/069405
§ 371 (c)(1),
(2), (4) Date: Sep. 9, 2011

(87) PCT Pub. No.: WO2010/055929
PCT Pub. Date: May 20, 2010

(65) Prior Publication Data
US 2012/0003299 A1    Jan. 5, 2012

(30) Foreign Application Priority Data
Nov. 14, 2008    (JP) .................................. 2008-292849

(51) Int. Cl.
*C07K 14/00*    (2006.01)

(52) U.S. Cl.
USPC ............................................ 514/1; 530/300

(58) Field of Classification Search
USPC ............................................. 514/1; 530/300
See application file for complete search history.

(56) References Cited

U.S. PATENT DOCUMENTS

| | | | |
|---|---|---|---|
| 2003/0138848 A1 | 7/2003 | Moarefi et al. ................ | 435/7.1 |
| 2007/0031815 A1 | 2/2007 | Jenkins et al. ................. | 435/4 |
| 2010/0209429 A1* | 8/2010 | Erlich et al. ................... | 424/139.1 |

FOREIGN PATENT DOCUMENTS

| | | |
|---|---|---|
| JP | 2003-523313 A | 8/2003 |
| WO | WO 2009/039188 A1 | 3/2009 |
| WO | WO 00/53169 A2 | 9/2009 |

OTHER PUBLICATIONS

Wassenberg et al. 1999; Receptor mediated and fluid phase pathways for internalization of the ER HSP90 chaperone GRP94 in murine macrophages. Journal of Cell Science. 112: 2167-2175.*

Deshayes et al. 2005; Cell-penetrating peptides: tools for intracellular delivery of therapeutics. Cellular and Molecular Life Sciences. 62: 1839-1849.*

Bonfanti et al., "p21$^{WAF1}$-derived Peptides Linked to an Internalization Peptide Inhibit Human Cancer Cell Growth," *Cancer Research* 57(8): 1442-1446, Apr. 15, 1997.

Cortajarena et al., "Designed TPR Modules as Novel Anticancer Agents," *ACS Chemical Biology* 3(3): 161-166, Mar. 20, 2008.

Flom et al., "Definition of the minimal fragments of Sti1 required for dimerization, interaction with Hsp70 and Hsp90 and in vivo functions," *Biochem J* 404(1): 159-167, 2007.

Honoré et al., "Molecular Cloning and Expression of a Transformation-sensitive Human Protein Containing the TPR Motif and Sharing Identity to the Stress-inducible Yeast Protein *STI1*," *J Biol Chem* 267(12): 8485-8491, Apr. 25, 1992.

Scheufler et al., "Structure of TPR Domain-Peptide Complexes: Critical Elements in the Assembly of the Hsp70-Hsp90 Multichaperone Machine," *Cell 101*(2): 199-210, Apr. 14, 2000.

* cited by examiner

*Primary Examiner* — Karen Cochrane Carlson
(74) *Attorney, Agent, or Firm* — Seed IP Law Group PLLC

(57) ABSTRACT

Disclosed is a substance which is not accumulated stably in cells, does not cause the dysfunction of normal cells, and so on, and therefore can be used as an anti-cancer agent or in a DDS without having any adverse side effects. It is found that Hsp90 alone cannot exhibit its function as a chaperone in assisting the refolding of a protein such as survivin, but can exhibit this function when Hop (which is one of the partner proteins of Hsp90) binds to Hsp90. Thus, specifically disclosed herein is a chimeric peptide comprising of an Hsp90 TPR domain binding peptide and a cell-penetrating peptide.

12 Claims, 21 Drawing Sheets

Figure 4
(A)
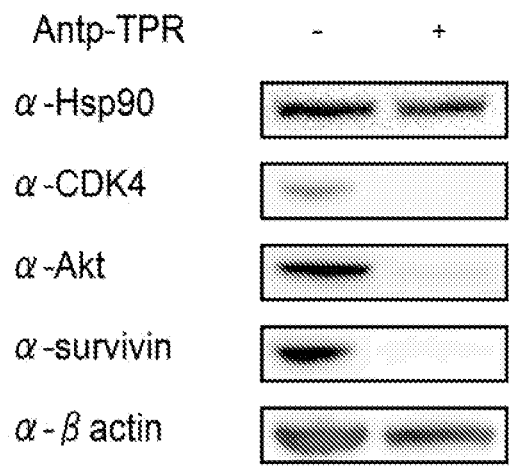
(B)
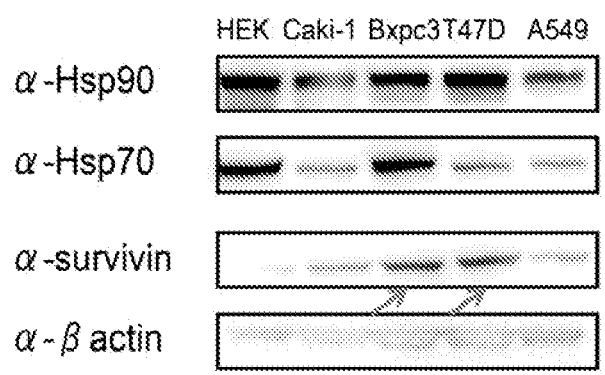

Figure 5

Anti-cancer activity
(relative % to wild-type peptide)

| Antp-wild | Antp-K1R | Antp-K1A | Antp-A2G | Antp-Y3L | Antp-A4G | Antp-R5K | Antp-I6R | Antp-G7A | Antp-N8Q | Antp-S9Y | Antp-Y10S | Antp-F11Y | Antp-K12R |
|---|---|---|---|---|---|---|---|---|---|---|---|---|---|
| 100 | 35.81 | 20.29 | 100.67 | 52.87 | 108.36 | 6.58 | 1.95 | 96.23 | 98.57 | 106.80 | 74.56 | 110.49 | 90.20 |

Sequence of Antp-TPR peptide and site of mutation

| | |
|---|---|
| Antp-TPR wild | Antp-KAYARIGNSYFK (SEQ ID No. 9) |
| Antp-TPR K1R | Antp-RAYARIGNSYFK (SEQ ID No. 10) |
| Antp-TPR K1A | Antp-AAYARIGNSYFK (SEQ ID No. 11) |
| Antp-TPR A2G | Antp-KGYARIGNSYFK (SEQ ID No. 12) |
| Antp-TPR Y3L | Antp-KALARIGNSYFK (SEQ ID No. 13) |
| Antp-TPR A4G | Antp-KAYGRIGNSYFK (SEQ ID No. 14) |
| Antp-TPR R5K | Antp-KAYAKIGNSYFK (SEQ ID No. 15) |
| Antp-TPR I6R | Antp-KAYARRGNSYFK (SEQ ID No. 16) |
| Antp-TPR G7A | Antp-KAYARIANSYFK (SEQ ID No. 17) |
| Antp-TPR N8Q | Antp-KAYARIGQSYFK (SEQ ID No. 18) |
| Antp-TPR S9Y | Antp-KAYARIGNYYFK (SEQ ID No. 19) |
| Antp-TPR Y10S | Antp-KAYARIGNSSFK (SEQ ID No. 20) |
| Antp-TPR F11Y | Antp-KAYARIGNSYYK (SEQ ID No. 21) |
| Antp-TPR K12R | Antp-KAYARIGNSYFR (SEQ ID No. 22) |

Figure 8A

Anti-cancer activity
(relative % to wild-type peptide)

| Antp -wild | Antp R1K -TPR | Antp Q2N -TPR | Antp I3L -TPR | Antp K4R -TPR | Antp I5L -TPR | Antp W6Y -TPR | Antp F7Y -TPR | Antp Q8N -TPR | Antp N9Q -TPR | Antp R10K -TPR | Antp R11K -TPR | Antp M12C -TPR | Antp K13R -TPR | Antp W14Y -TPR | Antp K15R -TPR | Antp K16R -TPR |
|---|---|---|---|---|---|---|---|---|---|---|---|---|---|---|---|---|
| 100 | 64.10 | 88.97 | 69.12 | 109.86 | 73.75 | 32.99 | 29.86 | 109.65 | 110.59 | 110.30 | 104.39 | 102.68 | 108.64 | 83.36 | 110.21 | 110.26 |

Sequence of Antp-TPR peptide and site of mutation

| | |
|---|---|
| Wild type (Antp-wild) | RQIKIWFQNRRMKWKK-KAYARIGNSYFK (SEQ ID No. 9) |
| AnR1K | KQIKIWFQNRRMKWKK-TPR peptide (SEQ ID No. 23) |
| AnQ2N | RNIKIWFQNRRMKWKK-TPR peptide (SEQ ID No. 24) |
| AnI3L | RQLKIWFQNRRMKWKK-TPR peptide (SEQ ID No. 25) |
| AnK4R | RQIRIWFQNRRMKWKK-TPR peptide (SEQ ID No. 26) |
| AnI5L | RQIKLWFQNRRMKWKK-TPR peptide (SEQ ID No. 27) |
| AnW6Y | RQIKIYFQNRRMKWKK-TPR peptide (SEQ ID No. 28) |
| AnF7Y | RQIKIWYQNRRMKWKK-TPR peptide (SEQ ID No. 29) |
| AnQ8N | RQIKIWFNNRRMKWKK-TPR peptide (SEQ ID No. 30) |
| AnN9Q | RQIKIWFQQRRMKWKK-TPR peptide (SEQ ID No. 31) |
| AnR10K | RQIKIWFQNKRMKWKK-TPR peptide (SEQ ID No. 32) |
| AnR11K | RQIKIWFQNRKMKWKK-TPR peptide (SEQ ID No. 33) |
| AnM12C | RQIKIWFQNRRCKWKK-TPR peptide (SEQ ID No. 34) |
| AnK13R | RQIKIWFQNRRMRWKK-TPR peptide (SEQ ID No. 35) |
| AnW14Y | RQIKIWFQNRRMKYKK-TPR peptide (SEQ ID No. 36) |
| AnK15R | RQIKIWFQNRRMKWRK-TPR peptide (SEQ ID No. 37) |
| AnK16R | RQIKIWFQNRRMKWKR-TPR peptide (SEQ ID No. 38) |

SEQUENCE LISTING

```
<160> NUMBER OF SEQ ID NOS: 72

<210> SEQ ID NO 1
<211> LENGTH: 12
<212> TYPE: PRT
<213> ORGANISM: Artificial Sequence
<220> FEATURE:
<223> OTHER INFORMATION: Hsp90 TRP domain binding peptide
<220> FEATURE:
<221> NAME/KEY: misc_feature
<222> LOCATION: (1)..(1)
<223> OTHER INFORMATION: Xaa is an amino acid K or an amino acid similar
      thereto
<220> FEATURE:
<221> NAME/KEY: misc_feature
<222> LOCATION: (2)..(2)
<223> OTHER INFORMATION: Xaa is an amino acid A or an amino acid similar
      thereto
<220> FEATURE:
<221> NAME/KEY: misc_feature
<222> LOCATION: (3)..(3)
<223> OTHER INFORMATION: Xaa is an amino acid Y or an amino acid similar
      thereto
<220> FEATURE:
<221> NAME/KEY: misc_feature
<222> LOCATION: (4)..(4)
<223> OTHER INFORMATION: Xaa is an amino acid A or an amino acid similar
      thereto
<220> FEATURE:
<221> NAME/KEY: misc_feature
<222> LOCATION: (5)..(5)
<223> OTHER INFORMATION: Xaa is an amino acid R or an amino acid similar
      thereto
<220> FEATURE:
<221> NAME/KEY: misc_feature
<222> LOCATION: (6)..(6)
<223> OTHER INFORMATION: Xaa is an amino acid I or an amino acid similar
      thereto
<220> FEATURE:
<221> NAME/KEY: misc_feature
<222> LOCATION: (7)..(7)
<223> OTHER INFORMATION: Xaa is an amino acid G or an amino acid similar
```

```
                            -continued
      thereto
<220> FEATURE:
<221> NAME/KEY: misc_feature
<222> LOCATION: (8)..(8)
<223> OTHER INFORMATION: Xaa is an amino acid N or an amino acid similar
      thereto
<220> FEATURE:
<221> NAME/KEY: misc_feature
<222> LOCATION: (9)..(9)
<223> OTHER INFORMATION: Xaa is an amino acid S or an amino acid similar
      thereto
<220> FEATURE:
<221> NAME/KEY: misc_feature
<222> LOCATION: (10)..(10)
<223> OTHER INFORMATION: Xaa is an amino acid Y or an amino acid similar
      thereto
<220> FEATURE:
<221> NAME/KEY: misc_feature
<222> LOCATION: (11)..(11)
<223> OTHER INFORMATION: Xaa is an amino acid F or an amino acid similar
      thereto
<220> FEATURE:
<221> NAME/KEY: misc_feature
<222> LOCATION: (12)..(12)
<223> OTHER INFORMATION: Xaa is an amino acid K or an amino acid similar
      thereto

<400> SEQUENCE: 1

Xaa Xaa Xaa Xaa Xaa Xaa Xaa Xaa Xaa Xaa Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: TRP domain binding peptide
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa corresponds to Z1 as defined in the
      specification, which can be Y/H
<220> FEATURE:
<221> NAME/KEY: misc_feature
<222> LOCATION: (11)..(11)
<223> OTHER INFORMATION: Xaa corresponds to Z2 as defined in the
      specification, which can be F/E/M/L/S
<220> FEATURE:
<221> NAME/KEY: misc_feature
<222> LOCATION: (12)..(12)
<223> OTHER INFORMATION: Xaa corresponds to Z3 as defined in the
      specification, which can be K/A/L/Q/S

<400> SEQUENCE: 2

Lys Ala Tyr Ala Arg Xaa Xaa Xaa Xaa Xaa Xaa Xaa
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Hsp90 TRP domain binding peptide

<400> SEQUENCE: 3

Lys Ala Tyr Ala Arg
1               5

<210> SEQ ID NO 4
<211> LENGTH: 12
```

```
<212> TYPE: PRT
<213> ORGANISM: Artificial Sequence
<220> FEATURE:
<223> OTHER INFORMATION: Hsp90 TRP domain binding peptide

<400> SEQUENCE: 4

Lys Ala Tyr Ala Arg Ile Gly Asn Ser Tyr Phe Lys
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Antp sequence

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: TAT sequence

<400> SEQUENCE: 6

Tyr Gly Arg Lys Lys Arg Arg Gln Arg Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: R11 sequence

<400> SEQUENCE: 7

Arg Arg Arg Arg Arg Arg Arg Arg Arg Arg Arg
1               5                   10

<210> SEQ ID NO 8
<211> LENGTH: 16
<212> TYPE: PRT
<213> ORGANISM: Artificial Sequence
<220> FEATURE:
<223> OTHER INFORMATION: variant sequence of cell permeable peptide
<220> FEATURE:
<221> NAME/KEY: misc_feature
<222> LOCATION: (1)..(1)
<223> OTHER INFORMATION: Xaa is an amino acid R or an amino acid similar
      thereto
<220> FEATURE:
<221> NAME/KEY: misc_feature
<222> LOCATION: (2)..(2)
<223> OTHER INFORMATION: Xaa is an amino acid Q or an amino acid similar
      thereto
<220> FEATURE:
<221> NAME/KEY: misc_feature
<222> LOCATION: (3)..(3)
<223> OTHER INFORMATION: Xaa is an amino acid I or an amino acid similar
      thereto
<220> FEATURE:
<221> NAME/KEY: misc_feature
<222> LOCATION: (4)..(4)
<223> OTHER INFORMATION: Xaa is an amino acid K or an amino acid similar
      thereto
<220> FEATURE:
<221> NAME/KEY: misc_feature
<222> LOCATION: (5)..(5)
<223> OTHER INFORMATION: Xaa is an amino acid I or an amino acid similar
```

```
                                  -continued
          thereto
<220> FEATURE:
<221> NAME/KEY: misc_feature
<222> LOCATION: (6)..(6)
<223> OTHER INFORMATION: Xaa is an amino acid Q or an amino acid similar
      thereto
<220> FEATURE:
<221> NAME/KEY: misc_feature
<222> LOCATION: (7)..(7)
<223> OTHER INFORMATION: Xaa is an amino acid F or an amino acid similar
      thereto
<220> FEATURE:
<221> NAME/KEY: misc_feature
<222> LOCATION: (8)..(8)
<223> OTHER INFORMATION: Xaa is an amino acid Q or an amino acid similar
      thereto
<220> FEATURE:
<221> NAME/KEY: misc_feature
<222> LOCATION: (9)..(9)
<223> OTHER INFORMATION: Xaa is an amino acid N or an amino acid similar
      thereto
<220> FEATURE:
<221> NAME/KEY: misc_feature
<222> LOCATION: (10)..(10)
<223> OTHER INFORMATION: Xaa is an amino acid R or an amino acid similar
      thereto
<220> FEATURE:
<221> NAME/KEY: misc_feature
<222> LOCATION: (11)..(11)
<223> OTHER INFORMATION: Xaa is an amino acid R or an amino acid similar
      thereto
<220> FEATURE:
<221> NAME/KEY: misc_feature
<222> LOCATION: (12)..(12)
<223> OTHER INFORMATION: Xaa is an amino acid M or an amino acid similar
      thereto
<220> FEATURE:
<221> NAME/KEY: misc_feature
<222> LOCATION: (13)..(13)
<223> OTHER INFORMATION: Xaa is an amino acid K or an amino acid similar
      thereto
<220> FEATURE:
<221> NAME/KEY: misc_feature
<222> LOCATION: (14)..(14)
<223> OTHER INFORMATION: Xaa is an amino acid K or an amino acid similar
      thereto
<220> FEATURE:
<221> NAME/KEY: misc_feature
<222> LOCATION: (15)..(15)
<223> OTHER INFORMATION: Xaa is an amino acid K or an amino acid similar
      thereto
<220> FEATURE:
<221> NAME/KEY: misc_feature
<222> LOCATION: (16)..(16)
<223> OTHER INFORMATION: Xaa is an amino acid K or an amino acid similar
      thereto

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

<210> SEQ ID NO 9
<211> LENGTH: 28
<212> TYPE: PRT
<213> ORGANISM: Artificial Sequence
<220> FEATURE:
<223> OTHER INFORMATION: chimeric peptide

<400> SEQUENCE: 9

Arg Gln Ile Lys Ile Trp Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 10
```

```
<211> LENGTH: 28
<212> TYPE: PRT
<213> ORGANISM: Artificial Sequence
<220> FEATURE:
<223> OTHER INFORMATION: chimeric peptide

<400> SEQUENCE: 10

Arg Gln Ile Lys Ile Trp Phe Gln Asn Arg Arg Met Lys Trp Lys Lys
1               5                   10                  15

Arg Ala Tyr Ala Arg Ile Gly Asn Ser Tyr Phe Lys
            20                  25

<210> SEQ ID NO 11
<211> LENGTH: 28
<212> TYPE: PRT
<213> ORGANISM: Artificial Sequence
<220> FEATURE:
<223> OTHER INFORMATION: chimeric peptide

<400> SEQUENCE: 11

Arg Gln Ile Lys Ile Trp Phe Gln Asn Arg Arg Met Lys Trp Lys Lys
1               5                   10                  15

Ala Ala Tyr Ala Arg Ile Gly Asn Ser Tyr Phe Lys
            20                  25

<210> SEQ ID NO 12
<211> LENGTH: 28
<212> TYPE: PRT
<213> ORGANISM: Artificial Sequence
<220> FEATURE:
<223> OTHER INFORMATION: chimeric peptide

<400> SEQUENCE: 12

Arg Gln Ile Lys Ile Trp Phe Gln Asn Arg Arg Met Lys Trp Lys Lys
1               5                   10                  15

Lys Gly Tyr Ala Arg Ile Gly Asn Ser Tyr Phe Lys
            20                  25

<210> SEQ ID NO 13
<211> LENGTH: 28
<212> TYPE: PRT
<213> ORGANISM: Artificial Sequence
<220> FEATURE:
<223> OTHER INFORMATION: chimeric peptide

<400> SEQUENCE: 13

Arg Gln Ile Lys Ile Trp Phe Gln Asn Arg Arg Met Lys Trp Lys Lys
1               5                   10                  15

Lys Ala Leu Ala Arg Ile Gly Asn Ser Tyr Phe Lys
            20                  25

<210> SEQ ID NO 14
<211> LENGTH: 28
<212> TYPE: PRT
<213> ORGANISM: Artificial Sequence
<220> FEATURE:
<223> OTHER INFORMATION: chimeric peptide

<400> SEQUENCE: 14

Arg Gln Ile Lys Ile Trp Phe Gln Asn Arg Arg Met Lys Trp Lys Lys
1               5                   10                  15

Lys Ala Tyr Gly Arg Ile Gly Asn Ser Tyr Phe Lys
            20                  25

<210> SEQ ID NO 15
```

```
<211> LENGTH: 28
<212> TYPE: PRT
<213> ORGANISM: Artificial Sequence
<220> FEATURE:
<223> OTHER INFORMATION: chimeric peptide

<400> SEQUENCE: 15

Arg Gln Ile Lys Ile Trp Phe Gln Asn Arg Arg Met Lys Trp Lys Lys
1               5                   10                  15

Lys Ala Tyr Ala Lys Ile Gly Asn Ser Tyr Phe Lys
            20                  25

<210> SEQ ID NO 16
<211> LENGTH: 28
<212> TYPE: PRT
<213> ORGANISM: Artificial Sequence
<220> FEATURE:
<223> OTHER INFORMATION: chimeric peptide

<400> SEQUENCE: 16

Arg Gln Ile Lys Ile Trp Phe Gln Asn Arg Arg Met Lys Trp Lys Lys
1               5                   10                  15

Lys Ala Tyr Ala Arg Arg Gly Asn Ser Tyr Phe Lys
            20                  25

<210> SEQ ID NO 17
<211> LENGTH: 28
<212> TYPE: PRT
<213> ORGANISM: Artificial Sequence
<220> FEATURE:
<223> OTHER INFORMATION: chimeric peptide

<400> SEQUENCE: 17

Arg Gln Ile Lys Ile Trp Phe Gln Asn Arg Arg Met Lys Trp Lys Lys
1               5                   10                  15

Lys Ala Tyr Ala Arg Ile Ala Asn Ser Tyr Phe Lys
            20                  25

<210> SEQ ID NO 18
<211> LENGTH: 28
<212> TYPE: PRT
<213> ORGANISM: Artificial Sequence
<220> FEATURE:
<223> OTHER INFORMATION: chimeric peptide

<400> SEQUENCE: 18

Arg Gln Ile Lys Ile Trp Phe Gln Asn Arg Arg Met Lys Trp Lys Lys
1               5                   10                  15

Lys Ala Tyr Ala Arg Ile Gly Gln Ser Tyr Phe Lys
            20                  25

<210> SEQ ID NO 19
<211> LENGTH: 28
<212> TYPE: PRT
<213> ORGANISM: Artificial Sequence
<220> FEATURE:
<223> OTHER INFORMATION: chimeric peptide

<400> SEQUENCE: 19

Arg Gln Ile Lys Ile Trp Phe Gln Asn Arg Arg Met Lys Trp Lys Lys
1               5                   10                  15

Lys Ala Tyr Ala Arg Ile Gly Asn Tyr Tyr Phe Lys
            20                  25

<210> SEQ ID NO 20
```

```
<211> LENGTH: 28
<212> TYPE: PRT
<213> ORGANISM: Artificial Sequence
<220> FEATURE:
<223> OTHER INFORMATION: chimeric peptide

<400> SEQUENCE: 20

Arg Gln Ile Lys Ile Trp Phe Gln Asn Arg Arg Met Lys Trp Lys Lys
1               5                   10                  15

Lys Ala Tyr Ala Arg Ile Gly Asn Ser Ser Phe Lys
            20                  25

<210> SEQ ID NO 21
<211> LENGTH: 28
<212> TYPE: PRT
<213> ORGANISM: Artificial Sequence
<220> FEATURE:
<223> OTHER INFORMATION: chimeric peptide

<400> SEQUENCE: 21

Arg Gln Ile Lys Ile Trp Phe Gln Asn Arg Arg Met Lys Trp Lys Lys
1               5                   10                  15

Lys Ala Tyr Ala Arg Ile Gly Asn Ser Tyr Tyr Lys
            20                  25

<210> SEQ ID NO 22
<211> LENGTH: 28
<212> TYPE: PRT
<213> ORGANISM: Artificial Sequence
<220> FEATURE:
<223> OTHER INFORMATION: chimeric peptide

<400> SEQUENCE: 22

Arg Gln Ile Lys Ile Trp Phe Gln Asn Arg Arg Met Lys Trp Lys Lys
1               5                   10                  15

Lys Ala Tyr Ala Arg Ile Gly Asn Ser Tyr Phe Arg
            20                  25

<210> SEQ ID NO 23
<211> LENGTH: 28
<212> TYPE: PRT
<213> ORGANISM: Artificial Sequence
<220> FEATURE:
<223> OTHER INFORMATION: chimeric peptide

<400> SEQUENCE: 23

Lys Gln Ile Lys Ile Trp Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 24
<211> LENGTH: 28
<212> TYPE: PRT
<213> ORGANISM: Artificial Sequence
<220> FEATURE:
<223> OTHER INFORMATION: chimeric peptide

<400> SEQUENCE: 24

Arg Asn Ile Lys Ile Trp Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 25
```

```
<211> LENGTH: 28
<212> TYPE: PRT
<213> ORGANISM: Artificial Sequence
<220> FEATURE:
<223> OTHER INFORMATION: chimeric peptide

<400> SEQUENCE: 25

Arg Gln Leu Lys Ile Trp Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 26
<211> LENGTH: 28
<212> TYPE: PRT
<213> ORGANISM: Artificial Sequence
<220> FEATURE:
<223> OTHER INFORMATION: chimeric peptide

<400> SEQUENCE: 26

Arg Gln Ile Arg Ile Trp Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 27
<211> LENGTH: 28
<212> TYPE: PRT
<213> ORGANISM: Artificial Sequence
<220> FEATURE:
<223> OTHER INFORMATION: chimeric peptide

<400> SEQUENCE: 27

Arg Gln Ile Lys Leu Trp Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 28
<211> LENGTH: 28
<212> TYPE: PRT
<213> ORGANISM: Artificial Sequence
<220> FEATURE:
<223> OTHER INFORMATION: chimeric peptide

<400> SEQUENCE: 28

Arg Gln Ile Lys Ile Tyr Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 29
<211> LENGTH: 28
<212> TYPE: PRT
<213> ORGANISM: Artificial Sequence
<220> FEATURE:
<223> OTHER INFORMATION: chimeric peptide

<400> SEQUENCE: 29

Arg Gln Ile Lys Ile Trp Tyr Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 30
```

```
<211> LENGTH: 28
<212> TYPE: PRT
<213> ORGANISM: Artificial Sequence
<220> FEATURE:
<223> OTHER INFORMATION: chimeric peptide

<400> SEQUENCE: 30

Arg Gln Ile Lys Ile Trp Phe Asn Asn Arg Met Lys Trp Lys Lys
1               5                   10                  15

Lys Ala Tyr Ala Arg Ile Gly Asn Ser Tyr Phe Lys
            20                  25

<210> SEQ ID NO 31
<211> LENGTH: 28
<212> TYPE: PRT
<213> ORGANISM: Artificial Sequence
<220> FEATURE:
<223> OTHER INFORMATION: chimeric peptide

<400> SEQUENCE: 31

Arg Gln Ile Lys Ile Trp Phe Gln Gln Arg Arg Met Lys Trp Lys Lys
1               5                   10                  15

Lys Ala Tyr Ala Arg Ile Gly Asn Ser Tyr Phe Lys
            20                  25

<210> SEQ ID NO 32
<211> LENGTH: 28
<212> TYPE: PRT
<213> ORGANISM: Artificial Sequence
<220> FEATURE:
<223> OTHER INFORMATION: chimeric peptide

<400> SEQUENCE: 32

Arg Gln Ile Lys Ile Trp Phe Gln Asn Lys Arg Met Lys Trp Lys Lys
1               5                   10                  15

Lys Ala Tyr Ala Arg Ile Gly Asn Ser Tyr Phe Lys
            20                  25

<210> SEQ ID NO 33
<211> LENGTH: 28
<212> TYPE: PRT
<213> ORGANISM: Artificial Sequence
<220> FEATURE:
<223> OTHER INFORMATION: chimeric peptide

<400> SEQUENCE: 33

Arg Gln Ile Lys Ile Trp Phe Gln Asn Arg Lys Met Lys Trp Lys Lys
1               5                   10                  15

Lys Ala Tyr Ala Arg Ile Gly Asn Ser Tyr Phe Lys
            20                  25

<210> SEQ ID NO 34
<211> LENGTH: 28
<212> TYPE: PRT
<213> ORGANISM: Artificial Sequence
<220> FEATURE:
<223> OTHER INFORMATION: chimeric peptide

<400> SEQUENCE: 34

Arg Gln Ile Lys Ile Trp Phe Gln Asn Arg Arg Cys Lys Trp Lys Lys
1               5                   10                  15

Lys Ala Tyr Ala Arg Ile Gly Asn Ser Tyr Phe Lys
            20                  25

<210> SEQ ID NO 35
```

```
<211> LENGTH: 28
<212> TYPE: PRT
<213> ORGANISM: Artificial Sequence
<220> FEATURE:
<223> OTHER INFORMATION: chimeric peptide

<400> SEQUENCE: 35

Arg Gln Ile Lys Ile Trp Phe Gln Asn Arg Arg Met Arg Trp Lys Lys
1               5                   10                  15

Lys Ala Tyr Ala Arg Ile Gly Asn Ser Tyr Phe Lys
            20                  25

<210> SEQ ID NO 36
<211> LENGTH: 28
<212> TYPE: PRT
<213> ORGANISM: Artificial Sequence
<220> FEATURE:
<223> OTHER INFORMATION: chimeric peptide

<400> SEQUENCE: 36

Arg Gln Ile Lys Ile Trp Phe Gln Asn Arg Arg Met Lys Tyr Lys Lys
1               5                   10                  15

Lys Ala Tyr Ala Arg Ile Gly Asn Ser Tyr Phe Lys
            20                  25

<210> SEQ ID NO 37
<211> LENGTH: 28
<212> TYPE: PRT
<213> ORGANISM: Artificial Sequence
<220> FEATURE:
<223> OTHER INFORMATION: chimeric peptide

<400> SEQUENCE: 37

Arg Gln Ile Lys Ile Trp Phe Gln Asn Arg Arg Met Lys Trp Arg Lys
1               5                   10                  15

Lys Ala Tyr Ala Arg Ile Gly Asn Ser Tyr Phe Lys
            20                  25

<210> SEQ ID NO 38
<211> LENGTH: 28
<212> TYPE: PRT
<213> ORGANISM: Artificial Sequence
<220> FEATURE:
<223> OTHER INFORMATION: chimeric peptide

<400> SEQUENCE: 38

Arg Gln Ile Lys Ile Trp Phe Gln Asn Arg Arg Met Lys Trp Lys Arg
1               5                   10                  15

Lys Ala Tyr Ala Arg Ile Gly Asn Ser Tyr Phe Lys
            20                  25

<210> SEQ ID NO 39
<211> LENGTH: 32
<212> TYPE: PRT
<213> ORGANISM: Artificial Sequence
<220> FEATURE:
<223> OTHER INFORMATION: chimeric peptide

<400> SEQUENCE: 39

Arg Gln Ile Lys Ile Trp Phe Gln Asn Arg Arg Met Lys Trp Lys Lys
1               5                   10                  15

Arg Gln Ile Ala Lys Ala Tyr Ala Arg Ile Gly Asn Ser Tyr Phe Lys
            20                  25                  30

<210> SEQ ID NO 40
```

```
<211> LENGTH: 23
<212> TYPE: PRT
<213> ORGANISM: Artificial Sequence
<220> FEATURE:
<223> OTHER INFORMATION: chimeric peptide

<400> SEQUENCE: 40

Arg Arg Arg Arg Arg Arg Arg Arg Arg Arg Lys Ala Tyr Ala Arg
1               5                   10                  15

Ile Gly Asn Ser Tyr Phe Lys
            20

<210> SEQ ID NO 41
<211> LENGTH: 129
<212> TYPE: PRT
<213> ORGANISM: Artificial Sequence
<220> FEATURE:
<223> OTHER INFORMATION: Hsp90 C-terminal EEVD binding amino acid
      sequence in TRP domain

<400> SEQUENCE: 41

Ala Leu Lys Glu Lys Glu Leu Gly Asn Asp Ala Tyr Lys Lys Lys Asp
1               5                   10                  15

Phe Asp Thr Ala Leu Lys His Tyr Asp Lys Ala Lys Glu Leu Asp Pro
            20                  25                  30

Thr Asn Met Thr Tyr Ile Thr Asn Gln Ala Ala Val Tyr Phe Glu Lys
        35                  40                  45

Gly Asp Tyr Asn Lys Cys Arg Glu Leu Cys Glu Lys Ala Ile Glu Val
    50                  55                  60

Gly Arg Glu Asn Arg Glu Asp Tyr Arg Gln Ile Ala Lys Ala Tyr Ala
65                  70                  75                  80

Arg Ile Gly Asn Ser Tyr Phe Lys Glu Glu Lys Tyr Lys Asp Ala Ile
                85                  90                  95

His Phe Tyr Asn Lys Ser Leu Ala Glu His Arg Thr Pro Asp Val Leu
            100                 105                 110

Lys Lys Cys Gln Gln Ala Glu Lys Ile Leu Lys Glu Gln Glu Arg Leu
        115                 120                 125

Ala

<210> SEQ ID NO 42
<211> LENGTH: 21
<212> TYPE: PRT
<213> ORGANISM: Artificial Sequence
<220> FEATURE:
<223> OTHER INFORMATION: chimeric peptide

<400> SEQUENCE: 42

Arg Gln Ile Lys Ile Trp Phe Gln Asn Arg Arg Met Lys Trp Lys Lys
1               5                   10                  15

Lys Ala Tyr Ala Arg
            20

<210> SEQ ID NO 43
<211> LENGTH: 12
<212> TYPE: PRT
<213> ORGANISM: Artificial Sequence
<220> FEATURE:
<223> OTHER INFORMATION: synthetic peptide

<400> SEQUENCE: 43

Lys Ala Tyr Ala Arg Ile Gly Asn Ser Tyr Phe Lys
1               5                   10
```

```
<210> SEQ ID NO 44
<211> LENGTH: 29
<212> TYPE: PRT
<213> ORGANISM: Artificial Sequence
<220> FEATURE:
<223> OTHER INFORMATION: chimeric peptide

<400> SEQUENCE: 44

Arg Gln Ile Lys Ile Trp Phe Gln Asn Arg Arg Met Lys Trp Lys Lys
1               5                   10                  15

Lys Ala Tyr Ala Ala Ala Gly Asn Ser Tyr Thr Phe Lys
            20                  25

<210> SEQ ID NO 45
<211> LENGTH: 28
<212> TYPE: PRT
<213> ORGANISM: Artificial Sequence
<220> FEATURE:
<223> OTHER INFORMATION: chimeric peptide

<400> SEQUENCE: 45

Arg Gln Ile Lys Ile Trp Phe Gln Asn Arg Arg Met Lys Trp Lys Lys
1               5                   10                  15

Lys Ala Tyr Ala Arg Ile Gly Asn Ser Gly Gly Gly
            20                  25

<210> SEQ ID NO 46
<211> LENGTH: 12
<212> TYPE: PRT
<213> ORGANISM: Artificial Sequence
<220> FEATURE:
<223> OTHER INFORMATION: human Tom 70 sequence

<400> SEQUENCE: 46

Lys Ala Leu Phe Arg Arg Ala Lys Ala His Glu Lys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Tom 34 sequence

<400> SEQUENCE: 47

Lys Ala Phe Tyr Arg Arg Ala Gln Ala His Ala Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: FKBP52 sequence

<400> SEQUENCE: 48

Lys Gly Leu Phe Arg Arg Gly Glu Ala His Leu Ala
1               5                   10

<210> SEQ ID NO 49
<211> LENGTH: 12
<212> TYPE: PRT
<213> ORGANISM: Artificial Sequence
<220> FEATURE:
<223> OTHER INFORMATION: CYP40 sequence

<400> SEQUENCE: 49
```

Lys Ala Leu Tyr Arg Arg Ala Gln Gly Trp Gln Gly
1               5                   10

<210> SEQ ID NO 50
<211> LENGTH: 23
<212> TYPE: PRT
<213> ORGANISM: Artificial Sequence
<220> FEATURE:
<223> OTHER INFORMATION: TAT-TPR sequence

<400> SEQUENCE: 50

Tyr Gly Arg Lys Lys Arg Arg Gln Arg Arg Lys Ala Tyr Ala Arg
1               5                   10                  15

Ile Gly Asn Ser Tyr Phe Lys
            20

<210> SEQ ID NO 51
<211> LENGTH: 28
<212> TYPE: PRT
<213> ORGANISM: Artificial Sequence
<220> FEATURE:
<223> OTHER INFORMATION: Antp-TPR R5A peptide

<400> SEQUENCE: 51

Arg Gln Ile Lys Ile Trp Phe Gln Asn Arg Arg Met Lys Trp Lys Lys
1               5                   10                  15

Lys Ala Tyr Ala Ala Ile Gly Asn Ser Tyr Phe Lys
            20                  25

<210> SEQ ID NO 52
<211> LENGTH: 28
<212> TYPE: PRT
<213> ORGANISM: Artificial Sequence
<220> FEATURE:
<223> OTHER INFORMATION: Antp-TPR I6A peptide

<400> SEQUENCE: 52

Arg Gln Ile Lys Ile Trp Phe Gln Asn Arg Arg Met Lys Trp Lys Lys
1               5                   10                  15

Lys Ala Tyr Ala Arg Ala Gly Asn Ser Tyr Phe Lys
            20                  25

<210> SEQ ID NO 53
<211> LENGTH: 28
<212> TYPE: PRT
<213> ORGANISM: Artificial Sequence
<220> FEATURE:
<223> OTHER INFORMATION: Antp-TPR A2G,A4G,S9Y,F11Y peptide

<400> SEQUENCE: 53

Arg Gln Ile Lys Ile Trp Phe Gln Asn Arg Arg Met Lys Trp Lys Lys
1               5                   10                  15

Lys Gly Tyr Gly Arg Ile Gly Asn Tyr Tyr Tyr Lys
            20                  25

<210> SEQ ID NO 54
<211> LENGTH: 28
<212> TYPE: PRT
<213> ORGANISM: Artificial Sequence
<220> FEATURE:
<223> OTHER INFORMATION: Antp-scramble peptide

<400> SEQUENCE: 54

Arg Gln Ile Lys Ile Trp Phe Gln Asn Arg Arg Met Lys Trp Lys Lys
1               5                   10                  15

Arg Lys Phe Ser Ala Ala Ile Gly Tyr Asn Lys Tyr
            20                  25

<210> SEQ ID NO 55
<211> LENGTH: 14
<212> TYPE: PRT
<213> ORGANISM: Homo sapiens

<400> SEQUENCE: 55

Leu Glu Gly Asp Asp Asp Thr Ser Arg Met Glu Glu Val Asp
1               5                   10

<210> SEQ ID NO 56
<211> LENGTH: 14
<212> TYPE: PRT
<213> ORGANISM: Mus musculus

<400> SEQUENCE: 56

Leu Glu Gly Asp Asp Asp Thr Ser Arg Met Glu Glu Val Asp
1               5                   10

<210> SEQ ID NO 57
<211> LENGTH: 14
<212> TYPE: PRT
<213> ORGANISM: Rattus norvegicus

<400> SEQUENCE: 57

Leu Glu Gly Asp Asp Asp Thr Ser Arg Met Glu Glu Val Asp
1               5                   10

<210> SEQ ID NO 58
<211> LENGTH: 14
<212> TYPE: PRT
<213> ORGANISM: Bos taurus

<400> SEQUENCE: 58

Leu Glu Gly Asp Asp Asp Thr Ser Arg Met Glu Glu Val Asp
1               5                   10

<210> SEQ ID NO 59
<211> LENGTH: 30
<212> TYPE: PRT
<213> ORGANISM: Homo sapiens

<400> SEQUENCE: 59

Tyr Arg Gln Ile Ala Lys Ala Tyr Ala Arg Ile Gly Asn Ser Tyr Phe
1               5                   10                  15

Lys Glu Glu Lys Tyr Lys Asp Ala Ile His Phe Tyr Asn Lys
            20                  25                  30

<210> SEQ ID NO 60
<211> LENGTH: 30
<212> TYPE: PRT
<213> ORGANISM: Mus musculus

<400> SEQUENCE: 60

Tyr Arg Gln Ile Ala Lys Ala Tyr Ala Arg Ile Gly Asn Ser Tyr Phe
1               5                   10                  15

Lys Glu Glu Lys Tyr Lys Asp Ala Ile His Phe Tyr Asn Lys
            20                  25                  30

<210> SEQ ID NO 61
<211> LENGTH: 30
<212> TYPE: PRT

-continued

<213> ORGANISM: Rattus norvegicus

<400> SEQUENCE: 61

Tyr Arg Gln Ile Ala Lys Ala Tyr Ala Arg Ile Gly Asn Ser Tyr Phe
1               5                   10                  15

Lys Glu Glu Arg Tyr Lys Asp Ala Ile His Phe Tyr Asn Lys
            20                  25                  30

<210> SEQ ID NO 62
<211> LENGTH: 30
<212> TYPE: PRT
<213> ORGANISM: Bos taurus

<400> SEQUENCE: 62

Tyr Arg Gln Ile Ala Lys Ala Tyr Ala Arg Ile Gly Asn Ser Tyr Phe
1               5                   10                  15

Lys Glu Glu Lys Tyr Lys Asp Ala Ile His Phe Tyr Asn Lys
            20                  25                  30

<210> SEQ ID NO 63
<211> LENGTH: 4
<212> TYPE: PRT
<213> ORGANISM: Artificial Sequence
<220> FEATURE:
<223> OTHER INFORMATION: Hsp90 C-terminal sequence

<400> SEQUENCE: 63

Glu Glu Val Asp
1

<210> SEQ ID NO 64
<211> LENGTH: 5
<212> TYPE: PRT
<213> ORGANISM: Artificial Sequence
<220> FEATURE:
<223> OTHER INFORMATION: Hsp90 C-terminal sequence

<400> SEQUENCE: 64

Met Glu Glu Val Asp
1               5

<210> SEQ ID NO 65
<211> LENGTH: 21
<212> TYPE: PRT
<213> ORGANISM: Artificial Sequence
<220> FEATURE:
<223> OTHER INFORMATION: Antp-RAYAR

<400> SEQUENCE: 65

Arg Gln Ile Lys Ile Trp Phe Gln Asn Arg Arg Met Lys Trp Lys Lys
1               5                   10                  15

Arg Ala Tyr Ala Arg
            20

<210> SEQ ID NO 66
<211> LENGTH: 21
<212> TYPE: PRT
<213> ORGANISM: Artificial Sequence
<220> FEATURE:
<223> OTHER INFORMATION: Antp-AAYAR

<400> SEQUENCE: 66

Arg Gln Ile Lys Ile Trp Phe Gln Asn Arg Arg Met Lys Trp Lys Lys
1               5                   10                  15

Ala Ala Tyr Ala Arg

<210> SEQ ID NO 67
<211> LENGTH: 21
<212> TYPE: PRT
<213> ORGANISM: Artificial Sequence
<220> FEATURE:
<223> OTHER INFORMATION: Antp-KGYAR

<400> SEQUENCE: 67

Arg Gln Ile Lys Ile Trp Phe Gln Asn Arg Arg Met Lys Trp Lys Lys
1               5                   10                  15

Lys Gly Tyr Ala Arg
            20

<210> SEQ ID NO 68
<211> LENGTH: 21
<212> TYPE: PRT
<213> ORGANISM: Artificial Sequence
<220> FEATURE:
<223> OTHER INFORMATION: Antp-KALAR

<400> SEQUENCE: 68

Arg Gln Ile Lys Ile Trp Phe Gln Asn Arg Arg Met Lys Trp Lys Lys
1               5                   10                  15

Lys Ala Leu Ala Arg
            20

<210> SEQ ID NO 69
<211> LENGTH: 21
<212> TYPE: PRT
<213> ORGANISM: Artificial Sequence
<220> FEATURE:
<223> OTHER INFORMATION: Antp-KAYGR

<400> SEQUENCE: 69

Arg Gln Ile Lys Ile Trp Phe Gln Asn Arg Arg Met Lys Trp Lys Lys
1               5                   10                  15

Lys Ala Tyr Gly Arg
            20

<210> SEQ ID NO 70
<211> LENGTH: 13
<212> TYPE: PRT
<213> ORGANISM: Artificial Sequence
<220> FEATURE:
<223> OTHER INFORMATION: TPR mutant 1

<400> SEQUENCE: 70

Lys Ala Tyr Ala Ala Gly Asn Ser Tyr Thr Phe Lys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: TPR mutant 2

<400> SEQUENCE: 71

Lys Ala Tyr Ala Arg Ile Gly Asn Ser Gly Gly Gly
1               5                   10

<210> SEQ ID NO 72
<211> LENGTH: 12
<212> TYPE: PRT

```
<213> ORGANISM: Artificial Sequence
<220> FEATURE:
<223> OTHER INFORMATION: TPR scramble

<400> SEQUENCE: 72

Arg Lys Phe Ser Ala Ala Ile Gly Tyr Asn Lys Tyr
1               5                   10
```

HSP90-TARGETED ANTI-CANCER CHIMERIC PEPTIDE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 570025_403USPC_CORRECTED_SEQUENCE_LISTING.txt. The text file is about 25 KB, was created on Sep. 7, 2011, and is being submitted electronically via EFS-Web.

TECHNICAL FIELD

The present invention relates to a medicine targeted to Hsp90.

BACKGROUND ART

Immunotoxins, monoclonal antibodies or ligands, which are bound to a plant or bacterial toxin and specific for proteins overexpressed on the surface of cancer cells, have been studied intensively, especially on the possible use thereof as anti-cancer agents (Non-patent Document 1). A number of immunotoxins have been studied in preclinical tests and clinical tests, and the use of an interleukin-2-diphtheria toxin (IL2-DT; Ontak®, Eisai) for the treatment of cutaneous T-cell lymphoma (CTCL) has been approved by the U.S. Food and Drug Administration (FDA) (Non-patent Documents 2 and 3). In addition, *Pseudomonas* exotoxin-based immunotoxins including interleukin-4-Pseudomonas exotoxin [IL4 (38-37)-PE38 KDEL] and interleukin-13-Pseudomonas exotoxin (IL13-PE38QQR) are currently studied in clinical tests (Non-patent Documents 4 and 5). Diphtheria toxin and *Pseudomonas* exotoxin are both incorporated into lysosome, activated therein, translocated to cytosol, and acts by catalytically inactivating the elongation factor 2 in a ribosome complex. This mechanism of action allows efficient destruction of non-replicating tumor cells in the dormant state by the immunotoxins.

Although the approach of targeting cancer by using a bacterial toxin-based immunotoxin is attractive, there are restrictions due to the hepatotoxicity caused by the bacterial toxin and the immunogenicity induced by the toxin protein (Non-patent Documents 2, 4 and 6). Immunotoxins generally have a molecular size larger than that of compound or fragment antibody medicines and thus, may possibly interfere with efficient penetration of the medicine into the tumor mass in a human body. To overcome this problem, there exists an urgent need for a new-generation of immunotoxin with an advanced approach.

Hsp90 protein, one of the heat shock proteins, which is present widely in every cell, is one of the important proteins essential for regulation of cell function. Recently, because survivin, an anti-apoptosis protein (inhibiting apoptosis of cells) expressed in a large amount in cancer cells, is folded correctly by the Hsp90 and thus exerts its function, studies on geldanamycin, a compound showing an anti-cancer action by inhibition of the Hsp90 activity, are widely reported. However, the inhibition of protein function by the compound is inevitably associated with side effects, because the compound is stable in cells and thus can possibly cause functional disorders in normal cells.

Because Hsp90 is also found in normal cells in large amounts, an Hsp90 inhibitor may also show its action in normal cells, thereby causing the problem of side effects. The toxicity of geldanamycin is not allowable, and the development is a derivative thereof that has an Hsp90 inhibitory effect similar to geldanamycin and with lower nephrotoxicity and hepatotoxicity, i.e., 17-allylaminogeldanamycin (17-AAG) (also called Tanespimycin).

A candidate anti-cancer agent called shepherdin was proposed for Hsp90 (Non-patent Documents 7 and 8). However, shepherdin directly inhibits the binding between survivin and Hsp90 and leads to destabilization of the protein to be bound and the like and thereby disabling the inherent function by contact thereof with the ATP pocket, but the in vivo effect thereof cannot be said to be effective. In addition, there are still problems that require room for improvement even if the in vitro results are taken into consideration.

Thus, there exists a need in the art for the design of an anti-cancer agent with a new structure that is highly selective to cancer cells and effective also in vitro.

There is also a need in the art for development of a novel Hsp-targeted medicine.

PRIOR ART DOCUMENTS

Non-Patent Documents

[Non-patent Document 1] Pastan I. Targeted therapy of cancer with recombinant immunotoxins. Biochim Biophys Acta 1997; 1333: C1-6

[Non-patent Document 2] Kawakami K, Nakajima O, Morishita R, Nagai R. Targeted anticancer immunotoxins and cytotoxic agents with direct killing moieties. The Sci World J 2006; 6: 781-90

[Non-patent Document 3] Kreitman R J. Immunotoxins for targeted cancer therapy. AAPS J 2006; 8: E532-51

[Non-patent Document 4] Rand R W, Kreitman R J, Patronas N, Varricchio F, Pastan I, Puri R K. Intratumoral administration of recombinant circularly permuted interleukin-4-Pseudomonas exotoxin in patients with high-grade glioma. Clin Cancer Res 2000; 6: 2157-65

[Non-patent Document 5] Kunwar S, Prados M D, Chang S M, et al. Cintredekin Besudotox Intraparenchymal Study Group. Direct intracerebral delivery of cintredekin besudotox (IL13-PE38QQR) in recurrent malignant glioma: a report by the Cintredekin Besudotox Intraparenchymal Study Group. J Clin Oncol 2007; 25: 837-44

[Non-patent Document 6] Frankel A E, Kreitman R J, Sausville E A. Targeted toxins. Clin Cancer Res 2000; 6: 326-34

[Non-patent Document 7] Plescia J, Salz W, Xia F, et al. Rational design of shepherdin, a novel anticancer agent. Cancer Cell 2005; 7: 457-68.

[Non-patent Document 8] Gyurkocza B, Plescia J, Raskett C M, et al. Antileukemic activity of shepherdin and molecular diversity of Hsp90 inhibitors. J Natl Cancer Inst 2006; 98: 1068-77.

SUMMARY OF THE INVENTION

Problems to be Solved by the Invention

It is an object of the present invention to provide an anti-cancer agent or a substance usable in DDS without adverse reactions caused by the stability thereof in cells and functional disorders to normal cells. In particular, it is an object of the present invention to design an anti-cancer agent of a new structure that is selective from normal cells, shows anti-cancer activity in vivo at low dosage, has fewer adverse reactions, and is higher in efficiency and efficacy.

Means for Solving the Problems

The present inventors have found that Hsp90 does not have a particular function alone, but only shows its chaperone function in assisting folding of proteins such as survivin, when a partner protein, Hop, is bound thereto. Thus, in the present invention, attention was given to the amino acids in the TPR (tetratricopeptide repeat) domain, which is important for binding of Hop to Hsp90, and a new peptide having a cell-killing ability specifically for cancer cells was invented by combining the amino acids with a conventionally reported cell-penetrating peptide Antp and introducing the chimeric peptide into cells, and the efficacy thereof was proven in experiments. It has also been found that it is possible in the present invention to prepare an anti-cancer peptide agent that is selective for cancer cells and shows its anti-cancer effect in vivo, particularly by systemic administration in an amount of several (1 to 5) mg/kg, which was not expected based on the findings concerning Hsp90 by conventional technology.

It has now been experimentally confirmed that the TPR peptide alone does not have the cell-killing effect at all and the TPR peptide itself should be incorporated into cells, and thus, the present invention provides a delivery agent for delivering an objective substance containing an Hsp90 TPR domain-binding peptide to cancer cells in a drug delivery system (DDS). Such a concept of DDS is confirmed by observing the cell-killing effect, for example, of a transfection reagent, such as that in the form of a liposome, specifically by introducing a TPR peptide and a scramble peptide (also referred to as "scramble (peptide)") into cells at the same concentrations by using a transfection reagent (introduced in the form of a liposome).

Accordingly, the present invention provides the following:

In an aspect, the present invention provides a delivery agent for delivering an objective substance containing an Hsp90 TPR domain-binding peptide to cancer cells and a relevant drug delivery system (DDS).

In an embodiment, the Hsp90 TPR domain-binding peptide used in the present invention and the objective substance are contained, as they are or are not bound to each other.

In an embodiment, the Hsp90 TPR domain-binding peptide used in the present invention and the objective substance are a fusion substance in which they are bound to each other.

In a preferable embodiment, the fusion substance used in the present invention is a peptide.

In an embodiment, the Hsp90 TPR domain binding peptide used in the present invention and the objective substance are contained as they are not bound to each other and are instead dispersed.

In an embodiment, the Hsp90 TPR domain-binding peptide used in the present invention is contained on a vehicle.

In an embodiment, the Hsp90 TPR domain-binding peptide used in the present invention is contained on a vehicle and the objective substance is contained in the vehicle.

In a preferable embodiment, the vehicle used in the present invention is a liposome.

In another aspect, the present invention relates to a medicine for regulation of cancer cells, containing an Hsp90 TPR domain-binding peptide and an objective substance. In an embodiment, the medicine is a composition.

In an embodiment, the objective substance used in the present invention is an anti-cancer agent.

In an embodiment, the Hsp90 TPR domain-binding peptide used in the present invention is present on a vehicle.

In an embodiment, the vehicle used in the present invention is a liposome.

In yet another aspect, the present invention provides a peptide toxin containing a target-binding peptide and a cell-killing lytic peptide component.

In yet another aspect, the present invention provides a chimeric peptide containing an Hsp90 TPR domain-binding peptide and a cell-penetrating peptide.

In an embodiment, the Hsp90 TPR domain-binding peptide used in the present invention has an amino acid sequence KAYARIGNSYFK (SEQ ID NO: 4; wherein each alphabet is a single-character expression of an amino acid) or a variant sequence thereof.

In a preferable embodiment, the Hsp90 TPR domain-binding peptide used in the present invention has an amino acid sequence $X_1X_2X_3X_4X_5X_6X_7X_8X_9X_{10}X_{11}X_{12}$ (SEQ ID NO: 1), wherein:

$X_1$ is an amino acid K or an amino acid similar thereto;
$X_2$ is an amino acid A or an amino acid similar thereto;
$X_3$ is an amino acid Y or an amino acid similar thereto;
$X_4$ is an amino acid A or an amino acid similar thereto;
$X_5$ is an amino acid R or an amino acid similar thereto;
$X_6$ is an amino acid I or an amino acid similar thereto;
$X_7$ is an amino acid G or an amino acid similar thereto;
$X_8$ is an amino acid N or an amino acid similar thereto;
$X_9$ is an amino acid S or an amino acid similar thereto;
$X_{10}$ is an amino acid Y or an amino acid similar thereto;
$X_{11}$ is an amino acid F or an amino acid similar thereto; and
$X_{12}$ is an amino acid K or an amino acid similar thereto; or
a sequence of elongated TPR peptide RQIAKAYARIGNSYFKEEKYK (SEQ ID NO: 43), wherein amino acids are respectively represented by the single-character expression.

In an embodiment, the Hsp90 TPR domain-binding peptide used in the present invention has an amino acid sequence $X_1X_2X_3X_4X_5X_6X_7X_8X_9X_{10}X_{11}X_{12}$ (SEQ ID NO: 1), wherein:

$X_1$ is K, R or A (preferably, K);
$X_2$ is A or G;
$X_3$ is Y or L (preferably, Y);
$X_4$ is A or G;
$X_5$ is R, A or K (preferably, R);
$X_6$ is I, A or R (preferably, R);
$X_7$ is G or A;
$X_8$ is N or Q;
$X_9$ is S or Y;
$X_{10}$ is Y or S;
$X_{11}$ is F or Y; and/or
$X_{12}$ is K or R, or
a sequence of elongated TPR peptide RQIAKAYARIGNSYFKEEKYK (SEQ ID NO: 43).

In an embodiment, the present invention includes the Hsp90 TPR domain-binding peptide, wherein:

$X_2$ is G;
$X_4$ is G;
$X_7$ is A;
$X_8$ is Q;
$X_9$ is Y;
$X_{10}$ is S;
$X_{11}$ is Y; and/or
$X_{12}$ is R.

In an embodiment, the present invention includes the Hsp90 TPR domain-binding peptide, wherein:

$X_4$ is G;
$X_9$ is Y; and
$X_{11}$ is Y.

In an embodiment, the Hsp90 TPR domain-binding peptide used in the present invention has an amino acid sequence KAYAR (SEQ ID NO: 3).

In an embodiment, the Hsp90 TPR domain-binding peptide used in the present invention has an amino acid sequence KAYARX$_a$X$_b$X$_c$X$_d$Z$_1$Z$_2$Z$_3$ (SEQ ID NO: 2), wherein X$_a$, X$_b$, X$_c$ and X$_d$ represent independently any amino acid and Z$_1$Z$_2$Z$_3$ is amino acids important for formation and preservation of a helix.

In a preferable embodiment, the Z$_1$Z$_2$Z$_3$ is (Y/H) (F/E/M/L/S) (K/A/L/Q/S) (i.e., Z$_1$ represents Y or H, Z$_2$ represents F, E, M, L or S, and Z$_3$ represents K, A, L, Q or S).

In an embodiment, the Hsp90 TPR domain-binding peptide used in the present invention is KAYAR (SEQ ID NO: 3) or KAYARIGNSYFK (SEQ ID NO: 4).

In an embodiment, the cell-penetrating peptide used in the present invention is an antennapedia homeobox sequence (Antp) RQIKIWFQNRRMKWKK (SEQ ID NO: 5), YGRKKRRQRRR (SEQ ID NO: 6), which is TAT, or RRRRRRRRRR (SEQ ID NO: 7), or a variant sequence thereof.

In an embodiment, the cell-killing peptide used in the present invention is RQIKIWFQNRRMKWKK (SEQ ID NO: 5) or a variant sequence thereof, and the variant sequence has an amino acid sequence Y$_1$Y$_2$Y$_3$Y$_4$Y$_5$Y$_6$Y$_7$Y$_8$Y$_9$Y$_{10}$Y$_{11}$Y$_{12}$Y$_{13}$Y$_{14}$Y$_{15}$Y$_{16}$ (SEQ ID NO: 8), wherein:
Y$_1$ is an amino acid R or an amino acid similar thereto;
Y$_2$ is an amino acid Q or an amino acid similar thereto;
Y$_3$ is an amino acid I or an amino acid similar thereto;
Y$_4$ is an amino acid K or an amino acid similar thereto;
Y$_5$ is an amino acid I or an amino acid similar thereto;
Y$_6$ is an amino acid Q or an amino acid similar thereto;
Y$_7$ is an amino acid F or an amino acid similar thereto;
Y$_8$ is an amino acid Q or an amino acid similar thereto;
Y$_9$ is an amino acid N or an amino acid similar thereto;
Y$_{10}$ is an amino acid R or an amino acid similar thereto;
Y$_{11}$ is an amino acid R or an amino acid similar thereto;
Y$_{12}$ is an amino acid M or an amino acid similar thereto;
Y$_{13}$ is an amino acid K or an amino acid similar thereto;
Y$_{14}$ is an amino acid K or an amino acid similar thereto;
Y$_{15}$ is an amino acid K or an amino acid similar thereto; and
Y$_{16}$ is an amino acid K or an amino acid similar thereto.

In an embodiment, the cell-killing peptide used in the present invention is RQIKIWFQNRRMKWKK (SEQ ID NO: 5) or a variant sequence thereof and the variant sequence has an amino acid sequence Y$_1$Y$_2$Y$_3$Y$_4$Y$_5$Y$_6$Y$_7$Y$_8$Y$_9$Y$_{10}$Y$_{11}$Y$_{12}$Y$_{13}$Y$_{14}$Y$_{15}$Y$_{16}$ (SEQ ID NO: 8), wherein:
Y$_1$ is R or K;
Y$_2$ is Q or N;
Y$_3$ is I or L;
Y$_4$ is K or R;
Y$_5$ is I or L;
Y$_6$ is W or Y;
Y$_7$ is F or Y;
Y$_8$ is Q or N;
Y$_9$ is N or Q;
Y$_{10}$ is R or K;
Y$_{11}$ is R or K;
Y$_{12}$ is M or C;
Y$_{13}$ is K or R;
Y$_{14}$ is W or Y;
Y$_{15}$ is K or R; and/or
Y$_{16}$ is K or R.

In a preferable embodiment, the present invention includes a cell-penetrating peptide having the sequence wherein:
Y$_2$ is N;
Y$_4$ is R;
Y$_8$ is N;
Y$_9$ is Q;
Y$_{10}$ is K;
Y$_{11}$ is K;
Y$_{12}$ is C;
Y$_{13}$ is R;
Y$_{14}$ is Y;
Y$_{15}$ is R; and/or
Y$_{16}$ is R.

In a preferable embodiment, the present invention includes the cell-penetrating peptide according to the present invention, having the sequence wherein
Y$_4$ is R;
Y$_9$ is Q;
Y$_{12}$ is C; and/or
Y$_{16}$ is R.

In a preferable embodiment, the chimeric peptide according to the present invention is a chimeric peptide having a sequence of

```
RQIKIWFQNRRMKWKKKAYARIGNSYFK,     (SEQ ID No. 9)
RQIKIWFQNRRMKWKKRAYARIGNSYFK,     (SEQ ID No. 10)
RQIKIWFQNRRMKWKKAAYARIGNSYFK,     (SEQ ID No. 11)
RQIKIWFQNRRMKWKKGYARIGNSYFK,     (SEQ ID No. 12)
RQIKIWFQNRRMKWKKKALARIGNSYFK,     (SEQ ID No. 13)
RQIKIWFQNRRMKWKKKAYARIGNSYFK,     (SEQ ID No. 14)
RQIKIWFQNRRMKWKKKAYAKIGNSYFK,     (SEQ ID No. 15)
RQIKIWFQNRRMKWKKKAYARRGNSYFK,     (SEQ ID No. 16)
RQIKIWFQNRRMKWKKKAYARIANSYFK,     (SEQ ID No. 17)
RQIKIWFQNRRMKWKKKAYARIGQSYFK,     (SEQ ID No. 18)
RQIKIWFQNRRMKWKKKAYARIGNYYFK,     (SEQ ID No. 19)
RQIKIWFQNRRMKWKKKAYARIGNSSFK,     (SEQ ID No. 20)
RQIKIWFQNRRMKWKKKAYARIGNSYYK,     (SEQ ID No. 21)
RQIKIWFQNRRMKWKKKAYARIGNSYFR,     (SEQ ID No. 22)
KQIKIWFQNRRMKWKKKAYARIGNSYFK,     (SEQ ID No. 23)
RNIKIWFQNRRMKWKKKAYARIGNSYFK,     (SEQ ID No. 24)
RQLKIWFQNRRMKWKKKAYARIGNSYFK,     (SEQ ID No. 25)
RQIRIWFQNRRMKWKKKAYARIGNSYFK,     (SEQ ID No. 26)
RQIKLWFQNRRMKWKKKAYARIGNSYFK,     (SEQ ID No. 27)
RQIKYWFQNRRMKWKKKAYARIGNSYFK,     (SEQ ID No. 28)
RQIKIWYQNRRMKWKKKAYARIGNSYFK,     (SEQ ID No. 29)
RQIKIWFNNRRMKWKKKAYARIGNSYFK,     (SEQ ID No. 30)
RQIKIWFQQRRMKWKKKAYARIGNSYFK,     (SEQ ID No. 31)
RQIKIWFQNKRMKWKKKAYARIGNSYFK,     (SEQ ID No. 32)
RQIKIWFQNRKMKWKKKAYARIGNSYFK,     (SEQ ID No. 33)
RQIKIWFQNRRCKWKKKAYARIGNSYFK,     (SEQ ID No. 34)
RQIKIWFQNRRMRWKKKAYARIGNSYFK,     (SEQ ID No. 35)
RQIKIWFQNRRMKYKKKAYARIGNSYFK,     (SEQ ID No. 36)
RQIKIWFQNRRMKWRKKAYARIGNSYFK,     (SEQ ID No. 37)
```

```
RQIKIWFQNRRMKWKRKAYARIGNSYFK,      (SEQ ID No. 38)

RQIKIWFQNRRMKWKKRQIAKAYARIGNSYFK,  (SEQ ID No. 39)
or

RRRRRRRRRRRKAYARIGNSYFK.           (SEQ ID No. 40)
```

In another aspect, the present invention provides a medicine, preferably a pharmaceutical composition, containing the chimeric peptide according to the present invention.

In another aspect, the present invention provides an anti-cancer agent containing the chimeric peptide according to the present invention.

In another aspect, the present invention relates to the use of the chimeric peptide according to the present invention in the production of a pharmaceutical composition.

In another aspect, the present invention relates to the use of the chimeric peptide according to the present invention in the production of an anti-cancer agent.

In another aspect, the present invention relates to a treatment method including the step of administering the chimeric peptide according to the present invention.

In another aspect, the present invention relates to a method for treating cancer including a step of administering the chimeric peptide according to the present invention.

In another aspect, the present invention relates to a method for screening a medicine using the amino acid sequence in the Hsp90's TPR domain.

In another aspect, the present invention relates to a method for screening an anti-cancer agent using the amino acid sequence in the Hsp90's TPR domain.

In a preferable embodiment, the amino acid sequence in the TPR domain binding to the Hsp90's C-terminal sequence (EEVD (SEQ ID NO: 63)) used in the present invention is ALKEKELGNDAYKKKDFDTALKHYD-KAKELDPTNMTYITNQAAVYFEKGDYNKCREL CEKAIEVGRENREDYRQIAKAYARIGN-SYFKEEKYKDAIHFYNKSLAEHRTPDVLKKCQ QAEKILKEQERLA (SEQ ID NO: 41) or an analog thereof (preferably, an analog having conservative substitution).

It will be understood that each embodiment described in all the aspects as used herein can be applied, and if possible, also to other aspects as well.

Effects of the Invention

An advantageous effect of the present invention is that a cancer specific novel medicine that shows an effect only on cancer cells and does not show much effect on normal cells is provided. It is also highly probable that the medicine may solve the problem of adverse reactions of anti-cancer drugs which is a serious issue in clinical environments. In addition, the unexpected expression of cancer cell-killing effect by peptides of only 5 amino acids, preferably 12 amino acids may also be a distinctive effect.

As described above, the present invention provides a substance useable as an anti-cancer agent or in a DDS that maintains stability in cells, does not have adverse reactions by resulting in functional disorders or the like in normal cells, and is highly selective for cancer cells and display higher in efficiency and efficacy.

BRIEF DESCRIPTION OF THE DRAWINGS

FIG. 1(A) is a schematic view of the Hop protein showing two independent TPR domains TPR1 and TPR2A, and TPR1 and TPR2A interact respectively with the C-terminal tails of Hsp70 and Hsp90. The arrow in the figure shows the interaction between TPR2A and Hsp90. FIGS. 1(B) and 1(C) show the results of analysis of the region essential for binding with Hsp90 by means of spatial structure display software (Ras Mol ver 2.7 for Macintosh (free software program, http://www.openrasmol.org/). FIG. 1(B) is a spatial structural view showing the complex between the Hop's TPR domain reported and the C-terminal sequence MEEVD (SEQ ID NO: 64) of Hsp90 (center, white). In the spatial structural view (B), the helix (arrow) important for binding with Hsp90 is the region used for designing this time and FIG. 1(C) is the spatial structural view showing the complex between the predicted peptide (left) and the Hsp90's C-terminal sequence MEEVD (SEQ ID NO: 64) (right).

FIG. 3A shows the results obtained with Antp-KAYAR (SEQ ID NO: 42); FIG. 3B shows the results obtained with Antp-KAYARIGNSYFK (SEQ ID NO: 9); FIG. 3C shows the results obtained with KAYARIGN-SYFK (SEQ ID NO: 4); and FIG. 3D shows the results obtained with TAT-KAYARIGNSYFK (SEQ ID NO: 50). FIGS. 3E and 3F show the results obtained respectively with the mutants 1 and 2 (Antp-KAYAAAGNSYFK (SEQ ID NO: 44) and Antp-KAYARIGNSGGG (SEQ ID NO: 45)). Here, the Antp has a sequence represented by SEQ ID NO: 5. The ordinate in each table represents cell survival rate (%), while the abscissa represents peptide concentration (μM).

FIG. 4 shows the results obtained by Western blotting of cells higher in cell-killing effect. Fig. (A): the amount of the client proteins expressed in the T47D cell incubated with the Antp-TPR peptide (68 μM) for 48 hours were determined by Western blotting using a specific antibody. The expression amounts of (from top) Hsp90, CDK4, Akt, survivin and β-actin (control) in the absence and presence of Antp-TPR (from left) are shown. (B) the amounts of (from top) Hsp90, Hsp70, survivin and β-actin (control) expressed in the presence of the Antp-TPR peptide (from left) in HEK cells, Caki-1 cells, Bxpc cells, T47D cells and A549 cells were determined. "α-" in the figure means that it is the antibody used during Western blotting.

FIG. 5 is a table showing the structure-activity relationship obtained when an amino acid in TPR is mutated to another amino acid, as shown in the table. It shows the cytotoxic activity of Antp-TPR variant peptides.

FIG. 8A is a table showing the structure-activity relationship obtained when an amino acid in the cell-penetrating peptide is mutated to another amino acid, as shown in the table. It shows the cytotoxic activity of Antp-TPR variant peptides.

FIG. 13 shows the results of a penetration experiment of the Antp-TPR chimeric peptide by using an acute myelogenous leukemia cell strain U937. (B): no flow of calcein (green) was observed after intracellular penetration of the Antp-TPR chimeric peptide, indicating that it had penetrated without destruction of the cell membrane. In addition, the membrane was not destroyed after peptide penetration. The arrow in the figure indicates the cells into which the peptide had penetrated.

MODE FOR CARRYING OUT THE INVENTION

Figure 1:
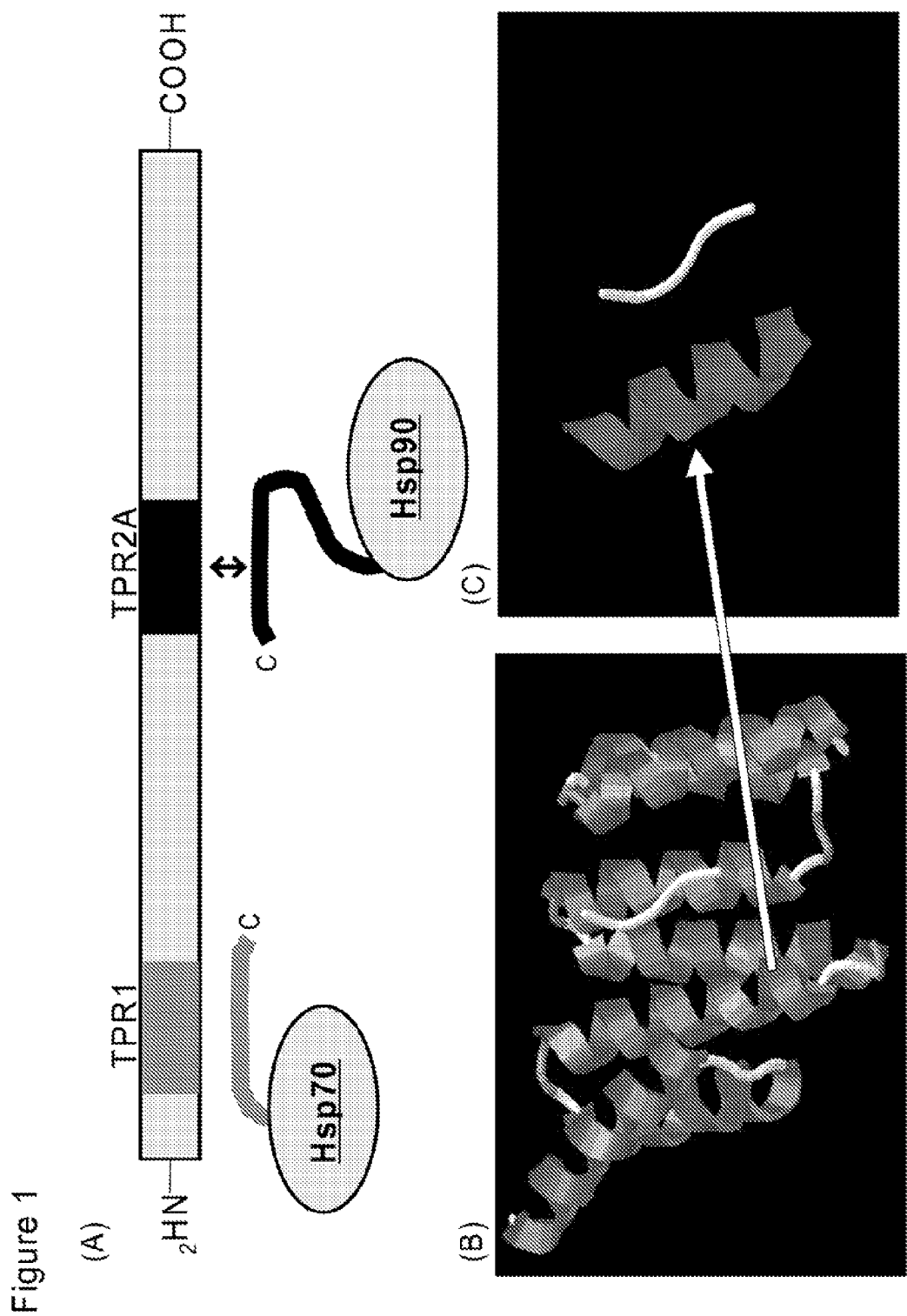
FIG. 1 includes a schematic view (A) of the heat shock protein (Hsp)-organizing protein (Hop) and spatial structural views (B and C) of the regions essential for binding between Hop and Hsp90.

Hereinafter, embodiments of the present invention will be described. Throughout the present description, a singular term (e.g., a term with "a", "an", or "the" in the case of English and corresponding articles, adjectives and others in the case of other languages) should be construed to have the meaning including that expressed by its plural term, unless specified otherwise. The terms used herein should be understood to have the same meaning as those used commonly in the art, unless specified otherwise. Thus, all professional terms and all scientific and technical terms used herein have a meaning generally recognized by those who are skilled in the art, unless defined otherwise. If there is contradiction, preference is given to the present description (including definitions).

DEFINITION OF TERMS

Hereinafter, terms used particularly as used herein will be listed.

"Hsp90", as used herein, is one of the heat shock proteins, i.e., a molecular chaperone having a molecular weight of about 90,000 (90 kDa) that is present most abundantly in eukaryotic cells. The structure is typically represented by the sequence of GenBank#NM_001017963 (human) or Entrez Gene ID 3320, and the homologues thereof are also included as long as they have the functions of the typical examples of Hsp.

Human Hsp90 can be prepared by constructing an *E. coli* expression vector with a histidine tag from the human Hsp90 gene sequence cDNA clone (AB1144_H10, OriGene Technologies, Inc., Rockville, Md.) by the GATEWAY system (Invitrogen), transforming the constructed expression vector (pDEST17-Hsp90) into an *E. coli* BL21 strain, confirming expression of Hsp90, purifying the Hsp90 protein by using a nickel column (His-Trap: Amersham Pharmacia, currently GE Healthcare).

Hsp90 has a role to ensure accurate folding and function of multiple intracellular proteins by interaction therewith. Examples of the proteins that interact with Hsp90 include many signal transduction molecules playing an important role in cell proliferation or differentiation, such as protein kinases and steroid hormone receptors. These proteins are expressed in a greater amount when the cell is exposed to stress. However, these proteins are present abundantly in the cytoplasm not only when under stress, but also in the normal state, and destruction of Hsp90 leads to the loss of normal functions thereof.

The "Hsp90 TPR (tetratricopeptide repeat) domain", as used herein, is a domain playing an important role for Hop to bind to Hsp90, and typically, its structure is represented by GenBank No. MN_006819 and Gene ID 10963.

A typical example thereof is ALKEKELGNDAYKKKD-FDTALKHYDKAKELDPTNMTYITNQAAVYFEKGDY-NKCREL CEKAIEVGRENREDYRQIAKAYARIGN-SYFKEEKYKDAIHFYNKSLAEHRTPDVLKKCQ QAEKILKEQERLA (SEQ ID NO: 41) or its analogous sequence. In designing the analog, it is possible to design an important peptide, for example, by determining the spatial structure (PDB ID 1ELR) of the complex structure of the TPR2A domain and the Hsp90 C-terminal peptide. The present inventors have also found that Hsp90 exhibits its function as chaperone in assisting folding of proteins such as survivin not by itself, but by binding to a partner protein Hop.

The "Hsp90 TPR domain-binding peptide", as used herein, is a peptide that can bind to the Hsp90 TPR domain, and in the present invention, because the TPR peptide did not show any cell-killing effect at all when used alone, it is considered that the Antp-TPR peptide itself penetrates also into cells.

A typical Hsp90 TPR domain-binding peptide is a peptide having the amino acid sequence $X_1X_2X_3X_4X_5X_6X_7X_8X_9X_{10}X_{11}X_{12}$ (SEQ ID NO: 1), wherein $X_1$ is an amino acid K or a hydrophilic amino acid similar thereto such as R or A or the like;

$X_2$ is an amino acid A or an aliphatic branched-chain amino acid similar thereto such as G, V, L or I or the like;

$X_3$ is an amino acid Y or a hydrophobic amino acid similar thereto such as L or the like;

$X_4$ is an amino acid A or an aliphatic branched-chain amino acid similar to G, V, L or I or the like;

$X_5$ is an amino acid R or an amino acid similar thereto;

$X_6$ is an amino acid I or an amino acid similar thereto;

$X_7$ is an amino acid G or an amino acid similar thereto that is found in other TPR domain such as A or the like;

$X_8$ is an amino acid N or an amino acid similar thereto that is found in other TPR domain such as Q;

$X_9$ is an amino acid S or an amino acid similar thereto having an OH group such as T or Y or the like;

$X_{10}$ is an amino acid Y or an amino acid similar thereto having an OH group such as S or T or the like;

$X_{11}$ is an amino acid F or an amino acid similar thereto having an aromatic group such as Y or the like;

$X_{12}$ is an amino acid K or a basic amino acid similar thereto such as R or the like, and it should be understood that any combination of $X_1$ to $X_{12}$ can be effective.

The "amino acid sequences that can be found in other TPR domain" include, but are not limited to: KALFRRAKAHEK (human Tom 70; SEQ ID NO: 46), KAFYRRAQAHAK (Tom 34; SEQ ID NO: 47), KGLFRRGEAHLA (FKBP52; SEQ ID NO: 48), and KALYRRAQGWQG (CYP40; SEQ ID NO: 49).

In one embodiment, the amino acid sequence has $X_1X_2X_3X_4X_5X_6X_7X_8X_9X_{10}X_{11}X_{12}$ (SEQ ID NO: 1), wherein $X_1$ is K, R or A, preferably K;
$X_2$ is A or G;
$X_3$ is Y or L, preferably Y;
$X_4$ is A or G;
$X_5$ is R, A or K, preferably R;
$X_6$ is I, A or R, preferably I or A;
$X_7$ is G or A;
$X_8$ is N or Q;
$X_9$ is S or Y;
$X_{10}$ is Y or S;
$X_{11}$ is F or Y;
$X_{12}$ is K or R, or by RQIAKAYARIGNSYFKEEKYK (SEQ ID NO: 43), which is obtained by elongation of the TPR peptide, and it will be understood that any combination of $X_1$ to $X_{12}$ can be effective.

Preferably, those are included wherein, in the amino acid sequence above, $X_2$ is G;
$X_4$ is G;
$X_7$ is A;
$X_8$ is Q;
$X_9$ is Y;
$X_{10}$ is S;
$X_{11}$ is Y; and
$X_{12}$ is R, and it will be understood that any combination of these preferable substitutions can be effective. This is because preservation or enhancement of the effect has been observed by these substitutions in the present invention.

More preferably, those are included wherein, in the amino acid sequence above, $X_4$ is G;
$X_9$ is Y; and
$X_{11}$ is Y, and it will be understood that any combination of these preferable substitutions can be effective. This is because enhancement of the effect has been observed by these substitutions.

It should be understood that these mutations may be introduced alone or in a plurality thereof.

Another example is its elongated product "Antp-TPR slong", i.e., Antp-RQIAKAYARIGNSYFKEEKYK" (SEQ ID NO: 39). There has been no decrease in effect when the protein is elongated, and this fact indicates that the present invention can be used, independently of its amino acid length, and thus, it would be apparent for those who are skilled in the art that various sequences and lengths can be adjusted, based on the present description.

However, it will be understood that an "Hsp90 TPR domain-binding peptide" having a sequence other than those above can also be used in the present invention as long as it has the ability to bind to the Hsp90 TPR domain. A typical Hsp90 TPR domain-binding peptide is a peptide having an amino acid sequence of KAYAR or an amino acid sequence of KAYARX$_a$X$_b$X$_c$X$_d$Z$_1$Z$_2$Z$_3$ (SEQ ID NO: 2, wherein $Z_1Z_2Z_3$ may be (Y/H) (F/E/M/L/S) (K/A/L/Q/S)), wherein $X_a$, $X_b$, $X_c$ and $X_d$ each independently represents an amino acid, and examples of $Z_1Z_2Z_3$ include amino acids important for formation and preservation of a helix, such as KAYAR (SEQ ID NO: 3) itself and KAYARIGNSYFK (SEQ ID NO: 4) itself and the like.

Based on the fact demonstrated herein, the following can be understood on a mutation in the TPR (12 amino acid) region.

Proteins with an effect higher than the wild-type protein (the following symbols refer to one-character symbol of original amino acid, site number of amino acid, and one-character symbol of amino acid after mutation in the order): A2G, A4G, I6A, N8Q, S9Y and F11Y Proteins with an effect similar to that of the wild-type protein: G7A, Y10S and K12R Proteins effective but with a lower effect than the wild-type protein: K1A, K1R, Y3L, R5K, R5A and I6R.

The "cell-penetrating peptide", as used herein, is a peptide that can pass through a cell membrane to invade into a cell. The cell permeability of a peptide can be evaluated in the following test.

In the present invention, the presence of Antp can be determined by a known method (Derossi, et al., J. Biol. Chem. 1996, 271, 18188-18193.) of adding a biotinated Antp peptide entered into a cell, then adding a streptavidin-chemically labeled compound thereto, and determining its intracellular localization under a fluorescence microscope.

Alternatively, intracellular invasion can be confirmed by reaction with a streptavidin-binding antibody and subsequent observation of the localization of a similarly chemically labeled antibody under a fluorescence microscope.

Examples of the cell-penetrating peptide include an antennapedia homeobox sequence (Antp) RQIKIWFQNRRMKWKK (SEQ ID NO: 5), YGRKKRRQRRR) (SEQ ID NO: 6), which is TAT, or RRRRRRRRRRR (SEQ ID NO: 7), or a variant thereof. Typically, the structure is, for example, Gene ID 155871 (TAT protein itself). It will be understood, in the present invention, that any peptide may be used as the cell-penetrating peptide placed upstream of TPR, because the cell-killing effect could be demonstrated both with R11 and TAT.

A typical cell-penetrating peptide has the following sequence:

RQIKIWFQNRRMKWKK (SEQ ID NO: 5) or its variant sequence, and the variant sequence has an amino acid sequence of $Y_1Y_2Y_3Y_4Y_5Y_6Y_7Y_8Y_9Y_{10}Y_{11}Y_{12}Y_{13}Y_{14}Y_{15}Y_{16}$ (SEQ ID NO: 8), wherein:

$Y_1$ is an amino acid R or a hydrophilic amino acid similar thereto such as K or the like;

$Y_2$ is an amino acid Q or an amide-based amino acid similar thereto such as N or E as Glx (as used herein, "Glx" represents Gln and Glu collectively) or the like;

$Y_3$ is an amino acid I or an aliphatic amino acid similar thereto such as L or the like;

$Y_4$ is an amino acid K or a hydrophilic amino acid similar thereto such as R or the like;

$Y_5$ is an amino acid I or an aliphatic amino acid similar thereto such as L or the like;

$Y_6$ is an amino acid W or an aromatic amino acid similar thereto such as Y or the like;

$Y_7$ is an amino acid F or an aromatic amino acid similar thereto such as Y or the like;

$Y_8$ is an amino acid Q or an amide-based amino acid similar thereto such as N or E as Glx or the like;

$Y_9$ is an amino acid N or an amide-based amino acid similar thereto such as Q or the like;

$Y_{10}$ is an amino acid R or a hydrophilic amino acid similar thereto such as K or the like;

$Y_{11}$ is an amino acid R or a hydrophilic amino acid similar thereto such as K or the like;

$Y_{12}$ is an amino acid M or an S-containing amino acid similar thereto such as C or the like;

$Y_{13}$ is an amino acid K or a hydrophilic amino acid similar thereto such as R or the like;

$Y_{14}$ is an amino acid W or an aromatic amino acid similar thereto such as Y or the like;

$Y_{15}$ is an amino acid K or a hydrophilic amino acid similar thereto such as R or the like; and $Y_{16}$ is an amino acid K or a hydrophilic amino acid similar thereto such as R or the like, and it will be understood that any combination of $Y_1$ to $Y_{16}$ can be effective.

Other sequences that may be referred to for the substitution above include those containing conservative substitutions.

In a preferable embodiment, in the amino acid sequence above, $Y_1$ is R or K;
$Y_2$ is Q or N;
$Y_3$ is I or L;
$Y_4$ is K or R;
$Y_5$ is I or L;
$Y_6$ is W or Y;
$Y_7$ is F or Y;
$Y_8$ is Q or N;
$Y_9$ is N or Q;
$Y_{10}$ is R or K;
$Y_{11}$ is R or K;
$Y_{12}$ is M or C;
$Y_{13}$ is K or R;
$Y_{14}$ is W or Y;
$Y_{15}$ is K or R; and
$Y_{16}$ is K or R, and
it will be understood that any combination of $Y_1$ to $Y_{16}$ can be effective.

In a preferable embodiment, the cell-penetrating peptide according to the present invention includes those having the amino acid sequence above, wherein $Y_2$ is N;
$Y_4$ is R;
$Y_8$ is N;
$Y_9$ is Q;
$Y_{10}$ is K;
$Y_{11}$ is K;
$Y_{12}$ is C;
$Y_{13}$ is R;
$Y_{14}$ is Y;
$Y_{15}$ is R; and/or
$Y_{16}$ is R, and it will be understood that any combination of these preferable substitutions can be effective. This is because preservation or enhancement of the effect was observed by these substitutions.

In a more preferable embodiment, the cell-penetrating peptide according to the present invention includes those having the amino acid sequence above, wherein $Y_4$ is R;
$Y_9$ is Q;
$Y_{12}$ is C; or
$Y_{16}$ is R, and it will be understood that any combination of these preferable substitutions can be effective. This is because enhancement of the effect has been observed by these substitutions.

As used herein, the followings can be understood on the mutation of the Antp (cell penetration peptide unit) region.

Proteins with an effect higher than the wild-type protein (similarly expressed as TPR): K4R, N9Q, M12C and K16R Proteins with an effect similar to that of the wild-type protein: Q2N, Q8N, R10K, R11K, K13R, W14Y and K15R Proteins effective but with an effect lower than the wild-type protein: R1K, I3L, I5L, W6Y and F7Y.

It will be understood that these mutations may be introduced alone or in combination. Without wishing to be bound by theory, this is because, once a mutation is understood to be acceptable, it will also be understood that such a mutation preserves or enhances the original active three dimensional structure and interaction with the biological target of a subject and the like, and thus it is expected that a combination of a plurality of mutations will give a similar effect. The sequences in the TPR domains are higher in homology, but it has already been confirmed that the sequence strictly recognizes a combination with their partner proteins (Hsp70, Hsp90, etc.). In the case of the present invention, although there may be influences on interactions with the partner protein for the protein that showed change in activity by a single amino acid substitution, since such a substitution is expected to retain the same properties in terms of the viewpoint of the anti-cancer activity, which is the ultimate purpose of modification, it is expected that even if these amino acid substitutions occur in combination, such substitutions will still attain similar effects from such view point. This is because both Hsp70 and Hsp90 are playing important roles in proliferation and growth thereof in cancer cells.

A protein having a sequence of RQIKIWFQNRRMKWKKKAYARIGNSYFK (SEQ ID NO: 9) is preferably used. Alternatively, a protein called TAT having a sequence of YGRKKRRQRRR (SEQ ID NO: 6) may be used. A protein having a sequence of 11 consecutive R's, RRRRRRRRRRR (SEQ ID NO: 7), which is known to show cell penetration, can also be used. In addition, those who are skilled in the art can determine a preferable combination of a cell-penetrating peptide and a TPR domain-binding peptide. A combination with Antp can be preferably used.

The "amino acids important for formation and preservation of a helix", as used herein, are any amino acid sequence playing an important role in forming and preserving a helix. Typically, the TPR domain is (Y/H) (F/E/M/L/S) (K/A/L/Q/S), but it is not limited thereto.

The "chimeric peptide", as used herein, is a peptide containing two or more different genotype regions (peptides). It is also called a fusion protein. It is used for evaluation of the function of a protein domain and detection of expression of an objective protein.

The "similar amino acids", as used herein, are typically amino acids in a relationship of conservative substitution, and the following amino acids are such examples.

A: G, I, V or L
C: M (S-containing amino acid)
D: N, Q or E
E: N, Q or D
F: Y, S, A or the like
G: A
H: W or the like
I: A, L, V or (G)
K: R
L: A, I, V or (G)
M: S or the like
N: E, D or Q
P: HyP
Q: N, E or D
R: K
S: T or Y
T: S or Y
V: I, L, A, or (G)
W: H
Y: F, S or T.

The substitution between these amino acids is also called "conservative substitution" as used herein.

An amino acid frequently found in other sequences having a similar function may be used as a "similar amino acids". This is because the fact that it is substitutable is demonstrated on a fact basis. Specifically, the similar amino acids for use may be a sequence described elsewhere herein. This is because the effect of the similar amino acids described specifically is demonstrated to be retained in particular examples or included in the range understood from the demonstrated examples.

The "amino acids" frequently found in the TPR peptide of the present description are those found frequently in various TPR peptides, and typically include amino acids in the relationship of conservative substitution, and examples thereof include the following amino acids.

Those having an amino acid sequence of $X_1X_2X_3X_4X_5X_6X_7X_8X_9X_{10}X_{11}X_{12}$ (SEQ ID NO: 1), wherein:

$X_1$ is an amino acid K or a hydrophilic amino acid similar thereto such as R or A or the like;

$X_2$ is an amino acid A or an aliphatic branched-chain amino acid similar thereto such as G, V, L or I or the like;

$X_3$ is an amino acid Y or a hydrophobic amino acid similar thereto such as L or the like;

$X_4$ is an amino acid A or an aliphatic branched-chain amino acid similar thereto such as G, V, L or I or the like;

$X_5$ is an amino acid R or an amino acid similar thereto;

$X_6$ is an amino acid I or an amino acid similar thereto;

$X_7$ is an amino acid G or an amino acid similar thereto that is found in other TPR domain such as A or the like;

$X_8$ is an amino acid N or an amino acid similar thereto that is found in other TPR domain such as Q or the like;

$X_9$ is an amino acid S or an OH group-containing amino acid similar thereto such as T or Y or the like;

$X_{10}$ is an amino acid Y or an OH group-containing amino acid similar thereto such as S or T or the like;

$X_{11}$ is an amino acid F or an aromatic amino acid similar thereto such as Y or the like; and $X_{12}$ is an amino acid K or a basic amino acid similar thereto such as R or the like.

In the present invention, a specific sequence of the amino acids frequently found in the cell-penetrating peptide is that found frequently in various cell-penetrating peptides, and typical examples thereof include, those containing amino acids in the relationship of conservative substitution, specifically the following amino acids.

Such a sequence is for example RQIKIWFQNRRMK-WKK (SEQ ID NO: 5) or its variant sequence, and the variant sequence has an amino acid sequence $Y_1Y_2Y_3Y_4Y_5Y_6Y_7Y_8Y_9Y_{10}Y_{11}Y_{12}Y_{13}Y_{14}Y_{15}Y_{16}$ (SEQ ID NO: 8), wherein:

$Y_1$ is an amino acid R or a hydrophilic amino acid similar thereto such as K or the like;

$Y_2$ is an amino acid Q or an amide-based amino acid similar thereto such as N or E as Glx or the like;

$Y_3$ is an amino acid I or an aliphatic amino acid similar thereto such as L or the like;

$Y_4$ is an amino acid K or a hydrophilic amino acid similar thereto such as R or the like;

$Y_5$ is an amino acid I or an aliphatic amino acid similar thereto such as L or the like;

$Y_6$ is an amino acid W or an aromatic amino acid similar thereto such as Y or the like;

$Y_7$ is an amino acid F or an aromatic amino acid similar thereto such as Y or the like;

$Y_8$ is an amino acid Q or an amide-based amino acid similar thereto such as N or E as Glx or the like;

$Y_9$ is an amino acid N or an amide-based amino acid similar thereto such as Q or the like;

$Y_{10}$ is an amino acid R or a hydrophilic amino acid similar thereto such as K or the like;

$Y_{11}$ is an amino acid R or a hydrophilic amino acid similar thereto such as K or the like;

$Y_{12}$ is an amino acid M or an S-containing amino acid similar thereto such as C or the like;

$Y_{13}$ is an amino acid K or a hydrophilic amino acid similar thereto such as R or the like;

$Y_{14}$ is an amino acid W or an aromatic amino acid similar thereto such as Y or the like;

$Y_{15}$ is an amino acid K or a hydrophilic amino acid similar thereto such as R or the like; and $Y_{16}$ is an amino acid K or a hydrophilic amino acid similar thereto such as R or the like.

As used herein, the terms "protein", "polypeptide", "oligopeptide" and "peptide" are interchangeably used in the same context to mean a polymer of amino acids having an arbitrary length. The polymer may be linear, branched or cyclic. The amino acids may be natural, non-natural or modified. The terms can also include complexes of multiple assembled polypeptide chains. The terms also include natural or artificially modified amino acid polymers. Examples of such modifications include disulfide bond formation, glycosylation, lipidation, acetylation, phosphorylation and any other operation or modification (such as binding with a labeling component). The definition also includes, for example, polypeptides containing one or more amino acid analogues (for example, those containing unnatural amino acids), peptide-like compounds (for example, peptoids) and other modified products known in the art.

In the present invention, the "amino acid" may be natural or non-natural as long as the amino acid achieves the object of the present invention.

As used herein, the term "nucleic acid" is used interchangeably with a gene, cDNA, mRNA, oligonucleotide, and polynucleotide. A particular nucleic acid sequence includes "splice variants". Similarly, a particular protein encoded by a nucleic acid includes any other proteins encoded by the splice variant of the nucleic acid. The "splice variant", as it indicates, means a product of a gene by alternative splicing. After transcription, the first nucleic acid transcript can be spliced into a different (other) spliced nucleic acid product encoding different polypeptides. The mechanism of producing the splice variant varies, but it contains alternative splicing of the exon. Different polypeptides derived from the same nucleic acid by read-through transcription are also included in the definition. Any products generated by splicing reaction (including splice products in the recombinant shape) are included in the definition. Alternatively, allelic variants are also included in the range.

As used herein, the terms "polynucleotide", "oligonucleotide" and "nucleic acid" are used in the same meaning, and mean a nucleotide polymer of any length. The term also includes "oligonucleotide derivatives" or "polynucleotide derivatives". The "oligonucleotide derivatives" or the "polynucleotide derivatives" refer to oligonucleotides or polynucleotides containing a nucleotide derivative or a nucleotide bond different from a normal bond. These terms are used interchangeably. Specific examples of the oligonucleotide include 2'-O-methyl-ribonucleotide, oligonucleotide derivatives in which phosphodiester bonds in the oligonucleotide are converted to phosphorothioate bonds, oligonucleotide derivatives in which N3'-P5' phosphoramidate bonds in the oligonucleotide are converted to phosphorothioate bonds, oligonucleotide derivatives in which ribose-phosphate bonds are converted to peptide-nucleic acid bonds, oligonucleotide derivatives in which uracils of the oligonucleotide are substituted by C-5 propynyl uracils, oligonucleotide derivatives in which uracils of the oligonucleotide are substituted by C-5 thiazole uracils, oligonucleotide derivatives in which uracils of the oligonucleotide are substituted by C-5 propynylcytosine, oligonucleotide derivatives in which cytosines in the oligonucleotide are substituted by phenoxazine-modified cytosines (phenoxazine-modified cytosine), oligonucleotide derivatives in which riboses in the DNA are substituted by 2'-O-propylribose, and oligonucleotide derivatives in which riboses in the oligonucleotide are substituted by 2'-methoxyethoxyriboses. A particular nucleic acid sequence includes, similarly to a sequence explicitly indicated, its conservatively modified variants (for example, degenerate codon substitution derivatives) and its complementary sequences, unless specified otherwise. Specifically, degenerate codon substitution derivatives are prepared by forming a sequence in which the 3rd positions of one or more selected (or, all) codons are replaced with mixed bases and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)).

In the present invention, the "nucleotide" may be natural or non-natural as long as it retains its desirable function.

As used herein, the term "search" means the act of identifying other nucleic acid sequences having a particular function and/or property by using a nucleic acid sequence by means of an electronic, biological or other method. Electronic retrieval methods include, but are not limited to, BLAST (Altschul et al., J. Mol. Biol. 215: 403-410 (1990)), FASTA (Pearson and Lipman, Proc. Natl. Acad. Sci., USA 85: 2444-2448 (1988)), Smith and Waterman method (Smith and Waterman, J. Mol. Biol. 147: 195-197 (1981)), and Needleman and Wunsch method (Needleman and Wunsch, J. Mol. Biol. 48: 443-453 (1970)). Biological retrieval methods include, but are not limited to, stringent hybridization, macroarray by using for example a nylon membrane carrying genome DNA attached thereto or microarray by using a glass plate carrying the same (microarray assay), PCR, and in-situ hybridization. In the present invention, it is intended that the corresponding genes identified by the electronic or biological retrieval methods above are also included in the genes for use in the present invention (for example, Hsp90).

In the present invention, a nucleic acid sequence hybridizing to a particular gene can be used as long as it retains its function. Here, the "stringent condition" for hybridization means a condition at which the complementary chain of a nucleotide chain having a similarity or homology with the target sequence can hybridize to the target sequence preferentially and the complementary chain of a nucleotide chain having no similarity or homology does not substantially hybridize. The "complementary chain" to a nucleic acid sequence is a nucleotide sequence that binds to the sequence, based on the hydrogen bonds formed between the bases in the nucleic acid (for example, T to A and C to G). The stringent condition is dependent on the sequence and varies under various situations. Longer sequences hybridize specifically at higher temperatures. Generally, the temperature of the stringent condition is selected to be about 5° C. lower than the thermal melting temperature (Tm) of a particular sequence at a specified ionic strength and pH. $T_m$ is a temperature at which 50% of the nucleotide complementary to a target sequence hybridizes to the target sequence at equilibrium at a specified ionic strength, pH, and nucleic acid concentration. The "stringent condition" is dependent on the sequence and varies according to various environmental parameters. General indications on nucleic acid hybridization are found in Tijssen (Tijssen (1993), *Laboratory Techniques In Biochemistry And Molecular Biology-Hybridization With Nucleic Acid Probes Part I, Chapter 2*," Overview of principles of hybridization and the strategy of nucleic acid probe assay", Elsevier, New York).

Typically at stringent conditions, the salt concentration is less than about 1.0 M Na$^+$; the Na$^+$ concentration (or other salt) is typically about 0.01 to 1.0 M at a pH of 7.0 to 8.3; and the temperature is at least about 30° C. for short nucleotides (for example, with 10 to 50 nucleotides) and at least about 60° C. for longer nucleotides (for example, with more than 50 nucleotides. Stringent conditions can also be formed by the addition of an instabilizer such as formamide. The stringent condition as used herein is, for example, hybridization in a buffer solution of 50% formamide, 1 M NaCl and 1% SDS (37° C.) and cleaning at 0.1×SSC and 60° C.

As used herein, the "stringent condition for hybridization of polynucleotides" is a condition known by those who are skilled in the art. It is possible to obtain such a polynucleotide by using a polynucleotide selected from the polynucleotides according to the present invention as a probe, for example by a colony-hybridization method, a plaque-hybridization method or a Southern blot hybridization method. Specifically, it means a polynucleotide that can be identified by performing hybridization using a filter carrying a colony- or plaque-derived DNA immobilized thereon in the presence of 0.7 to 1.0 M NaCl at 65° C. and washing the filter by using 0.1× to 2× concentrated SSC (saline-sodium citrate) solution (the composition of the 1× concentrated SSC solution is 150 mM sodium chloride and 15 mM sodium citrate) under the condition of 65° C. The hybridization can be carried out by the methods described in experimental books such as *Molecular Cloning 2nd ed., Current Protocols in Molecular Biology, Supplement* 1 *to* 38, *DNA Cloning* 1: *Core Techniques, A Practical Approach, Second Edition*, Oxford University Press (1995). Preferably, sequences containing only A sequence or T sequence are eliminated from the sequence hybridizing under stringent condition. The "hybridizable polynucleotide" is a polynucleotide that can hybridize with another polynucleotide under the hybridization condition above. Typical examples of hybridizable polynucleotides include polynucleotides having a homology of at least 60% or more with the base sequence of the DNA encoding the polypeptide having an amino acid sequence specifically shown in the present invention, preferably polynucleotides having a homology of 80% or more, polynucleotides having a homology of 90% or more, and more preferably polynucleotides having a homology of 95% or more.

As used herein, amino acids are indicated by their commonly known 3-character symbols or by 1-character symbols as recommended by the IUPAC-IUB Biochemical Nomenclature Commission. Nucleotides are also indicated similarly with generally recognized 1-character codes.

As used herein, the "homology" of a gene is the degree of identity between 2 or more gene sequences. Thus, when the homology of two genes is high, the identity or similarity of the sequences is high. It is possible to determine if two kinds of genes have homology, by direct comparison of the sequences or by a hybridization method under a stringent condition in the case of nucleic acid. When two gene sequences are compared directly, if the DNA sequences are identical to each other typically at a extent of at least 50% between the gene sequences, preferably at a extent of at least 70%, more preferably at a extent of at least 80%, 90%, 95%, 96%, 97%, 98% or 99%, these genes have homology.

As used herein, the similarity, identity and homology of an amino acid or nucleic acid sequence is calculated by using a sequence analysis tool BLAST and the default parameters thereof. The identity can be retrieved, for example, by using NCBI's BLAST 2.2.9 (published on May 12, 2004). The identity value used herein is normally a value obtained by using BLAST, that is aligned under the default condition. However, if the value becomes larger when the parameters are altered, the largest value is used as the value of identity. When the identity is evaluated in multiple regions, the largest value is used as the value of identity.

As used herein, the "corresponding" gene is a gene in a species that has or is expected to have an action similar to that of a particular gene in the species to be compared, and if there are multiple genes having such an action, it is a gene having the same evolutionary origin. Thus, the gene corresponding to a gene (for example, Hsp90) can be an ortholog of the gene. Thus, the gene corresponding to a human gene can be found in other animals (mouse, rat, pig, rabbit, guinea pig, bovine, sheep and others). Such corresponding genes can be identified by a method known in the art. Thus, for example, the corresponding gene in an animal can be identified by retrieving the databases of the sequences of the animal (for example, mouse, rat, pig, rabbit, guinea pig, bovine, or sheep) by using the sequence of the gene that is the standard for the corresponding gene as a query sequence.

As used herein, the "fragment" refers to a polypeptide or polynucleotide having a sequence length of 1 to n−1 when there is a polypeptide or polynucleotide (having a length of n). The length of the fragment can be altered properly according to its application, and for example, the shortest length, in the case of a polypeptide, is 3, 4, 5, 6, 7, 8, 9, 10, 15, 20, 25, 30, 40, 50, or more, and the length not specifically mentioned above (for example, 11 or more) can also be suitable as the shortest length. Alternatively in the case of a polynucleotide, it is, for example, 5, 6, 7, 8, 9, 10, 15, 20, 25, 30, 40, 50, 75, 100 or more, and the length not specifically mentioned above (for example, 11 or more) can also be suitable as the shortest length. As used herein, the length of polypeptide or polynucleotide can be indicated by the number of amino acid or nucleic acids, as described above, but the number described above is not absolute and the number indicated as the longest or shortest value above is intended to include the numbers in the range of several-unit shorter and longer (or for example 10% more or less) as long as the present invention has the same function. In order to indicate such intentions, a term "about" may be used before the number as used herein. However as used herein, it will be understood that the presence or absence of the term "about" has no influence on the interpretation of the number. The length of a fragment useful as used herein can be determined by whether the fragment has at least one of the functions among the functions of the full-length protein used as the standard for the fragment.

As used herein, a "variant", "variant sequence" or "analog" refers to a derivative of a polypeptide or a polynucleotide, in which a part of it is altered. Such variants include substitution variants, addition variants, deletion variants, truncated variants, and allelic variants. Allelic genes (alleles) are genetic variants that belong to the same gene locus but are different from each other. Thus, an "allelic variant" is a variant allelic to a gene. The "species homolog or homolog" is a species homologous with a gene at the amino acid or nucleotide level at a favorable homology (preferably, 60% or more, more preferably 80% or more, 85% or more, 90% or more, 95% or more). The method of obtaining such a species homolog is apparent from the description as used herein.

In the present invention, for the production of a polypeptide that is functionally equivalent, amino acids may not be only substituted but can also be added, deleted, or modified. Amino acid substitution means substitution of one or more, for example 1 to 10, preferably 1 to 5, more preferably 1 to 3 amino acids of the original peptide. Amino acid addition means an addition of one or more, for example 1 to 10, preferably 1 to 5, more preferably 1 to 3 amino acids to an original peptide chain. Amino acid deletion means a deletion of one or more, for example 1 to 10, preferably 1 to 5, more preferably 1 to 3 amino acids from an original peptide. Amino acid modifications include, but are not limited to, amidation, carboxylation, sulfation, halogenation, alkylation, phosphorylation, hydroxylation, and acylation (for example, acetylation). The amino acids substituted or added may be natural amino acids, non-natural amino acids or amino acid analogues. Natural amino acids are preferable.

These nucleic acids can be prepared by the well known PCR method or by chemical synthesis. These methods may be combined, for example, with a site-specific mutagenesis method, a hybridization method or the like.

As used herein, "substitution, addition and/or deletion" of a polypeptide or polynucleotide refers to substitution, addition and/or deletion of amino acids or the alternatives thereof or nucleotides or the alternatives thereof from an original polypeptide or polynucleotide. The techniques for substitution, addition and/or deletion are well known in the art, and examples of such techniques include site-specific mutagenesis. Changes in the standard nucleic acid molecule or polypeptide can occur at the 5'- or 3'-terminal of the nucleic acid molecule or the amino-terminal site or carboxy-terminal site of the amino acid sequence of the polypeptide or alternatively anywhere at the sites between these terminals, as long as the objective function (for example, binding to TPR domain) is preserved, and these changes may be present separately between residues in the standard sequence. The number of the nucleotides or amino acids substituted, added or deleted may be any number of one or more, and the number may be larger, if the variant after substitution, addition or deletion retains the objective function (for example, binding to TPR domain). The number may be, for example, 1 or more, preferably 20% or less, 15% or less, 10% or less, or 5% or less than the entire length, or alternatively 150 or less, 100 or less, 50 or less, or 25 or less.

(Preparation and Analysis of Peptides)

The peptides of the present invention (for example, chimeric peptide) can be obtained or produced by a method well known in the art (for example, chemical synthesis, general engineering methods described below). For example, peptides that are identical to the part of a peptide containing a desired region or domain or peptides having a desired activity in vitro can be synthesized by using a peptide synthesizer. Peptides can be analyzed by hydrophilicity analysis of the identified hydrophobic and hydrophilic regions of a peptide (see, for example, Hopp and Woods, 1981. Proc. Natl. Acad. Sci. USA 78: 3824 to 3828) and thus, the results are helpful in designing the substances for experimental operation (for example, binding experiment and antibody synthesis). Secondary structure analysis can also be performed for identification of the peptide region for establishing a particular structural motif (see, for example, Chou and Fasman, 1974, Biochem 13: 222 to 223). Operation, translation, estimation of a secondary structure, hydrophilic/hydrophobic profiling, estimation and plotting of an open reading frame and determination of a sequence homology can be achieved by using a computer software program available in the art. Examples of other structural analysis methods include X-ray crystal analysis (see, for example, Engstrom, 1974. Biochem Exp Biol 11: 7 to 13) and mass spectrometry and gas chromatography (see, for example, METHODS IN PROTEIN SCIENCE, 1997. J. Wiley and Sons, New York, N.Y.), and computer modeling (see, for example, Fletterick and Zoller, Ed., 1986. Computer Graphics and Molecular Modeling: CURRENT COMMUNICATION IN MOLECULAR BIOLOGY, Cold Spring Harbor Laboratory Press, Cold Spring Harbor, N.Y.) can also be used.

The present invention also relates to a nucleic acid encoding the peptide according to the present invention, containing an L-amino acid. The suitable supply source of the nucleic acid encoding the peptide according to the present invention includes human genome sequences. The other supply sources include rat genome sequences, and the protein sequences which can be obtained respectively from GenBank, and the entirety thereof is herein incorporated by reference. Peptide-encoding nucleic acids can be obtained by a method known in the art (for example, PCR amplification by using a synthetic primer hybridizable to the 3'- or 5'-terminal of sequence and/or cloning from a genome library by using a cDNA or an oligonucleotide sequence specific to a particular gene sequence).

For the expression of a variant peptide, a nucleic acid containing all or part of the nucleotide sequence encoding the peptide can be inserted into a suitable expression vector (i.e., vector containing elements needed for transcription and translation of the inserted peptide coding sequence). In some embodiments, the regulatory element is foreign (i.e., not the native gene promoter). Alternatively, the transcription signal and translation signal needed can be provided from a native promoter for a gene and/or its neighboring region. Various host vector systems can be used for expression of the peptide-encoding sequence. Examples thereof include, but are not limited to, (i) mammalian cell systems infected for example with vaccinia virus or adenovirus; (ii) insect cell systems infected for example with baculovirus; (iii) Yeasts containing a yeast vector and (iv) bacteria transformed with a bacteriophage DNA, a plasmid DNA or a cosmid DNA. Depending on the host cell system used, any one of the multiple suitable transcription and translation elements can be used.

As the promoter/enhancer sequence in the expression vector, regulatory sequence of a plant, animal, insect, or fungus provided herein may be used in the present invention. For example, the promoter/enhancer element for use may be that (for example, GAL4 promoter, alcohol dehydrogenase promoter, phosphoglycerol kinase promoter or alkaline phosphatase promoter) of yeast and other fungi. Examples of the expression vectors or the derivatives thereof include human or animal viruses (for example, vaccinia virus or adenovirus); insect viruses (for example, baculovirus); yeast vectors; bacteriophage vectors (for example, λ phage); plasmid vectors and cosmid vectors.

The host cell strain may regulate the expression of the inserted objective sequence or modify or process the expressed peptide that is encoded by the sequence by a desired particular mean. In addition, expression by a particular promoter can be accelerated in the presence of a particular inducer in the selected host cell strain, thus making the control of expression of generally designed peptides easier. Further, different host cells have particular characteristic mechanisms respectively in translation processes and post-translational processes and also modifications of the expressed peptide (such as glycosylation and phosphorylation). Thus, a suitable cell strain or a host cell system can be selected to ensure desired modification and processing of foreign peptides. For example, peptide expression in bacterial systems can be used for the production of an unglycosylated core peptide, while expression in mammalian cells assures "native" glycosylation of foreign peptides.

Derivatives, fragments, homologues, analogues and mutants of peptides and also nucleic acids encoding these peptides are included. As for nucleic acid, the derivative, fragment or analog provided herein is defined by a sequence of at least 6 (neighboring) nucleic acids, and the nucleic acid has a length sufficient for specific hybridization. As for amino acid, the derivative, fragment or analog provided herein is defined as a sequence of at least 4 (neighboring) amino acids and it has a length sufficient for making an epitope that can be recognize specifically.

In designing a variant, a similar cell-penetrating peptide can be designed, based on the information on the sequence of other TPR domains described in the literature of Scheufler et al., Cell 101, 199-210 (2000). Examples of modifications include conservative substitution, but are not limited thereto.

In addition, the cell-penetrating peptide can also be modified, based on the description of the present description with reference to conventional findings. For example, Daniele Derossi et al., The Journal of Biological Chemistry Vol. 271, No. 30, Issue of July 26, pp. 18188-18193, 1996 provides the findings concerning Antp on its mechanism and the variants with some mutation. The literature also describes the sites important for cell penetration, which can be used for reference in producing the variants and analogues of the present invention, and the literature is herein fully incorporated by reference in its entirety.

Other literatures, including Genevie Ave Dom et al., Nucleic Acids Research, 2003, Vol. 31, No. 2, 556-561; Wenyi Zhang and Steven O, Smith, Biochemistry 2005, 44, 10110-10118; and Isabelle Le Roux, et al., Proc. Natl. Acad. Sci. USA Vol. 90, pp. 9120-9124, October 1993, also provide information on cell penetration mechanisms and mutations, and these literatures can also be used for reference in the production of variants and analogues of the present invention, and these literatures are herein fully incorporated by reference in its entirety.

(Pharmaceuticals)

The substance according to the present invention or the pharmaceutically allowable salt or solvate within the scope of the present invention can be administered as it is, but is preferably provided normally as one of the various medicinal preparations. The pharmaceutical formulation can be used for animals and human.

The administration route usable in the present invention is preferably a route most effective for therapy, and examples thereof can include parenteral administration such as intrarectal, intraoral, subcutaneous, intramuscular or intravenous administration. The forms of the medicine administered include capsules, tablets, granules, powders, syrups, emulsions, suppositories, and injections. Liquid preparations suitable for oral administration, such as emulsions and syrups, can be produced, for example, by using water, sugars such as sucrose, sorbitol, and fructose, glycols such as polyethylene glycol and propylene glycol, oils such as benne oil, olive oil, and soy bean oil, antiseptics such as p-hydroxybenzoic esters, and flavors such as strawberry flavor and peppermint. Alternatively, capsules, tablets, powders, granules and other preparations can be produced by using diluents such as lactose, glucose, sucrose, and mannitol, disintegrants such as starch and sodium alginate, lubricants such as magnesium stearate and talc, binders such as polyvinyl alcohol, hydroxypropylcellulose, and gelatin, surfactants such as fatty acid esters, and plasticizers such as glycerol.

The preparation utilizable in the present invention is suited for parenteral administration is preferably an active compound-containing sterile aqueous preparation that is isotonic with the blood of the recipient. For example in the case of injections, an injection solution is prepared by using a carrier such as a salt solution, a glucose solution or a mixture of salt water and a glucose solution.

The local administration preparation utilizable in the present invention is prepared by dissolving or suspending an active compound in one or more media, such as mineral oil, petroleum oil, and polyvalent alcohols, or in other base substances used in local medicinal preparations. Preparations for enteral administration utilized in the present invention are prepared by using a common carrier, such as cacao oil, hydrogenated fat or hydrogenated fat carboxylic acid, and supplied as a suppository.

The parenteral agents in the present invention can contain one or more auxiliary components selected from the glycols, oils, flavors, antiseptics (including antioxidants), diluents, disintegrants, lubricants, binders, surfactants, and plasticizers exemplified above for oral agents.

The effective dosage and the administration frequency of the compound according to the present invention or the pharmaceutically acceptable salt or solvate thereof may vary depending on the administration form, the age and body weight of the patient and the nature and severity of the symptom to be treated, but normally, the dosage is usually 0.01 to 1000 mg/person per day, preferably 5 to 500 mg/person, and the administration frequency is once a day or several times a day if the medicine is divided.

The present invention also relates to a system, an apparatus or a kit for production of the pharmaceutical composition according to the present invention. Constituents for such a system, apparatus or kit are known in the art, and such a system, an apparatus, or a kit can be designed properly by those who are skilled in the art.

The present invention also relates to a system, an apparatus or a kit using a prodrug such as a compound according to the present invention or a pharmaceutically acceptable salt, solvate or hydrate thereof. Constituents for such a system, an apparatus, or a kit are known in the art, and such a system, an apparatus, or a kit can be designed properly by those who are skilled in the art.

(DDS)

The "delivery agent" or "delivery medium", as used herein, refers to a carrier (vehicle) delivering an objective substance. When the delivered substance is a drug, it is called a "drug delivery medium". The drug delivery systems (DDS) can be grouped into absorption-regulated DDSs, release-regulated DDSs and target-specific DDSs. An ideal DDS is a system delivering a drug to "a site in the body in need", "in an amount needed", and "at the time needed. Targeted DDSs are grouped into passive targeted DDSs and active targeted DDSs. The former is a method of regulating the behavior in the body, by using the physicochemical properties of the carrier (drug-delivering agent) such as particle diameter and hydrophilicity. The latter is a method of regulating the specificity to the target tissue aggressively by adding a special mechanism to the method above, and an example thereof is a method of using a carrier carrying a bound antibody (for example, TPR-binding peptide according to the present invention) having a function to recognize specifically the target molecule in the specific cells constituting the targeted organ, which is sometimes called "missile drug".

The "drug delivery medium", as used herein, refers to a vehicle for delivery of a desired drug.

The "objective substance", as used herein, refers to a substance desirably delivered into cells particularly by the delivery medium.

The "liposome," as used herein, usually refers to a closed vesicle composed of a lipid layer collected in the membrane shape and an aqueous layer enclosed therein. The lipid layer normally contains phospholipids and also cholesterol, glycolipid, and others additionally. The liposome, closed vesicle internally encapsulating water, can retain, for example, a water-soluble medicine therein. Accordingly, such a liposome has been used for delivery into the cell, a pharmaceutical or a gene that can not penetrate the cell membrane. It has also good biocompatibility and thus is appropriate for use as a new nanoparticle-carrying material for DDS. In the present invention, the liposome may have structural units having an ester bond-forming functional group (e.g., glycolipid, ganglioside, or phosphatidylglycerol) or structural units having a peptide bond-forming functional group (e.g., phosphatidylethanolamine), which are prepared by using a linker, a crosslinking agent or the like as needed, for giving a modifying group.

The liposome can be prepared by any one of the methods known in the art. Among them, is, for example, the cholic acid dialysis method. In the cholic acid dialysis method, a) a mixed micelle of a lipid and a surfactant is prepared, and b) liposome is produced by dialysis of the mixed micelle. In a preferable embodiment of the carbohydrate-chain liposome used in the present invention, a protein is used favorably as the linker, and a glycoprotein consisting of a protein and a carbohydrate chain bound thereto is coupled with the liposome in the following two-phase reaction: a) periodate oxidation of the ganglioside region on the liposomal membrane, and b) coupling of the oxidized liposome with the glycoprotein in a reductive amination reaction. In this way, it is possible to bind a glycoprotein having a desired carbohydrate chain to the liposome and to obtain various kinds of glycoprotein-liposome conjugates having the desired carbohydrate chain. It is very important to study the particle diameter for distribution, for examination of the purity and stability of the liposome. The methods for use include gel filtration chromatography (GPC), scanning electron microscopy (SEM), and dynamic light scattering (DLS).

The "linker", as used herein, refers to a molecule mediating association between a surface-binding molecule (for example, Hsp90 TPR-binding peptide) and the liposome surface. In the carbohydrate chain-modified liposome used in the present invention, a peptide may be bound to the liposome surface via a linker. The linker can be selected properly by those who are skilled in the art, but a biocompatible linker is preferable and a pharmaceutically acceptable linker is more preferable. The "linker protein", as used herein, is a protein, a peptide or a polymer of amino acids among the linker molecules.

The "linker (protein) group", as used herein, refers to the designation of the linker (protein) when it is bound to another group. The linker (protein) group may be monovalent or bivalent, as needed. Examples thereof include mammal-derived protein groups, human-derived protein groups, human serum protein groups, and serum albumin groups. The linker (protein) group is preferably a "human"-derived group. This is because such a group would be highly compatible for human administration. In addition, a protein without immunogenicity is preferable.

The "crosslinking group", as used herein, refers to a group forming a bridge-like chemical bond between molecules of linear polymers. Typically, it is a group acting on a polymer such as lipid, protein, peptide or carbohydrate chain and also on another molecule (for example, lipid, protein, peptide, carbohydrate chain) to form a covalent bond intramolecularly or intermolecularly in the region where there is no covalent bond. The crosslinking group used as used herein varies depending on the target to be crosslinked, and examples thereof include, but are not limited to, aldehydes (such as glutaric aldehyde), carbodiimides, and imide esters. For crosslinking of amino-group-containing substances, use of an aldehyde-containing group, such as glutaric aldehyde, is possible.

The "biocompatible" or "biocompatibility", as used herein, refers to a property of being compatible with body tissues or organs without generating toxicity, immune reaction, damage or the like. Examples of the biocompatible buffer solutions include, but are not limited to, phosphate-buffered physiological saline (PBS), physiological saline, tris buffer solution, carbonate buffer solution (CBS), tris(hydroxymethyl)methylaminopropanesulfonate buffer solution (TAPS), 2-[4-(2-hydroxylethyl)-1-piperadinyl]ethanesulfonic acid (HEPES), other Good's buffer solutions (for example, 2-morpholinoethanesulfonic acid monohydrate (MES), bis(2-hydroxyethyl)imino tris(hydroxymethyl)methane (Bis-tris), N-(2-acetamido)iminodiacetic acid (ADA), 1,3-bis[tris(hydroxymethyl)methylamino]propane (Bis-trispropane), piperazine-1,4-bis(2-ethanesulfonic acid) (PIPES), N-(2-acetamide)-2-aminoethanesulfonic acid (ACES), cholamine chloride, N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), N-(2-hydroxyethyl) piperazine-N'-3-propanesulfonic acid (HEPPS), N-[tris(hydroxymethyl)methyl]glycine (Tricine), aminoacetamide (glycinamide), N,N-bis(2-hydroxyethyl)glycine (Bicine), N-cyclohexyl-2-aminoethanesulfonic acid (CHES), and N-cyclohexyl-3-aminopropanesulfonic acid (CAPS)).

As described above, the present invention provides a delivery agent of delivering an objective substance containing an Hsp90 TPR domain-binding peptide to cancer cells. The objective substance may or may not be bound to the Hsp90 TPR domain-binding peptide. If it is bound, the compound is a fusion substance, which is called a chimeric peptide when it is a peptide. The chimeric peptide according to the present invention may be in the form of this embodiment. Such a substance may form a composite agent with the medium (vehicle). Liposome may be used as the medium, and the objective substance may be present outside the liposome or encompassed in the liposome.

Specific protocols for the experimental system used for the demonstration of the concept of utilizing liposome in DDS will be described below.

It is possible to determine if the TPR peptide designed in the present invention has a cell-killing effect, when it is introduced into cells, by forming a liposome by mixing a TPR peptide or a TPR scramble peptide with a commercially available transfection reagent (such as Profect-P2 (Nacalai Tesque, Inc.) or Lipofectamine (trademark) LTX (Invitrogen))(for example, left at room temperature for 20 minutes), adding the complex to cancer cells (for example, Caki-1 (kidney cancer)), then, measuring the survival rate of the cells by using a WST-8 solution (Cell Count Reagent SF; Nacalai Tesque, Inc.), and comparing the results with those obtained in the case when the TPR scramble peptide is added.

The reference literatures such as scientific papers, patents, and patent applications cited herein are fully incorporated by reference in its entirety to the degree of identicalness to that of the specific description.

Hereinafter, the present invention will be described with reference to Examples, but the following Examples will be provided only for exemplification. Therefore, the scope of the present invention is not restricted by the embodiments or examples and is restricted only by the claims.

EXAMPLES

Hereinafter, the present invention will be described in more detail with reference to examples, but it will be understood that the technical scope of the present invention is not restricted by these examples and the like. Reagents used in the Examples below can be purchased from Wako Pure Chemical Industries, Sigma-Aldrich and others, and the like unless specified otherwise. In addition, animal tests were conducted according to the standards for humane and ethical treatment of animals specified by Kyoto University.

Example 1

Production of Hsp90 TPR-Binding Peptide-Antp Chimeric Peptide and Measurement of Biological Activity It was examined whether the chimeric peptide according to the present invention has a cell-killing effect and an anti-tumor effect to solid cancer cell strains.

(Materials and Methods)

(Cell Strains)

Human breast cancer cell strains (BT-20 and T47D), lung cancer cell strains (H322 and H460), a prostate cancer cell strain (LNCap), a neuroglioma cell strain (U251), a kidney cancer cell strain (Caki-1) and a lung fibroblast cell strain (MRC-5) were purchased from American Type Culture Collection (Manassas, Va.). A human pancreatic cancer cell strain (BXPC-3) was purchased from European Collection of Cell Cultures (ECACC; Salisbury, Wiltshire, UK). A human embryonic kidney cell strain (HEK293) was purchased from RIKEN Cell Bank (Tsukuba, Japan). The cells were cultured in RPMI 1640 (BT-20, T47D, H322, H460, LNCap, U251 and BXPC-3), MEM (MARC-5) or D-MEM (HEK293, Caki-1) each containing 10% FBS (BioWest, Miami, Fla.), 100 μg/ml penicillin and 100 μg/ml streptomycin (Nacalai Tesque, Inc. Kyoto, Japan).

(Peptides)

The following peptide was purchased from Invitrogen, Carlsbad, Calif. or synthesized by using a peptide synthesizer (for example, Applied Biosystems: Model 433A peptide synthesizer).

```
                              (Antp-TPR wild; SEQ ID No. 9)
1. chimeric peptide: RQIKIWFQNRRMKWKK-KAYARIGNSYFK
```

Here, RQIKIWFQNRRMKWKK (SEQ ID NO: 5) may be referred to as Antennapedia homeodomain sequence (Antp) in the present specification.

In addition to the chimeric peptide above, various variant peptides were prepared.

The peptides synthesized were the followings:

```
                                          (SEQ ID No. 42)
2. chimeric peptide: RQIKIWFQNRRMKWKK-KAYAR (TPR peptide; SEQ ID No. 4)
3. peptide: KAYARIGNSYFK (Mutant 1; SEQ ID No. 44)
4. chimeric peptide: RQIKIWFQNRRMKWKK-
KAYAAAGNSYTFK
and
                                      (Mutant 2; SEQ ID No. 45)
5. chimeric peptide: RQIKIWFQNRRMKWKK-KAYARIGNSGGG.
```

Additionally, the following peptides were also synthesized:

```
                              (Antp-TPR K1R; SEQ ID No. 10)
RQIKIWFQNRRMKWKKRAYARIGNSYFK, (Antp-TPR K1A; SEQ ID No. 11)
RQIKIWFQNRRMKWKKAAYARIGNSYFK, (Antp-TPR A2G; SEQ ID No. 12)
RQIKIWFQNRRMKWKKKGYARIGNSYFK, (Antp-TPR Y3L; SEQ ID No. 13)
RQIKIWFQNRRMKWKKKALARIGNSYFK, (Antp-TPR A4G; SEQ ID No. 14)
RQIKIWFQNRRMKWKKKAYGRIGNSYFK, (Antp-TPR R5K; SEQ ID No. 15)
RQIKIWFQNRRMKWKKKAYAKIGNSYFK, (Antp-TPR I6R; SEQ ID No. 16)
RQIKIWFQNRRMKWKKKAYARRGNSYFK, (Antp-TPR G7A; SEQ ID No. 17)
RQIKIWFQNRRMKWKKKAYARIANSYFK, (Antp-TPR N8Q; SEQ ID No. 18)
RQIKIWFQNRRMKWKKKAYARIGQSYFK, (Antp-TPR S9Y; SEQ ID No. 19)
RQIKIWFQNRRMKWKKKAYARIGNYYFK, (Antp-TPR Y10S; SEQ ID No. 20)
RQIKIWFQNRRMKWKKKAYARIGNSSFK, (Antp-TPR F11Y; SEQ ID No. 21)
RQIKIWFQNRRMKWKKKAYARIGNSYYK
and
                              (Antp-TPR K12R; SEQ ID No. 22)
RQIKIWFQNRRMKWKKKAYARIGNSYFR.
```

Additionally, variants concerning cytolysis were also synthesized:

```
                              (AnR1K-TPR; SEQ ID No. 23)
KQIKIWFQNRRMKWKKKAYARIGNSYFK, (AnQ2N-TPR; SEQ ID No. 24)
RNIKIWFQNRRMKWKKKAYARIGNSYFK, (AnI3L-TPR; SEQ ID No. 25)
RQLKIWFQNRRMKWKKKAYARIGNSYFK, (AnK4R-TPR; SEQ ID No. 26)
RQIRIWFQNRRMKWKKKAYARIGNSYFK, (AnI5L-TPR; SEQ ID No. 27)
RQIKLWFQNRRMKWKKKAYARIGNSYFK, (AnW6Y-TPR; SEQ ID No. 28)
RQIKIYFQNRRMKWKKKAYARIGNSYFK, (AnF7Y-TPR; SEQ ID No. 29)
RQIKIWYQNRRMKWKKKAYARIGNSYFK, (AnQ8N-TPR; SEQ ID No. 30)
RQIKIWFNNRRMKWKKKAYARIGNSYFK, (AnN9Q-TPR; SEQ ID No. 31)
RQIKIWFQQRRMKWKKKAYARIGNSYFK, (AnR10K-TPR; SEQ ID No. 32)
RQIKIWFQNKRMKWKKKAYARIGNSYFK, (AnR11K-TPR; SEQ ID No. 33)
RQIKIWFQNRKMKWKKKAYARIGNSYFK, (AnM12C-TPR; SEQ ID No. 34)
RQIKIWFQNRRCKWKKKAYARIGNSYFK, (AnK13R-TPR; SEQ ID No. 35)
RQIKIWFQNRRMRWKKKAYARIGNSYFK, (AnW14Y-TPR; SEQ ID No. 36)
RQIKIWFQNRRMKYKKKAYARIGNSYFK, (AnK15R-TPR; SEQ ID No. 37)
RQIKIWFQNRRMKWRKKAYARIGNSYFK, (AnK16R-TPR; SEQ ID No. 38)
RQIKIWFQNRRMKWKRKAYARIGNSYFK, (Antp-TPR slong; SEQ ID No. 39)
RQIKIWFQNRRMKWKKRQIAKAYARIGNSYFK
and
                                      (R11-TPR; SEQ ID No. 40)
RRRRRRRRRRRKAYARIGNSYFK.
```

These peptides were chemically synthesized, purified by high-performance liquid chromatography and then dissolved in water.

(Cell Viability Assay)

A total of 3×10³ cells were inoculated per well on a 96 well plate and cultured in a medium containing 10% FBS for 24 hours, and incubated with 100 μl of a peptide having a gradual increase in concentration at 37° C. for 48 to 72 hours. The survival rate of the cells was measured by using WST-8 solution (Cell Count Reagent SF; Nacalai Tesque, Inc.).

(Flow Cytometry Assay)

For examining whether the Antp-TPR peptide induces apoptosis of cancer cells, a flow cytometry assay was performed by using double staining with annexin V or caspase 3,7 and propidium iodide (PI).

(Protocol)

Cancer cells T47D and normal cells HEK293T were cultured in their respective media on a 6-well dish (Nunc™) for 24 hours and then, 68 µM of the Antp-TPR chimeric peptide was added thereto, and the mixture was cultured additionally for 24 hours. After the culture, each cell suspension was subjected to propidium iodide (PI) staining, annexin V labeling (both, Wako) or caspase 3,7 labeling and subsequently annexin V labeled or caspase 3,7 labeled and PI stained cells were analyzed simultaneously by multiparametric flow cytometry.

(Results)

Figure 9:
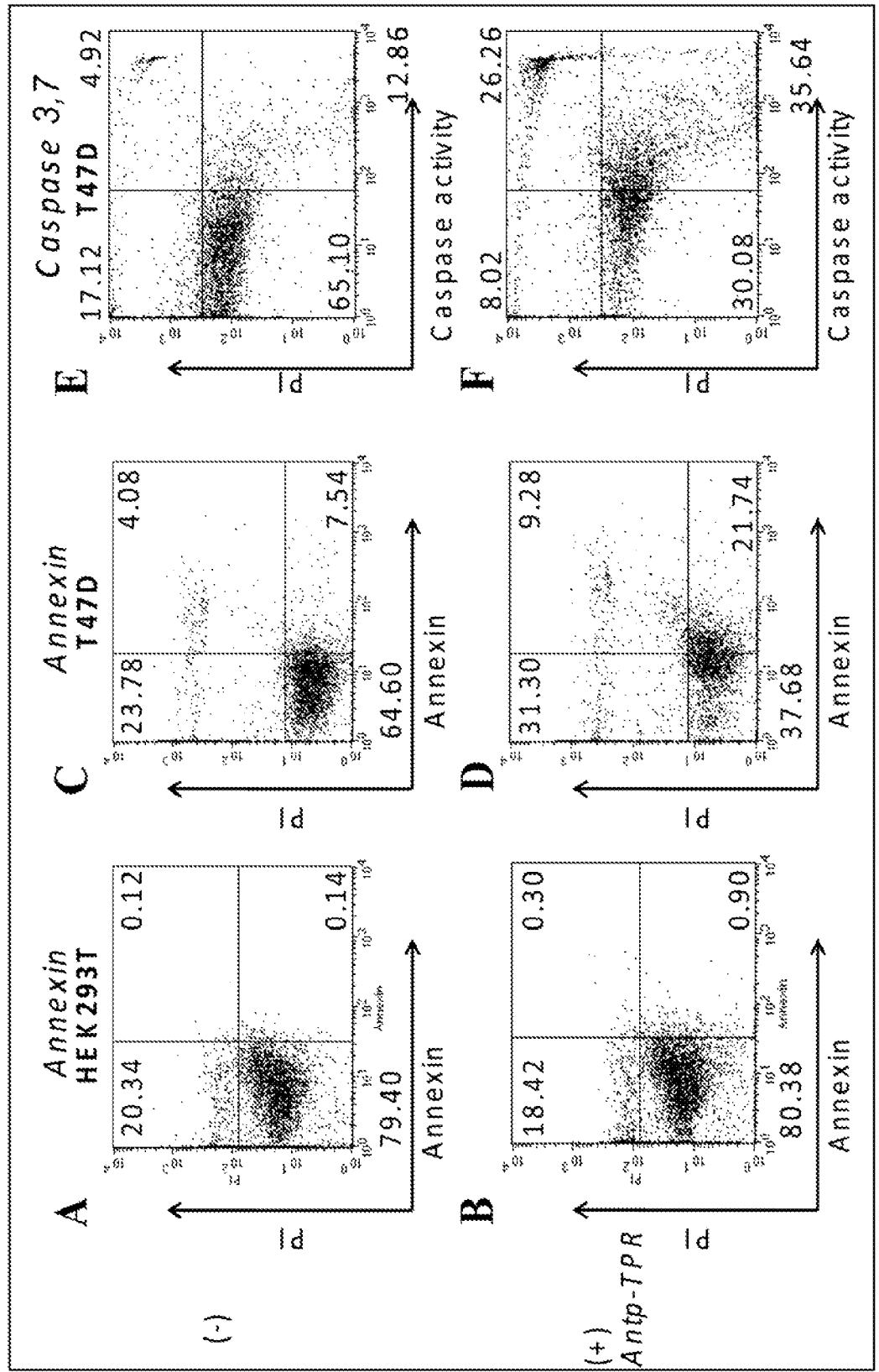
FIG. 9 shows the results obtained by examining the cancer cell-killing effect of the hybrid Antp-TPR peptide by using FACS. Cancer cell T47D and normal cell HEK293T were cultured in their respective media on a 6-well dish (Nunc™) for 24 hours, and 68 µM of the Antp-TPR chimeric peptide was added thereto and the mixture was cultured additionally for 24 hours. After culture, respective cell suspensions were subjected to propidium iodide (PI) staining (A to F), annexin V labeling (A to D) (all, obtained from Wako), or caspase 3,7 labeling (E,F) (obtained from Immunochemistry Technologies), and annexin V labeling or caspase 3,7 activity and PI staining were analyzed simultaneously by multiparametric flow cytometry. The percentage of the cells present is shown in each quarter panel. Graph A shows the case where the peptide is not added to normal HEK293T cells. Graph B shows the case where 68 µM of the Antp-TPR peptide was added to normal HEK293T cells. C and E show the cases when the peptide was not added to breast cancer cell T47D. D and F show the cases when 68 µM of the Antp-TPR peptide was added to breast cancer T47D cells. There is no activity when the Antp-TPR peptide is added to normal cell HEK293T, but there is an observable increase in annexin V-positive or caspase 3,7-positive cell population when the peptide is added to cancer cell T47D. The results indicated that the peptide added induces death of cancer cells specifically by apoptotic mechanism.

Results are shown in FIG. 9. Addition of the Antp-TPR peptide to the normal cells HEK293T exerted no influence, but the addition of the peptide to the cancer cells T47D resulted in an increase of annexin V-positive or caspase 3,7-positive cell populations.

Accordingly, the results indicated that the peptide added induces death in cancer cells specifically via an apoptotic mechanism.

Specifically, there is no influence observed even if the Antp-TPR peptide was added to the normal cells HEK293T, while, if the peptide was added to the cancer cells T47D, an increase in annexin V-positive or caspase 3,7-positive cells is observed. Accordingly, the results show that the cancer cells T47D are killed by the addition of the peptide or the killed cells undergo apoptosis. In any case, the peptide of the present invention induces an increase in cell death, and probably, it is indicated that the cell death is generated by apoptotic mechanism, indicating that the present invention is a treatment method more favorable than conventional methods.

(Interaction of Biological Molecules)

A surface plasmon resonance (SPR) experiment was performed by using BIACORE biosensor system 3000 (BIACORE Inc, Uppsala, Sweden). About 5000 RU of Hsp90 was immobilized on the surface of a CM5 sensor chip according to the manufacturer's manual by the activated chemistry of N-hydroxysuccinimide and N-ethyl-N'-(dimethylaminopropyl)carbodiimide. Unreacted carboxymethyl groups on the sensor chip without immobilization were blocked with ethanolamine, as a control for non-specific binding. For preventing non-specific binding during assay, a HBS buffer solution (0.01 M HEPES, 0.15 M NaCl, 0.005% Tween 20, 3 mM EDTA [pH 7.4]) was used as an electrophoresis buffer solution. The interaction of the recombinant human Hsp90 with a TPR-binding domain-lytic peptide chimeric peptide was analyzed in the following manner: as described above, about 5000 RU of Hsp90 was immobilized onto a CM5 sensor chip and then, peptides at various concentrations were injected onto the sensor chip. The concentration of the protein used in each of these experiments was determined by the Bradford method (Bradford MM. A rapid and sensitive method for the quantitation of microgram quantities of protein utilizing the principle of protein-dye binding. Anal Biochem 1976; 72: 248-54). Data analysis was made by using BIA evaluation ver. 3.2 software (BIACORE).

(Western Blotting Concerning Cells Observed with Cell Killing Effect)

Cancer cells having cell killing effect and normal cells were cultured in their respective media on a 6-well (Nunc™) plate for 24 hours; the supernatant was then washed with phosphate-buffered buffer solution (PBS) at least twice; Cell lysis buffer (Promega) was then added to the respective wells in an amount of 300 µl for lysis of the cells, to give a total cell-extraction protein (total protein). The extracted solution was separated by SDS-PAGE and the proteins were transferred onto a membrane by a semi-dry method. A 10% skim milk solution was prepared by using a phosphate-buffered buffer solution (PBS); after blocking for 1 hour and 30 minutes, the mixture was allowed to react in a solution (Stressgen Bioreagents, SIGMA) containing antibodies to Hsp90, Hsp70, survivin and actin overnight; and then, the solution was allowed to react with an secondary antibody (GE Healthcare) and chemically stained with ECL kit (GE Health science); and the bands were detected in Las3000 system.

(Experimental Results Concerning Binding to Hsp90)

The wild-type sequence of the newly designed peptide is RQIKIWFQNRRMKWKK-KAYARIGNSYFK (SEQ ID NO: 9). The N terminal-side peptide is cell-penetrating peptide Antp, while the C-terminal peptide is, as shown in FIG. 1 (A), an Hsp90 TPR-binding peptide which binds to the TPR peptide (sequence of a partial region of the helix important for binding to C-terminal of Hsp90, which is present in the Hop's TPR2A domain).

The region essential for binding with Hsp90 was analyzed by using a spatial structure-displaying software (Ras Mol ver 2.7 for Macintosh (free software, http://www.openrasmol.org/). FIG. 1(B) is a view of the spatial structure of the complex reported between the Hop's TPR domain and the Hsp90's C-terminal sequence MEEVD (SEQ ID NO: 64) (center, white). In Fig. (B) of the spatial structure, the helix (indicated by arrow) important for binding with Hsp90 is the region used for designation this time, and FIG. 1(C) is a view of the spatial structure of the predicted complex formed between the peptide and the Hsp90's C-terminal sequence MEEVD (SEQ ID NO: 64) (right). The helix in the region shown in the figure displayed by the software was predicted to bind to Hsp90 sufficiently.

Figure 2:
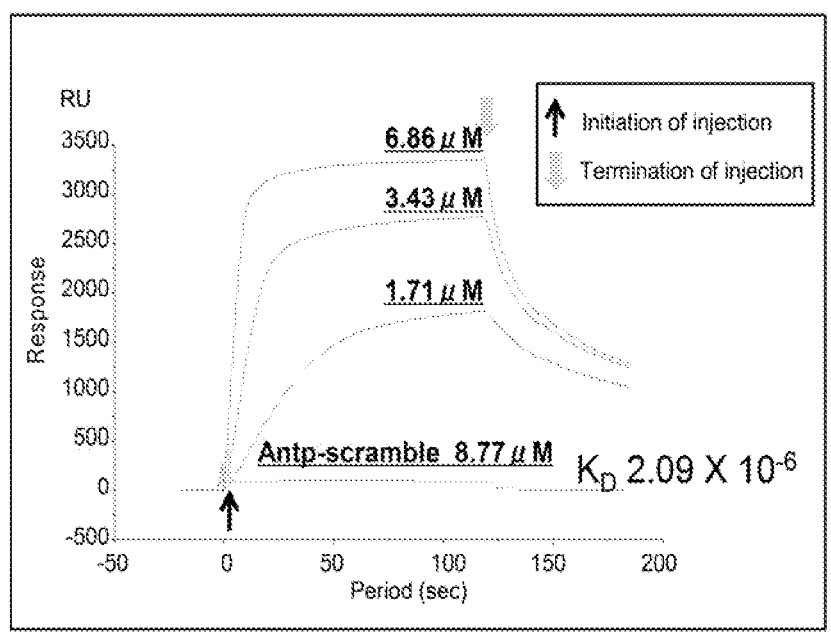
FIG. 2 shows the results obtained by analysis of the interaction between Hsp90 immobilized on a sensor chip and a newly designed Antp-TPR peptide by using a BIACORE apparatus (biological intermolecular interaction analyzer). As apparent from FIG. 2, it was found that the binding occurs in a manner dependent on the peptide concentration. It was also found that the affinity constant (Kd) was $2.09 \times 10^{-6}$.

FIG. 2 shows the results of analysis of the interaction between Hsp90 which was immobilized onto a sensor chip and a newly designed Antp-TPR peptide by using BIACORE (biological intermolecular interaction analyzer), indicating that the binding occurs in a manner dependent on the peptide concentration. In addition, the affinity constant (Kd) was found to be $2.09 \times 10^{-6}$.

(Results of Cell Viability Assay)

Figure 3:
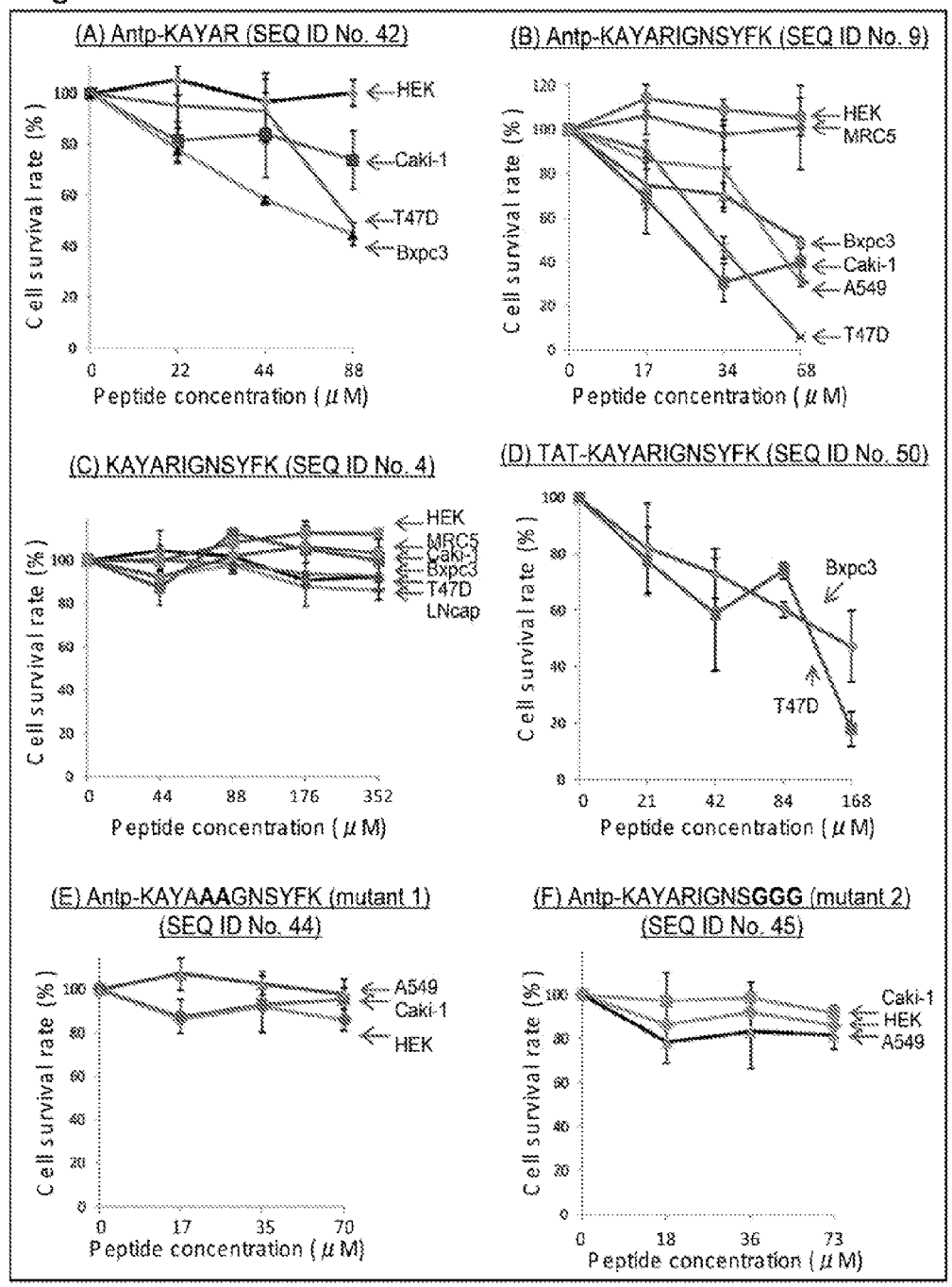
FIG. 3 shows the cytotoxic activity of Antp-TPR and Antp-TPR variant peptides.

FIG. 3 and the following table show the cytotoxic activity of Antp-TPR and Antp-TPR variant peptides as the result.

TABLE 1

| Peptide Concentration (µM) | (A) Antp-KAYAR (SEQ ID No. 42) | | | |
|---|---|---|---|---|
| | Cell Survival Rate (%) | | | |
| | HEK | Caki-1 | Bxpc3 | T47D |
| 0 | 100 | 100 | 100 | 100 |
| [SD] | 0 | 0 | 0 | 0 |
| 22 | 105.20 | 81.29 | 77.99 | 95.44 |
| [SD] | 5.77 | 7.86 | 5.06 | 9.02 |
| 44 | 97.08 | 83.76 | 58.42 | 93.04 |

TABLE 1-continued

| | | | | |
|---|---|---|---|---|
| [SD] | 11.00 | 16.57 | 0.98 | 12.56 |
| 88 | 100.25 | 74.00 | 44.69 | 48.35 |
| [SD] | 5.05 | 11.54 | 4.63 | 8.01 |

(B) Antp-KAYARIGNSYFK (SEQ ID No. 9)

| Peptide Concentration | Cell Survival Rate (%) | | | | | |
|---|---|---|---|---|---|---|
| (μM) | HEK | Caki-1 | BXPC3 | T47D | A549 | MRC5 |
| 0 | 100 | 100 | 100 | 100 | 100 | 100 |
| [SD] | 0 | 0 | 0 | 0 | 0 | 0 |
| 17 | 106.37 | 68.89 | 68.61 | 91.18 | 85.97 | 114.38 |
| [SD] | 8.63 | 16.30 | 10.52 | 3.77 | 4.07 | 5.97 |
| 34 | 97.66 | 30.54 | 53.63 | 46.26 | 82.52 | 109.19 |
| [SD] | 6.84 | 8.79 | 5.75 | 4.94 | 19.73 | 4.79 |
| 68 | 100.85 | 39.94 | 28.48 | 5.80 | 30.69 | 105.69 |
| [SD] | 18.98 | 6.05 | 0.73 | 0.43 | 1.88 | 8.77 |

(C) KAYARIGNSYFK (SEQ ID No. 4)

| Peptide Concentration | Cell Survival Rate (%) | | | | | |
|---|---|---|---|---|---|---|
| (μM) | HEK | Caki-1 | Bxpc3 | T47D | LNcap | MRC5 |
| 0 | 100 | 100 | 100 | 100 | 100 | 100 |
| [SD] | 0 | 0 | 0 | 0 | 0 | 0 |
| 44 | 104.25 | 87.65 | 100.30 | 99.42 | 92.72 | 92.16 |
| [SD] | 9.65 | 8.35 | 1.73 | 7.40 | 7.62 | 3.11 |
| 88 | 101.74 | 112.54 | 98.52 | 108.22 | 97.96 | 101.87 |
| [SD] | 6.46 | 2.14 | 3.16 | 5.48 | 3.76 | 5.21 |
| 176 | 90.75 | 105.00 | 93.70 | 112.77 | 88.22 | 106.63 |
| [SD] | 11.93 | 10.83 | 1.15 | 5.47 | 1.06 | 7.80 |
| 352 | 92.56 | 99.96 | 92.94 | 112.57 | 86.30 | 103.17 |
| [SD] | 7.20 | 9.93 | 7.20 | 1.39 | 4.69 | 2.95 |

(D) TAT-KAYARIGNSYFK (SEQ ID No. 50)

| Peptide Concentration | Cell Survival Rate (%) | |
|---|---|---|
| (μM) | Bxpc3 | T47D |
| 0 | 100 | 100 |
| [SD] | 0 | 0 |
| 21 | 82.25 | 77.68 |
| [SD] | 82.25 | 77.68 |
| 42 | 73.08 | 58.60 |
| [SD] | 73.08 | 58.60 |
| 84 | 60.49 | 74.23 |
| [SD] | 60.49 | 74.23 |
| 168 | 47.24 | 17.92 |
| [SD] | 47.24 | 17.92 |

(E) Antp-KAYAAAGNSYFK (Variant 1)(SEQ ID No. 44)

| Peptide Concentration | Cell Survival Rate (%) | | |
|---|---|---|---|
| (μM) | HEK | Caki-1 | A549 |
| 0 | 100 | 100 | 100 |
| [SD] | 0 | 0 | 0 |
| 17 | 86.28 | 87.43 | 107.14 |
| [SD] | 1.53 | 7.82 | 7.33 |
| 35 | 92.03 | 93.11 | 102.68 |
| [SD] | 1.30 | 13.00 | 5.19 |
| 70 | 85.88 | 95.16 | 97.95 |
| [SD] | 4.96 | 9.47 | 2.94 |

TABLE 1-continued (F) Antp-KAYARIGNSGGG ( variant 2)(SEQ ID No. 45)

| Peptide Concentration | Cell Survival Rate (%) | | |
|---|---|---|---|
| (μM) | HEK | Caki-1 | A549 |
| 0 | 100 | 100 | 100 |
| [SD] | 0 | 0 | 0 |
| 18 | 86.28 | 97.07 | 78.25 |
| [SD] | 1.53 | 12.64 | 9.34 |
| 36 | 92.03 | 98.72 | 82.95 |
| [SD] | 1.30 | 6.96 | 16.53 |
| 73 | 85.88 | 91.62 | 81.50 |
| [SD] | 4.96 | 3.50 | 6.35 |

It was found after studies on the cytotoxic activity of the newly designed peptides, chimeric peptides with cell-penetrating peptide Antp, such as (A) and (B), did not exert influence on normal cells HEK and MRC5, but exerted influence on cancer cells Caki-1 (renal cancer), Bxpc3 (pancreatic cancer), T47D (breast cancer) and A549 (lung cancer), KAYARIGNSYFK (SEQ ID NO: 4), that a sequence elongated from 5 amino acids of KAYAR (SEQ ID NO: 3), has a higher activity, and that (C) only the TPR peptide did not show any cytotoxic activity to any cells. As a result of calculating the $IC_{50}$ value from the data on cytotoxic activity, the combination with cell-penetrating peptide Antp did not exert influence on normal cells, but exerted killing ability only on cancer cells, and it was found that the $IC_{50}$ value in the range of 20 μM to 60 μM exerted influence on cancer cells (Table 1A: inhibition concentration of Antp-TPR peptide ($IC_{50}$)).

TABLE 1A

50% inhibition concentration of Antp-TRP peptide ($IC_{50}$)
Anti-tumor activity, $IC_{50}$ (μM) ± SD

| Cell strains | TPR | Antp-TPR |
|---|---|---|
| Normal cell | | |
| HEK | — | — |
| MRC5 | — | — |
| Breast cancer | | |
| T47D | — | 19.4 ± 11.5 |
| BT20 | — | 32.8 ± 5.5 |
| MDA-MB-231 | — | 56.9 ± 12.3 |
| Pancreatic cancer | | |
| Bxpc3 | — | 39.8 ± 2.2 |
| Kidney cancer | | |
| Caki-1 | — | 43.3 ± 3.0 |
| Lung cancer | | |
| A549 | — | 52.9 ± 2.5 |
| Prostate cancer | | |
| LNcap | — | 49.1 ± 3.0 |
| Stomach cancer | | |
| OE19 | — | 29.9 ± 3.4 |

— indicates no action.

(Test with Variants)

Figure 7:
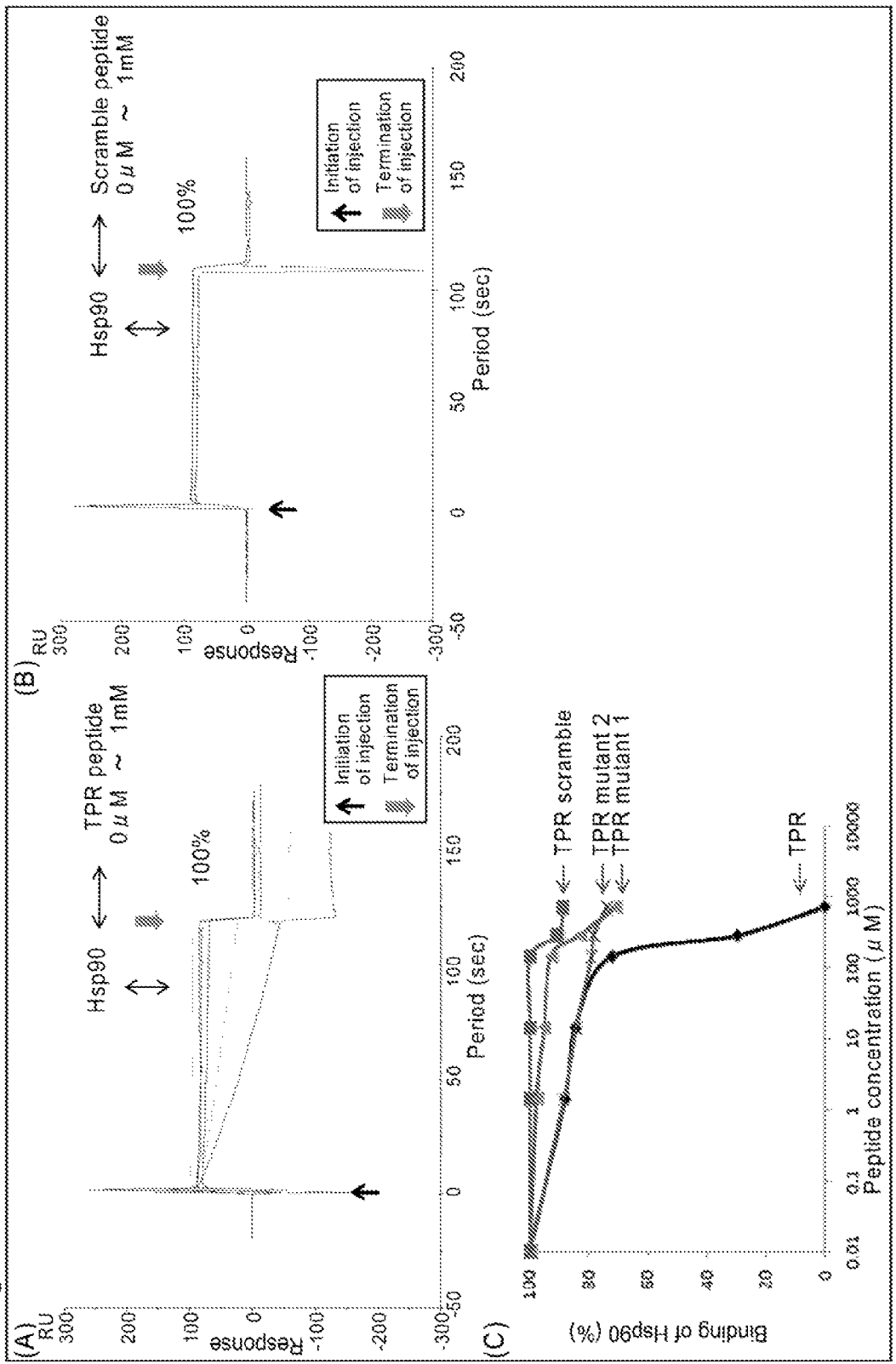
FIG. 7 shows the results obtained by an experiment for confirming inhibitory effect, by pre-mixing Hsp90 and the TPR peptide, TPR scramble, TPR mutant 1, or TPR mutant 2 peptide before adding to a sensor chip containing immobilized TPR2A domain protein, to allow sufficient binding of Hsp90 thereto for determination of the interaction with TPR2A. As shown in the sensorgram and the graph, the TPR peptide exerts an influence on the interaction between Hsp90 and TPR2A when the concentration thereof is increased, while the TPR scramble, TPR mutant 1 or TPR mutant 2 peptide does not inhibit it completely, even when it is added at higher concentration in advance. Graph (A) is the sensorgram obtained when only Hsp90 or a mixture thereof with the TPR peptide at a different concentration (1.4 µM, 14 µM, 140 µM, 280 µM, 700 µM or 1 mM) is added to the immobilized TPR2A, showing that the sensorgram declines, i.e., binding is decreasing, dependently on concentration, when a mixture containing TPR peptide is added dependently on concentration, compared to when only Hsp90 is added. Graph (B) is the sensorgram obtained when the experiment of (A) was repeated similarly by using the TPR scramble peptide, indicating that the sensorgram does not decline, i.e., there is no change in binding, even if the TPR scramble peptide is added at higher concentrations previously. Graph (C) is the sensorgram obtained when the experiment of (A) was repeated similarly by using the TPR scramble (square), TPR mutant 1 (triangle) or TPR mutant 2 (X), showing the relationship between the decrease in binding affinity between TPR2A and Hsp90 and the concentrations of the respective peptides. As shown in the figures above, it was found that peptides other than the TPR peptide (rhomboid) do not inhibit the interaction between TPR2A and Hsp90 completely, even if added at a higher concentration, i.e., at a concentration of 1000 µM.

It was examined whether the TPR peptide designed could compete specifically with the interaction between Hsp90, which is essential for the accurate folding of some carcinogenic protein including survivin in cancer cells, and the Hop's TPR2A domain. FIG. 7 and the following table show the results of a test for confirming inhibitory effect, where Hsp90 is allowed to interact with and bind to each of the following peptides: TPR peptide, TPR scramble, TPR mutant 1 or TPR mutant 2 peptide, before being added to a sensor chip containing immobilized human Hop's TPR2A to assess the interaction of the Hsp90 with TPR2A. As shown in the sensorgram and the graph, the TPR peptide exerts an influence on the interaction between Hsp90 and TPR2A, as the concentration increases (FIGS. 7A and C), but the TPR scramble, TPR mutant 1 or TPR mutant 2 peptide does not inhibit the interaction completely, even if added at higher concentration previously (FIGS. 7B and C).

In addition, both of mutants 1 and 2, which contained mutations in the amino acids that were predicted to be important for examination of the specificity of the TPR peptide, had a cytotoxic activity, but the cytotoxic activity was lower (FIGS. 7A and C).

These results show that the designed TPR peptide is a specific competitive factor that can inhibit the interaction between Hsp90 and the Hop's TPR2A domain and the targeted amino acids in the test with variants are important for the protein interaction.

TABLE 2

| | Binding of Hsp90 (%) | | | |
|---|---|---|---|---|
| Peptide Concentration (μM) | TPR (SEQ ID No. 4) | TPR scramble (SEQ ID No. 72) | TPR mutant 1 (SEQ ID No. 70) | TPR mutant 2 (SEQ ID No. 71) |
| 0 | 100 | 100 | 100 | 100 |
| 1.411 | 88.19 | 100 | 97.75 | 88.52 |
| 14.11 | 84.60 | 100 | 95.20 | 84.43 |
| 141.1 | 72.26 | 100 | 92.84 | 79.30 |
| 282.2 | 29.75 | 90.67 | 83.14 | 78.69 |
| 705.5 | 0 | 88.91 | 71.08 | 74.02 |

(Loss of Hsp90 Client Protein by Antp-TPR Peptide)

The level of the Hsp90 client proteins was examined after the addition of Antp-TPR peptide to cells, showing that a plurality of Hsp client peptides including survivin, CDK4 and Akt were lost in the Antp-TPR-treated T47D cells. In contrast, the Antp-TPR peptide did not exert any influence on the level of Hsp90 itself (FIG. 4(A)). These results show that the Antp-TPR peptide designed, exerts influence on the cell survival pathway of cancer cells, by interfering in a competitive manner with the recruitment of the cochaperone essential for accurate folding of the Hsp90 client protein.

(Amounts of Respective Proteins Expressed)

The amounts of the Hsp90 client proteins expressed in cells having particularly high killing effect were examined by Western blotting, showing that survivin was expressed particularly in a great amount, as shown in FIG. 4(B). It was thus found that the peptide newly designed this time is effective to cancer cells, particularly to those in which the amount of survivin expressed is greater.

In addition, the results of flow cytometry showed that cancer cells treated with the Antp-TPR peptide were annexin V positive and caspase 3,7 positive, as shown in FIG. 9, and the Antp-TPR peptide also caused the loss of survivin, as shown in FIG. 4 (A), and thus, the Antp-TPR peptide seems to cause mass killing of cancer cells depending on survivin expression by apoptotic mechanism.

(Discussion)

As described above, since the peptide newly designed in the present example binds to Hsp90 specifically, does not function alone, exerts killing effect specifically to cancer cells when it is incorporated into a cell as a chimeric complex with a cell-penetrating peptide, and is effective particularly to cancer cells in which survivin is expressed in a greater amount. There is potential in the application of such a peptide as a new therapeutic agent for cancers with no current options for treatment. In contrast to the methods targeted to Hsp90 by using conventional compounds, a peptide is used here and no influence is exerted on normal cells, and thus, the peptide may overcome the problem of the adverse action in cancer therapy. Thus, the design of sequences displaying higher specificity for cancer cells compared to the current sequence designed and having a far superior killing ability, through substitution of each of the amino acids in the sequence or combination with other cell-penetrating peptides is expected to occur in the future. In addition, application of such a new therapeutic agent combined with the peptide is highly expected not only to cancer, but also to refractory diseases such as inflammatory disease and interstitial pneumonia, by suppression of inflammatory cytokines and other with the peptide.

Example 2

Comprehensive Analysis of the TPR Domain-Binding Peptides

In the present Example, an experiment was performed to determine whether the analogues of the Hsp90 TPR domain-binding peptide (amino acid sequence $X_1X_2X_3X_4X_5X_6X_7X_8X_9X_{10}X_{11}X_{12}$ (SEQ ID NO: 1); wherein:

$X_1$ is K, R or A;
$X_2$ is A or G;
$X_3$ is Y or L;
$X_4$ is A or G;
$X_5$ is R, A or K;
$X_6$ is I or R;
$X_7$ is G or A;
$X_8$ is N or Q;
$X_9$ is S or Y;
$X_{10}$ is Y or S;
$X_{11}$ is F or Y;
$X_{12}$ is K or R, or

Antp-TPR slong (Antp-RQIAKAYARIGNSYF-KEEKYK; SEQ ID NO: 39), which was obtained by elongation of the TPR peptide), could be used. An experiment using peptide in which R11 was used in place of TPR was also performed.

All protocols were in accordance with those in Example 1, except that the peptide sequence was different. Peptides used include the following:

```
SEQ ID No. 9:
RQIKIWFQNRRMKWKKKAYARIGNSYFK (Antp-wild)

SEQ ID No. 10:
RQIKIWFQNRRMKWKKRAYARIGNSYFK (Antp-K1R)

SEQ ID No. 11:
RQIKIWFQNRRMKWKKAAYARIGNSYFK (Antp-K1A)

SEQ ID No. 12:
RQIKIWFQNRRMKWKKKGYARIGNSYFK (Antp-A2G)

SEQ ID No. 13:
RQIKIWFQNRRMKWKKKALARIGNSYFK (Antp-Y3L)

SEQ ID No. 14:
RQIKIWFQNRRMKWKKKAYGRIGNSYFK (Antp-A4G)

SEQ ID No. 15:
RQIKIWFQNRRMKWKKKAYAKIGNSYFK (Antp-R5K)

SEQ ID No. 16:
RQIKIWFQNRRMKWKKKAYARRGNSYFK (Antp-I6R)

SEQ ID No. 17:
RQIKIWFQNRRMKWKKKAYARIANSYFK (Antp-G7A)

SEQ ID No. 18:
RQIKIWFQNRRMKWKKKAYARIGQSYFK (Antp-N8Q)

SEQ ID No. 19:
RQIKIWFQNRRMKWKKKAYARIGNYYFK (Antp-S9Y)

SEQ ID No. 20:
RQIKIWFQNRRMKWKKKAYARIGNSSFK (Antp-Y10S)

SEQ ID No. 21:
RQIKIWFQNRRMKWKKKAYARIGNSYYK (Antp-F11Y)

SEQ ID No. 22:
RQIKIWFQNRRMKWKKKAYARIGNSYFR (Antp-K12R)
```

(Protocol)

Respective variant peptides were subjected to cell viability assay. Specifically, Caki-1 (American Type Culture Collection (Manassas, Va.) was inoculated in a total amount of $3\times10^3$ cells per well on a 96 well plate (Nunc™); the cells were cultured in a medium (DMEM (Tesque, Inc.) containing 10% FBS (fetal bovine serum; Biowest)) for 24 hours and incubated with 100 µl of a peptide having a gradual increase in concentration at 37° C. for 48 to 72 hours. The cell survival rate was measured by using WST-8 solution (Cell Count Reagent SF; Nacalai Tesque, Inc.) and compared with that of the wild-type Antp-TPR peptide.

(Results)

Results are shown in FIG. 5 and the table below. The number in the table shows a relative value, and the wild-type peptide is assumed to be 100%.

TABLE 3

| Peptide | Antp-wild | Antp-K1R | Antp-K1A | Antp-A2G | Antp-Y3L | Antp-A4G | Antp-R5K | Antp-I6R | Antp-G7A | Antp-N8Q | Antp-S9Y | Antp-Y10S | Antp-F11Y | Antp-K12R |
|---|---|---|---|---|---|---|---|---|---|---|---|---|---|---|
| SEQ ID No. | 9 | 10 | 11 | 12 | 13 | 14 | 15 | 16 | 17 | 18 | 19 | 20 | 21 | 22 |
| Cell survival rate (%) | 10.68 | 68.01 | 81.87 | 10.08 | 52.77 | 3.20 | 94.12 | 98.26 | 14.04 | 11.95 | 4.60 | 33.40 | 1.30 | 19.43 |

TABLE 3-continued

| Peptide SEQ ID No. | Antp-wild 9 | Antp-K1R 10 | Antp-K1A 11 | Antp-A2G 12 | Antp-Y3L 13 | Antp-A4G 14 | Antp-R5K 15 | Antp-I6R 16 | Antp-G7A 17 | Antp-N8Q 18 | Antp-S9Y 19 | Antp-Y10S 20 | Antp-F11Y 21 | Antp-K12R 22 |
|---|---|---|---|---|---|---|---|---|---|---|---|---|---|---|
| Decrease in cell survival rate (% relative to wild-type peptide) | 100 | 15.70 | 13.04 | 105.96 | 20.23 | 333.52 | 11.34 | 10.87 | 76.07 | 89.35 | 232.05 | 31.97 | 820.08 | 54.95 |
| Anti-cancer activity (% relative to wild-type peptide) | 100 | 35.81 | 20.29 | 100.70 | 52.87 | 108.40 | 6.58 | 1.95 | 96.23 | 98.57 | 106.80 | 74.56 | 110.50 | 90.20 |

All the values above can be considered positive, because the "anti-cancer activity" may be present, if about 1(%) of the wild-type peptide that has a very high activity remains.

As shown above, peptides A4G (SEQ ID NO: 14), S9Y (SEQ ID NO: 19) and F11Y (SEQ ID NO: 21) showed an effect stronger than that of the wild-type peptide, and peptides A2G (SEQ ID NO: 12), G7A (SEQ ID NO: 17), N8Q (SEQ ID NO: 18), Y10S (SEQ ID NO: 20) and K12R (SEQ ID NO: 22) showed an effect similar to that of the wild-type peptide. It was found that the mutations other than those described above also show a killing effect, although weaker, they are considered to be effective as a killing peptide.

The results above indicate that the following variations are allowed.

Amino acid sequence $X_1X_2X_3X_4X_5X_6X_7X_8X_9X_{10}X_{11}X_{12}$ (SEQ ID NO: 1); wherein $X_1$ is an amino acid K or a hydrophilic amino acid similar thereto such as R or A or the like, and preferably K;

$X_2$ is an amino acid A or an aliphatic side chain amino acid similar thereto such as G, V, L or I or the like;

$X_3$ is an amino acid Y or a hydrophobic amino acid similar thereto such as L or the like, and preferably Y;

$X_4$ is an amino acid A or an aliphatic side chain amino acid similar thereto such as G, V, L or I or the like;

$X_5$ is an amino acid R or an amino acid similar thereto such as K or A or the like, and preferably R;

$X_6$ is an amino acid I or an amino acid similar thereto such as R or the like, and preferably I (or I or A, as shown in separate examples);

$X_7$ is an amino acid G or an amino acid similar thereto which is found in other TPR domain such as A or the like;

$X_8$ is an amino acid N or an amino acid similar thereto which is found in other TPR domain such as Q or the like;

$X_9$ is an amino acid S or an OH group-containing amino acid similar thereto such as T or Y or the like;

$X_{10}$ is an amino acid Y or an OH group-containing amino acid similar thereto such as S or T or the like;

$X_{11}$ is an amino acid F or an aromatic amino acid similar thereto such as Y or the like; and $X_{12}$ is an amino acid K or a basic amino acid similar thereto such as R or the like.

It was found that generally conservative substitution is permitted, but the three-dimensional model shown in FIG. 1 shows that the structure of the side chain of $X_1$ or $X_5$ has a strict influence on the anti-cancer activity. Thus, it is found that the conservative substitution, if conducted, should be carried out at an amino acid site other than the sites described above. Substitution of $X_6$ to R is not conservative substitution and, as apparent from the results in Example 8 and Table 9, substitution to A, which is conservative substitution, lead to preservation of the activity, indicating that the influence the structure of the side chain has on the anti-cancer activity is not so strict. For improvement of the activity of the peptide according to the present invention to more than that of the wild type, it is advantageous to mutate the residues other than $X_1$ and $X_5$, but the mutation is not limited thereto.

Favorable patterns observed include the followings:

Specifically in the amino acid sequences above, those in which $X_2$ is G; $X_4$ is G; $X_7$ is A; $X_4$ is Q; $X_9$ is Y; $X_{10}$ is S; $X_{11}$ is Y; and/or $X_{12}$ is R, and these favorable substitutions in any combination can be effective.

More preferably, in the amino acid sequences above, those in which $X_4$ is G; $X_9$ is Y; and $X_{11}$ is Y, and these preferable substitutions in any combination can be more effective.

It is understood that these results indicate that the killing effect would be preserved if multiple mutations with preserved killing effects are combined.

It is also found that the following addition sequence, insertion sequence or deletion is also permitted. Specifically, Antp-RAYAR (SEQ ID NO: 65), Antp-AAYAR (SEQ ID NO: 66), Antp-KGYAR (SEQ ID NO: 67), Antp-KALAR (SEQ ID NO: 68), Antp-KAYGR (SEQ ID NO: 69) and the like are also considered to be effective. That is, since Antp-KAYAR (SEQ ID NO: 42) has a killing effect, it is understood that the peptides with similar substitution can also be used, as those having a similar effect.

Example 3

Test of Other Cell-Penetrating Peptides

In the present Example, it was investigated whether cell-penetrating peptides other than the Antp peptides could be used.

The peptides used include the following: All protocols were in accordance with those in Example 1, except that the peptide sequences of the cell-penetrating peptides were different.

Specifically, an experiment was performed by using Antp-TPRslong (Antp-RQIAKAYARIGNSYFKEEKYK; SEQ ID NO: 39), which was obtained by elongation of the TPR peptide, and the peptide in which R11 (RRRRRRRRRRR; SEQ ID NO: 7) was used in place of TPR.

All protocols were in accordance with those in Example 1, except that the peptide sequences of the cell-penetrating peptides were different.

```
YGRKKRRQRRR       (TAT SEQ ID No. 6)

RRRRRRRRRRR      (R11 SEQ ID No. 7)
```

The sequences produced are the followings:

```
R11-TPR (RRRRRRRRRRRKAYARIGNSYFK;)    SEQ ID No. 40
TAT-TPR (YGRKKRRQRRRKAYARIGNSYFK;)    SEQ ID No. 50
```

(Results)

Figure 6:
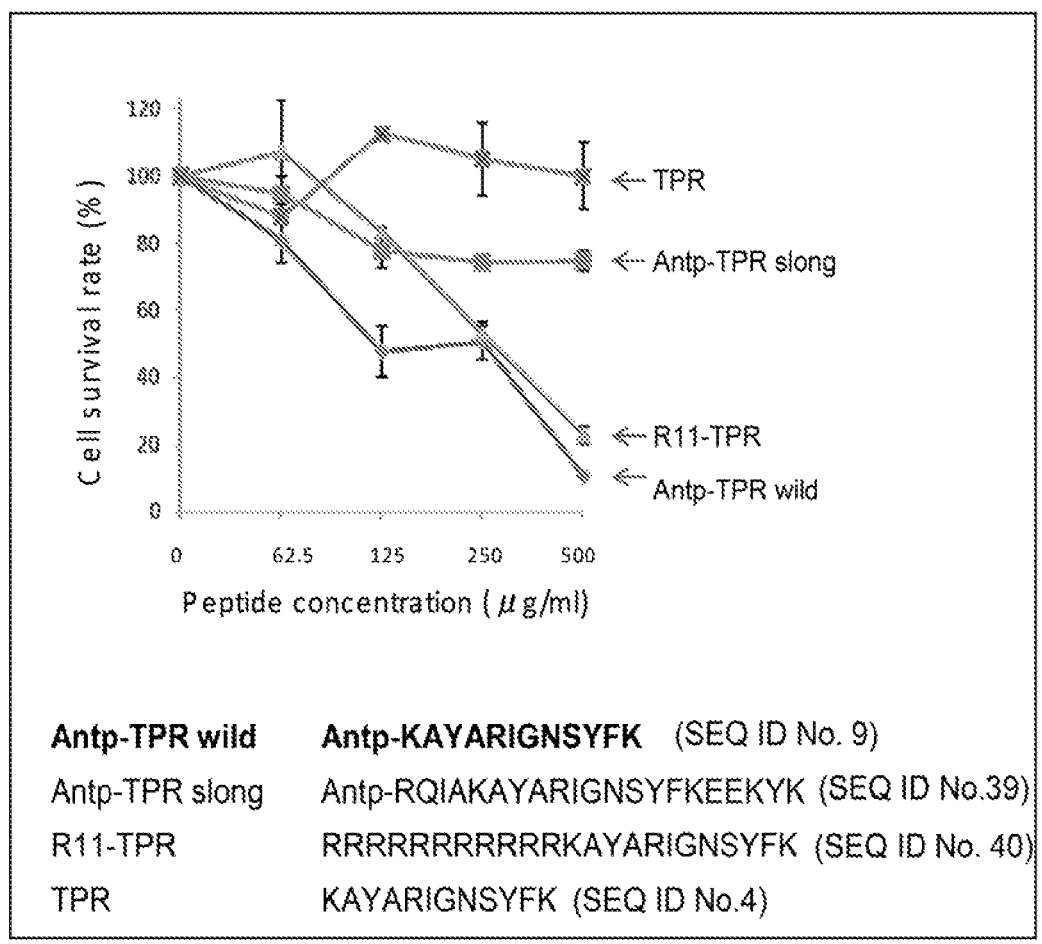
FIG. 6 shows the cytotoxic activity to Caki-1 of wild-type TPR and "slong", an elongated type and a variant peptides obtained by using R11 in place of the wild type sequence.

The results obtained with TAT are shown in FIG. 3D, and the results obtained with R11 are shown in FIG. 6 and the table below. Since R11-TPR showed an effect similar to that of the wild-type Antp-TPR, it can be said that R11 also has a cell-killing effect, although there is some difference in the effect. The Antp-TPR slong retained the effect of wild-type peptide. Thus, it was demonstrated that the anti-cancer activity is not lost, even if the length of the peptide is modified. In addition, since a similar effect was exerted with TAT (FIG. 3D), introduction of a cell-penetrating peptide upstream of TPR was shown to give an effective peptide, demonstrating the flexibility of the present invention.

TABLE 4

| Peptide Concentration (μg/ml) | Antp-TPR wild (SEQ ID No. 9) | Antp-TPR slong (SEQ ID No. 39) | R11-TPR (SEQ ID No. 40) | TPR (SEQ ID No. 4) |
|---|---|---|---|---|
| | Cell survival rate (%) | | | |
| 0 | 100 | 100 | 100 | 100 |
| [SD] | 0 | 0 | 0 | 0 |
| 62.5 | 80.70 | 94.68 | 107.14 | 87.65 |
| [SD] | 6.66 | 5.18 | 15.60 | 8.35 |
| 125 | 47.67 | 77.58 | 83.33 | 112.54 |
| [SD] | 7.71 | 5.09 | 1.19 | 2.14 |
| 250 | 50.78 | 74.21 | 53.18 | 105.00 |
| [SD] | 5.62 | 0.19 | 2.36 | 10.83 |
| 500 | 10.68 | 74.60 | 22.76 | 99.96 |
| [SD] | 0.76 | 3.07 | 2.65 | 9.93 |

Example 4

Variation of Cell-Penetrating Peptide

In the present Example, it was investigated whether those having the analogues of the cell-penetrating peptide (RQIKI-WFQNRRMKWKK (SEQ ID NO: 5)) (amino acid sequence $Y_1Y_2Y_3Y_4Y_5Y_6Y_7Y_8Y_9Y_{10}Y_{11}Y_{12}Y_{13}Y_{14}Y_{15}Y_{16}$ (SEQ ID NO: 8), wherein:

$Y_1$ is an amino acid R or a hydrophilic amino acid similar thereto such as K or the like;

$Y_2$ is an amino acid Q or an amide-based amino acid similar thereto such as N or E as Glx or the like;

$Y_3$ is an amino acid I or an aliphatic amino acid similar thereto such as L or the like;

$Y_4$ is an amino acid K or a hydrophilic amino acid similar thereto such as R or the like;

$Y_5$ is an amino acid I or an aliphatic amino acid similar thereto such as L or the like;

$Y_6$ is an amino acid W or an aromatic amino acid similar thereto such as Y or the like;

$Y_7$ is an amino acid F or an aromatic amino acid similar thereto such as Y or the like;

$Y_8$ is an amino acid Q or an amide-based amino acid similar thereto such as N or E as Glx or the like;

$Y_9$ is an amino acid N or an amide-based amino acid similar thereto such as Q or the like;

$Y_{10}$ is an amino acid R or a hydrophilic amino acid similar thereto such as K or the like;

$Y_{11}$ is an amino acid R or a hydrophilic amino acid similar thereto such as K or the like;

$Y_{12}$ is an amino acid M or an S-containing amino acid similar thereto such as C or the like;

$Y_{13}$ is an amino acid K or a hydrophilic amino acid similar thereto such as R or the like;

$Y_{14}$ is an amino acid W or an aromatic amino acid similar thereto such as Y or the like;

$Y_{15}$ is an amino acid K or a hydrophilic amino acid similar thereto such as R or the like;

$Y_{16}$ is an amino acid K or a hydrophilic amino acid similar thereto such as R or the like), could be used. All protocols were in accordance with those in Example 1, except that the peptide sequences were different.

(Protocol)

Respective variant peptides were subjected to cell viability assay. Specifically, Caki-1 (American Type Culture Collection (Manassas, Va.) was inoculated in a total amount of $3 \times 10^3$ cells per well on a 96 well plate (Nunc™); the cells were cultured in a medium containing 10% FBS for 24 hours and incubated with 100 μl of a peptide having a gradual increase in concentration at 37° C. for 48 to 72 hours. The cell survival rate was measured by using WST-8 solution (Cell Count Reagent SF; Nacalai Tesque, Inc.) and compared with that of the wild-type Antp-TPR peptide.

(Results)

Results are shown in FIG. 8A and the Table below. The number in the table shows a relative value, when the wild-type peptide is assumed to be 100%.

TABLE 5

| Peptide SEQ ID No. | Antp-wild 9 | Antp-R1K-TPR 23 | Antp-Q2N-TPR 24 | Antp-13L-TPR 25 | Antp-K4R-TPR 26 | Antp-15L-TPR 27 | Antp-W6Y-TPR 28 | Antp-F7Y-TPR 29 | Antp-Q8N-TPR 30 |
|---|---|---|---|---|---|---|---|---|---|
| Cell survival rate (%) | 10.68 | 42.74 | 20.52 | 38.25 | 1.86 | 34.12 | 70.53 | 73.33 | 2.06 |
| Decrease in cell survival rate (% relative to wild-type peptide) | 100 | 24.98 | 52.02 | 27.91 | 573.28 | 31.29 | 15.14 | 14.56 | 519.29 |
| Anti-cancer activity (% relative to wild-type peptide) | 100 | 64.10 | 88.97 | 69.12 | 109.86 | 73.75 | 32.99 | 29.86 | 109.65 |

TABLE 5-continued

| Peptide SEQ ID No. | Antp N9Q-TPR 31 | Antp R10K-TPR 32 | Antp R11K-TPR 33 | Antp M12C-TPR 34 | Antp K13R-TPR 35 | Antp W14Y-TPR 36 | Antp K15R-TPR 37 | Antp K16R-TPR 38 |
|---|---|---|---|---|---|---|---|---|
| Cell survival rate (%) | 1.21 | 1.47 | 6.75 | 8.28 | 2.96 | 25.54 | 1.55 | 1.51 |
| Decrease in cell survival rate (% relative to wild-type peptide) | 881.03 | 727.03 | 158.09 | 128.91 | 360.96 | 41.80 | 687.99 | 709.01 |
| Anti-cancer activity (% relative to wild-type peptide) | 110.59 | 110.30 | 104.39 | 102.68 | 108.64 | 83.36 | 110.21 | 110.26 |

All the values above can be considered to be positive, because the "anti-cancer activity" may be considered to be present, if about 1(%) of the wild-type peptide that has a very high activity remains, and all the peptides above retained an activity of about 30% or more.

As shown above, peptides K4R (SEQ ID NO: 26), Q8N (SEQ ID NO: 30), N9Q (SEQ ID NO: 31), R10K (SEQ ID NO: 32), R11K (SEQ ID NO: 33), M12C (SEQ ID NO: 34), K13R (SEQ ID NO: 35), K15R (SEQ ID NO: 37) and K16R (SEQ ID NO: 38) showed an effect stronger than that of the wild-type peptide. In addition, peptides Q2N (SEQ ID NO: 24) and W14Y (SEQ ID NO: 36) also showed an effect similar to that of the wild-type peptide. It was shown that mutations other than those above also show a killing effect, although it is weak. The results above demonstrated that the cancer cell-killing effect of the present invention is preserved if the cell permeability of the cell-penetrating peptide is preserved.

As described above, it is understood that mutation to the cell-penetrating peptide also leads to maintenance of the effect of cell permeability.

Example 5

Treatment Method

In the present Example, application to actual treatment was confirmed.

Here, in-vivo kinetic stabilization and sustained delivery and the like by Drug Delivery system (DDS) and also the anti-tumor effect in cancer-bearing animal models were studied.

(DDS)

Atelocollagen (Koken Co., Ltd.) and the Antp-TPR peptide are mixed (atelocollagen was mixed in a manner that its content was an amount of 0.3% in 400 μg/ml Antp-TPR peptide (SEQ ID NO: 9)) and the stability of the peptide was observed by HPLC. Specifically, the waveform of the peptide alone is measured; it is possible to determine the degree of peptide release from atelocollagen and at the same time confirm the stability of the peptide by detecting the degree of the waveform at the site of the peptide over time, when the mixture of atelocollagen and the peptide is measured. In addition, the therapeutic effect of the mixture was examined by administering it to solid cancer-transplanted animals prepared in the following manner.

(Anti-Tumor Effect in Cancer-Bearing Animal Models by Local Administration)

Human pancreatic cancer cells (Bxpc 3) ($5.0 \times 10^6$) were suspended in 150 μl of phosphate-buffered physiological saline (PBS) and transplanted subcutaneously into nude mice (BALB/c Slc-nu/nu). After 5 days, 150 μl of the Antp-TPR peptide suspended in PBS at a concentration of 1 mg/kg to 5 mg/kg was administered to the solid cancer every two days for a total of nine times, and the tumor contraction effect was examined. The tumor diameter was measured with calipers and the tumor volume ($mm^3$) was calculated according to the formula: length (mm)×minor diameter $(mm)^2 \times 0.5$.

(Anti-Tumor Effect in Cancer-Bearing Animal Models by Intravenous Administration)

Human pancreatic cancer cells (Bxpc 3) ($5.0 \times 10^6$) were suspended in 150 μl of phosphate-buffered physiological saline (PBS), and the suspension was transplanted into the lateral region of 7 to 9-week old nude mice (Balb/c Slc-nu/nu) (body weight: 17 to 21 g) subcutaneously. At the time point when the tumor volume reached 20 to 50 $mm^3$, the mice were divided into three groups (n=6/group) at random, and PBS (control) or Antp-TPR (1 or 5 mg/kg) was administered by intravenous injection (50 μl/injection) thrice a week for a total of 9 times and the tumor contraction effect was examined. The tumor diameter measurement and tumor volume were calculated, similarly as that in the case of local administration above.

(Results)

Figure 8B:
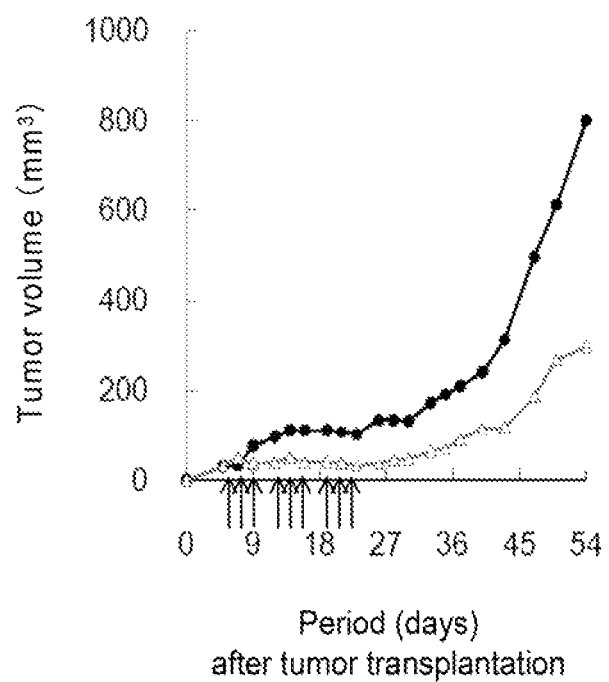
FIG. 8B shows an in-vivo effect on solid cancer by local administration of Antp-TPR. After transplantation of pancreatic cancer cells Bxpc3, PBS administration group (black circle) and Antp-TPR (5 mg/kg)-local administration group (square) (both, N=3) were compared. The abscissa represents the days after transplantation and each arrow represents an administration date. The ordinate represents tumor volume ($mm^3$). The anti-cancer action is distinctively observed in the Antp-TPR peptide administration group.
Figure 8C:
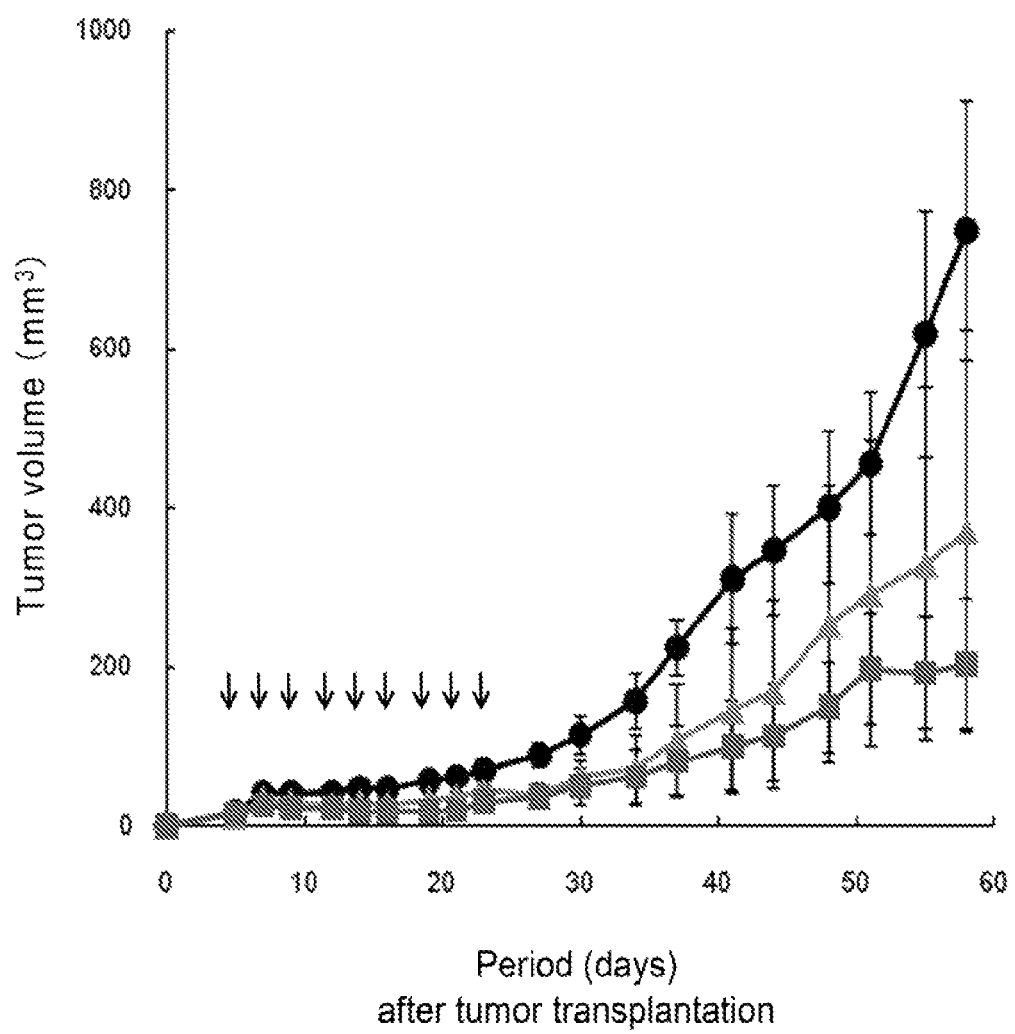
FIG. 8C shows the in-vivo effect of solid cancer to intravenous administration of Antp-TPR. After transplantation of pancreatic cancer cell Bxpc3, the PBS administration group (black circle) and the Antp-TPR intravenous administration group (1 mg/kg (triangle) or 5 mg/kg (square)) were compared (both, N=6). The abscissa represents the days after transplantation and each arrow represents the date of administration. The ordinate represents tumor volume ($mm^3$). The experiments were conducted in parallel, and the data were expressed as average±SD. The anti-cancer action was definitely observed in the Antp-TPR peptide administration group.

Results are shown in FIG. 8B (anti-tumor effect by local administration) and FIG. 8C (anti-tumor effect by intravenous administration).

As apparent from FIG. 8B, in the experiment by local administration, the tumor contraction effect was observed in the mice of Antp-TPR peptide-administered group, in contrast to the mice of PBS-administered control group. In addition, the site of administration and the behavior of the mice thereafter were observed (normal behavior without decreased appetite) indicating that there was little toxicity to the mice throughout the experimental period.

As apparent from FIG. 8C, in the experiment by intravenous administration, tumor contraction effect was observed in the Antp-TPR peptide-administered mice, in contrast to the PBS-administered control group. Specifically, the control group showed progressive tumor growth, leading to a tumor volume of 749 $mm^3$ on 58th day, but tumor growth was suppressed distinctively in the mice intravenously administered with Antp-TPR peptide (1 or 5 mg/kg). The average tumor volume on 58th day was 371 $mm^3$ in the 1 mg/kg-administered group and 204 $mm^3$ in the 5 mg/kg-administered group ($P<0.05$ compared with the mice of control group).

These results indicate that the Antp-TPR peptide according to the present invention induces death in cancer cells effectively in vivo.

These results and in vitro results show that, variants showing an effect similar to that of the Antp-TPR peptide in vitro are also expected to show similar results in vivo and those showing about half the effect in vitro are expected to show about half the effect in vivo, and even if variants show about half the effect in vitro, they are estimated to have an activity of 5 times or more higher than conventional shepherdin in vivo, and thus, the peptide according to the present invention is expected to have an activity generally more superior compared to conventional anti-cancer agents, especially anti-cancer peptide agents.

Example 6

Examination on Cancer Cell-Killing Effect by FACS

In the present Example, the cancer cell-killing effect of the peptide according to the present invention was examined for confirmation of the specificity thereof to cancer cells in DDS.
(Protocol)
Cancer cells T47D and normal cells HEK293T were cultured in their respective media on a 6-well dish (Nunc™) for 24 hours and then, 68 µM of the Antp-TPR chimeric peptide was added thereto, and the mixture was cultured additionally for 48 hours. After culturing, each cell suspension was stained with propidium iodide (PI) or labeled with annexin V (both, Wako) and annexin V labeled and PI stained samples were analyzed simultaneously by multiparametric flow cytometry.
(Results)
Results are shown in FIG. 9. Addition of the Antp-TPR peptide to the normal cells HEK293T exerted no influence, but the addition of the peptide to the cancer cells T47D resulted in an increase in annexin V-positive or caspase 3,7-positive cell populations.

Accordingly, the results indicated that the peptide added induces death of cancer cells specifically by the apoptotic mechanism.

Specifically, there is no influence observed even if the Antp-TPR peptide was added to normal cells HEK293T, while, if the peptide was added to cancer cells T47D, there is an increase of PI and annexin V positive or caspase 3,7 positive cells observed. Accordingly, it is found that the cancer cells T47D are killed by addition of the peptide or the killed cells undergo apoptosis.

Example 7

Use as a Transfection Reagent

Figure 10:
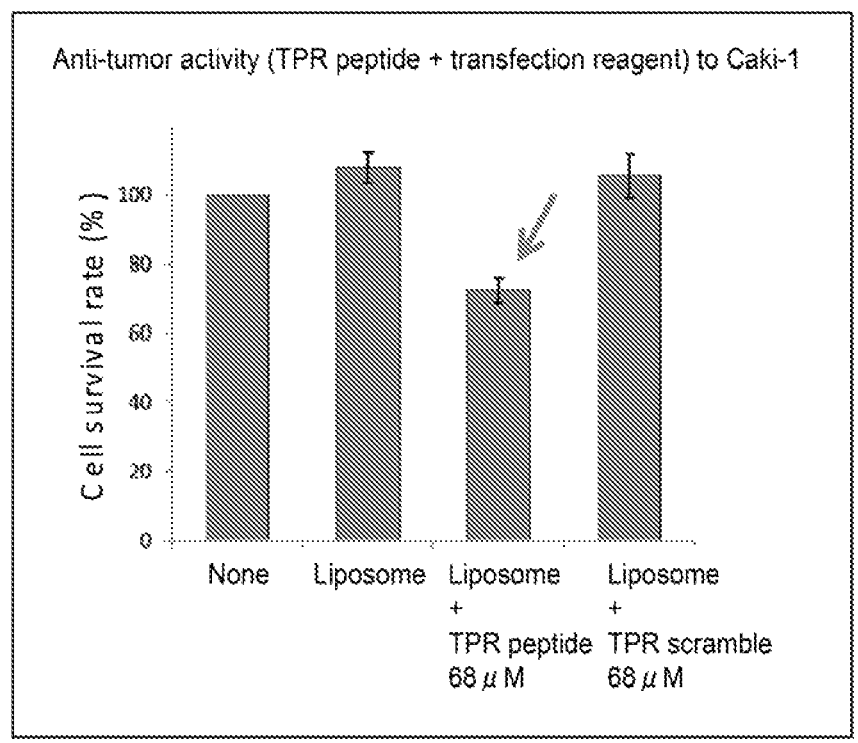
FIG. 10 shows the results obtained in a transfection experiment. None indicates the case where no treatment was made (the value was set to 100%); Liposome indicates the case where only a transfection reagent was introduced; Liposome+TPR 68 µM indicates the case where the TPR peptide was introduced with the transfection reagent; and Liposome+TPR scramble 68 µM indicates the case where the TPR scramble peptide was introduced with the transfection reagent. Only in the region indicated by the arrow, i.e., when the TPR peptide was introduced, the cell-killing effect was observed. When only the TPR peptide was introduced into the cancer cells Caki-1 with a transfection reagent, only the TPR peptide showed the cell-killing effect.

The TPR peptide or the TPR scramble peptide was mixed with a commercially available transfection reagent (Profect-P2 or, Lipofectamine LTX) and the mixture was left to incubate at room temperature for 20 minutes, to form liposome before the complex was added to cancer cells (Caki-1 (kidney cancer cells)); the survival rate of the cells was then measured by using WST-8 solution (Cell Count Reagent SF; Nacalai Tesque, Inc.) and the results were compared with those such as in the case of the TPR scramble peptide or the liposome alone.
(Results)
Results are shown in FIG. 10 and the table below. As apparent from FIG. 10, the killing effect was not observed when the liposome alone and the TPR scramble peptide were used, but observed when the TPR peptide was introduced.

If only the TPR peptide was introduced into cancer cells Caki-1 with a transfection reagent, only the killing effect by the TPR peptide was observed.

TABLE 6

|  | None | Liposome | Liposome + TPR peptide 68 uM | Liposome + TPR scramble 68 uM |
|---|---|---|---|---|
| Cell survival rate (%) | 100 | 108.03 | 72.45 | 105.55 |
| SD | 0 | 4.48 | 3.59 | 6.56 |

It is thus understood that the TPR peptide can be used as a factor for drug delivery system (DDS).

Example 8

Production of Hsp90 TPR-Binding Peptide-Antp Chimeric Peptide and Measurement of Biological Activity It was examined whether the chimeric peptide according to the present invention has a cell-killing effect or anti-tumor effect similarly in blood cancer cells, in particular in leukemia-derived cell strains.
(Materials and Methods)
(Cell Strains)
Human leukemia-derived cell strains: U937 (monoblastic leukemia), K562 (chronic myelocytic leukemia), THP-1 (monocytic leukemia), HL-60 (myeloblastic leukemia) and human normal B cell (RPMI1788) were purchased from the Japan Health Sciences Foundation (Tokyo, Japan). A human embryonic kidney cell strain (HEK293) was purchased from RIKEN Cell Bank (Tsukuba, Japan). A human lung normal epithelial cell strain (WI38) was purchased from American Type Culture Collection (Manassas, Va., USA). A human normal pancreas epithelial cell strain (PE) was purchased from DS Pharma Biomedical Co., Ltd. The cells were cultured in RPMI 1640 (U937, K562, THP-1, HL-60, RPMI1788), CSC (PE), MEM (WI38) or D-MEM (HEK293) containing 10% FBS (BioWest, Miami, Fla., USA), 100 µg/ml penicillin and 100 µg/ml streptomycin (Nacalai Tesque, Inc., Kyoto, Japan).
(Peptides)
The following peptides were purchased from Invitrogen, Carlsbad, Calif., USA or synthesized using a peptide synthesizer (for example, Applied Biosystems, CA USA: Model 433A peptide synthesizer):

```
chimeric peptide Antp-TPR:
                                        (SEQ ID No. 9)
RQIKIWFQNRRMKWKK-KAYARIGNSYFK, (Antp-TPR K1R or Antp-K1R; SEQ ID No. 10)
RQIKIWFQNRRMKWKKRAYARIGNSYFK, (Antp-TPR K1A or Antp-K1A; SEQ ID No. 11)
RQIKIWFQNRRMKWKKAAYARIGNSYFK, (Antp-TPR A2G or Antp-A2G; SEQ ID No. 12)
RQIKIWFQNRRMKWKKKGYARIGNSYFK, (Antp-TPR Y3L or Antp-Y3L; SEQ ID No. 13)
RQIKIWFQNRRMKWKKKALARIGNSYFK, (Antp-TPR A4G or Antp-A4G; SEQ ID No. 14)
RQIKIWFQNRRMKWKKKAYGRIGNSYFK, (Antp-TPR R5K or Antp-R5K; SEQ ID No. 15)
RQIKIWFQNRRMKWKKKAYAKIGNSYFK, (Antp-TPR I6R or Antp-I6R; SEQ ID No. 16)
RQIKIWFQNRRMKWKKKAYARRGNSYFK,
```

-continued

```
            (Antp-TPR G7A or Antp-G7A;  SEQ ID No. 17)
RQIKIWFQNRRMKWKKKAYARIANSYFK, (Antp-TPR N8Q or Antp-N8Q;  SEQ ID No. 18)
RQIKIWFQNRRMKWKKKAYARIGQSYFK, (Antp-TPR S9Y or Antp-S9Y;  SEQ ID No. 19)
RQIKIWFQNRRMKWKKKAYARIGNYYFK, (Antp-TPR Y10S or Antp-Y10S; SEQ ID No. 20)
RQIKIWFQNRRMKWKKKAYARIGNSSFK, (Antp-TPR F11Y or Antp-F11Y; SEQ ID No. 21)
RQIKIWFQNRRMKWKKKAYARIGNSYYK, (Antp-TPR K12R or Antp-K12R; SEQ ID No. 22)
RQIKIWFQNRRMKWKKKAYARIGNSYFR, (elongated TPR peptide;  SEQ ID No. 43)
RQIAKAYARIGNSYFKEEKYK, (Antp-R5A;  SEQ ID No. 51)
RQIKIWFQNRRMKWKKKAYAAIGNSYFK, (Antp-I6A;  SEQ ID No. 52)
RQIKIWFQNRRMKWKKKAYARAGNSYFK, (Antp-A2G, A4G, S9Y, F11Y;   SEQ ID No. 53)
RQIKIWFQNRRMKWKKKGYGRIGNYYYK,
and (Antp-scramble peptide; SEQ ID No. 54)
RQIKIWFQNRRMKWKKRKFSAAIGYNKY.
```

These peptides were chemically synthesized, purified by high-performance liquid chromatography and then dissolved in water.

(Cell Viability Assay)

A total of $3\times10^3$ cells per well were inoculated onto a 96 well plate, and incubated in a medium containing 10% FBS with 100 μl of a peptide diluted stepwise at 37° C. for 48 to 72 hours. The survival rate of the cells was measured by using WST-8 solution (Cell Count Reagent SF; Nacalai Tesque, Inc.).

(Western Blotting)

Leukemia cell strains were cultured in respective media on a 6-well plate (Nunc™) for 24 hours; the supernatant was washed with phosphate-buffered buffer solution (PBS) at least twice; Cell lysis buffer (Promega) was added to respective wells in an amount of 300 μl for the lysis of cells, to give a total cell-extract protein (total protein). The extract solution was separated by SDS-PAGE and the proteins were transferred onto a membrane by semi-dry method. A 10% skim milk solution was prepared by using a phosphate-buffered buffer solution (PBS); after blocking for 1 hour and 30 minutes, the mixture was allowed to react in a solution (Stressgen Bioreagents, SIGMA) containing antibodies to Hsp90, survivin and actin overnight; and then, the solution was allowed to react with a secondary antibody (GE Healthcare, USA) and chemically stained with an ECL kit (GE Health science); and the bands were detected in Las3000 system.

(Fluorescence Microscope Analysis)

TPR-TAMRA (TAMRA labeled body) or Antp-TPR-TAMRA (TAMRA labeled body) was added to $1\times10^6$ peripheral blood mononuclear cells (PBMCs), which were prepared from U937 cells, a mouse leukemia cell strain EL4 or mouse peripheral blood, at a final concentration of 10 μM, and the mixture was cultured for 1 hour. The peptide incorporated in the cell or influx of the medium into the cell after peptide penetration was observed under a confocal microscope (Olympus FV1000 (Olympus)), using a medium containing calcein.

(Flow Cytometry Assay)

For determination of the cancer cell-killing effect of 50 μM Antp-TPR chimeric peptide to the leukemia cell strain U937, annexin V labeling and PI staining of the peptide-treated culture were analyzed simultaneously by propidium iodide (PI) staining or multiparametric flow cytometry.

The change in the electric potential of mitochondria was measured by multiparametric flow cytometry, after the cells treated as described above were incubated additionally in a medium containing fluorescent cationic pigment reagent JC-1 for 15 minutes and then washed with PBS.

For the measurement of the caspase 3,7, the caspase activity and the propidium iodide (PI) staining of the cells treated similarly as described above was measured by using carboxy-fluorescein FLICA caspase 3,7 assay (Immunochemistry Technologies, Bloomington, Minn., USA) and by multiparametric flow cytometry.

(Results of Cell Viability Assay)

Figure 11:
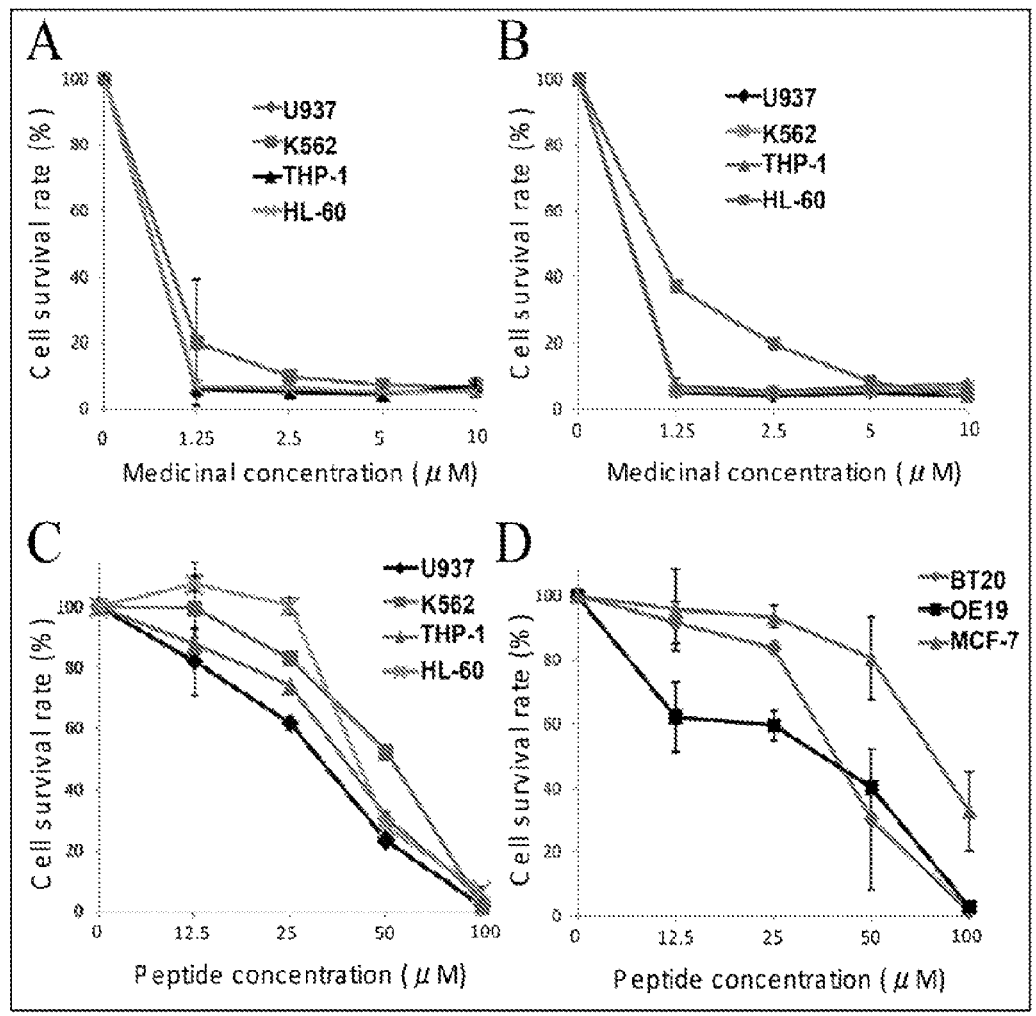
FIG. 11 shows the cytotoxic activity of two kinds of Hsp90 inhibitors and the Antp-TPR chimeric peptide according to the present invention. Graphs (A) to (C) are graphs showing the cell-killing effect on leukemia cell strains (U937, K562, THP-1, HL-60) by Hsp90 inhibitors, geldanamycin (A), 17-AAG (B) and Antp-TPR chimeric peptide (C). Graph (D) is a graph showing the cell-killing effect of the Antp-TPR chimeric peptide to solid cancer cell strains (BT20, OE19 and MCF-7).

FIG. 11 and the table below show the cytotoxic activity of Antp-TPR, from the results of the cell viability assay.

Figs. (A) to (C) show the cell-killing effects to leukemia cell strains (U937, K562, THP-1 and HL-60) of Hsp90 inhibitors, low-molecular weight compounds, geldanamycin (A), 17-AAG (B) and Antp-TPR chimeric peptide (C), while Fig. (D) shows the cell-killing effect of the Antp-TPR chimeric peptide to solid cancer cell strains (BT20, OE19 and MCF-7).

TABLE 7

| (A) Geldanamycin | | | | |
|---|---|---|---|---|
| Peptide Concentration | Cell Survival Rate (%) | | | |
| (μM) | U937 | K562 | THP-1 | HL-60 |
| 0 | 100 | 100 | 100 | 100 |
| [SD] | 0 | 0 | 0 | 0 |
| 1.25 | 5.40 | 20.08 | 6.20 | 6.65 |
| [SD] | 1.84 | 18.89 | 2.60 | 0.62 |
| 2.5 | 6.26 | 9.75 | 5.01 | 6.02 |
| [SD] | 0.21 | 1.91 | 0.26 | 0.31 |
| 5 | 4.65 | 7.07 | 4.49 | 5.03 |
| [SD] | 0.45 | 0.66 | 0.26 | 0.02 |
| 10 | 5.78 | 6.60 | 7.12 | 5.23 |
| [SD] | 2.48 | 0.36 | 2.43 | 0.67 |
| (B) 17-AAG | | | | |
| Peptide Concentration | Cell Survival Rate (%) | | | |
| (μM) | U937 | K562 | THP-1 | HL-60 |
| 0 | 100 | 100 | 100 | 100 |
| [SD] | 0 | 0 | 0 | 0 |
| 1.25 | 5.21 | 5.67 | 6.80 | 37.03 |
| [SD] | 0.84 | 0.58 | 2.57 | 0.47 |
| 2.5 | 4.03 | 5.08 | 5.49 | 19.70 |
| [SD] | 0.06 | 1.11 | 1.03 | 0.08 |
| 5 | 4.97 | 5.67 | 6.56 | 8.37 |
| [SD] | 0.01 | 0.56 | 0.33 | 0.10 |
| 10 | 4.16 | 6.35 | 7.76 | 3.87 |
| [SD] | 0.31 | 0.83 | 0.42 | 0.65 |
| (C) Antp-KAYARIGNSYFK (Antp-TPR; SEQ ID No. 9) | | | | |
| Peptide Concentration | Cell Survival Rate (%) | | | |
| (μM) | U937 | K562 | THP-1 | HL-60 |
| 0 | 100 | 100 | 100 | 100 |
| [SD] | 0 | 0 | 0 | 0 |
| 1.25 | 82.03 | 99.53 | 87.59 | 107.53 |

TABLE 7-continued

| | | | | |
|---|---|---|---|---|
| [SD] | 10.99 | 15.45 | 2.36 | 2.49 |
| 2.5 | 61.71 | 82.97 | 74.08 | 100.22 |
| [SD] | 2.16 | 1.98 | 0.79 | 2.93 |
| 5 | 23.35 | 52.32 | 30.83 | 27.75 |
| [SD] | 0.53 | 1.01 | 1.67 | 1.41 |
| 10 | 1.88 | 1.51 | 4.50 | 6.61 |
| [SD] | 1.54 | 0.38 | 3.79 | 0.89 |

(D) Antp-KAYARIGNSYFK (Antp-TPR; SEQ ID No. 9)

| Peptide Concentration | Cell Survival Rate (%) | | |
|---|---|---|---|
| (µM) | BT20 | 0E19 | MCF-7 |
| 0 | 100 | 100 | 100 |
| [SD] | 0 | 0 | 0 |
| 1.25 | 91.56 | 62.10 | 95.64 |
| [SD] | 6.49 | 10.85 | 12.70 |
| 2.5 | 83.80 | 59.45 | 93.36 |
| [SD] | 1.95 | 4.86 | 3.42 |
| 5 | 30.12 | 40.08 | 80.50 |
| [SD] | 21.94 | 1.15 | 12.91 |
| 10 | 1.71 | 2.77 | 32.73 |
| [SD] | 1.61 | 0.92 | 12.51 |

The results in FIG. 11 showed that the chimeric peptide Antp-TPR according to the present invention has a cell-killing effect to acute myelogenous leukemia cell strains similarly to Hsp90 inhibitors, geldanamycin and 17-AAG, and that survivin was expressed significantly in all of the cell strains where a cell-killing effect was observed. In addition, from the results shown in FIG. 11(D) it was found that the chimeric peptide also has a cell-killing manner similar to that to solid cancer cell strains.

Furthermore, as a result of calculating the $IC_{50}$ value from the data on cytotoxic activity, geldanamycin and 17-AAG showed cell-killing effect on both of normal cells and acute myelogenous leukemia cell strains (both has low $IC_{50}$ concentrations), while the Antp-TPR chimeric peptide showed little cell-killing effect to normal cells and showed the cell-killing effect only in leukemia cell strains, exerting its influence on leukemia cell strains with an $IC_{50}$ in the range of 20 µM to 60 µM (Table 8: Cell-killing effect of geldanamycin, 17-AAG and Antp-TPR chimeric peptide ($IC_{50}$) to normal cells and acute myelogenous leukemia cell strains).

TABLE 8

Inhibitory concentration($IC_{50}$) of geldanamycin, 17-AAG and Antp-TPR

| | Anti-tumor activity, $IC_{50}$ (µM) * | | | | | | |
|---|---|---|---|---|---|---|---|
| | Normal cells | | | Human AML cells | | | |
| | HEK | PE | W138 | U937 | K562 | THP-1 | HL-60 |
| Geldanamycin | 0.70 | 0.70 | 1.00 | 0.65 | 0.75 | 0.70 | 0.70 |
| 17-AAG | 0.70 | 0.80 | 0.70 | 0.70 | 0.70 | 0.75 | 1.05 |
| Antp-TPR | 100> | 100> | 100> | 25.2 | 54.2 | 24.7 | 46.4 |

* The results are the averages of two independent experiments carried out respectively in three times.

(Amounts of Proteins Expressed)

Figure 12:
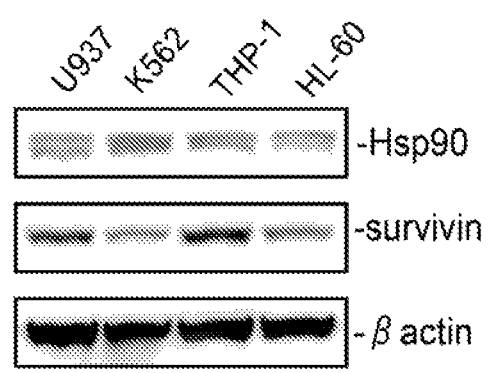
FIG. 12 shows the results obtained by Western blotting of leukemia cell strains. The amounts of (from top) Hsp90, survivin and β-actin (control) expressed respectively in U937 cell, K562 cell, THP-1 cell and HL-60 cell (from left) were determined.

The amounts of the proteins (Hsp90, survivin and β-actin (control)) expressed in the respective leukemia cell strains (U937, K562, THP-1 and HL-60) were examined by Western blotting, and it was found that survivin was expressed in greater amounts in U937 and THP-1, as shown in FIG. 12. Accordingly, it was found that the Antp-TPR chimeric peptide is effective to leukemia cell strains expressing survivin in greater amounts, similar to solid cancer cells.

(Penetration Experiment of Antp-TPR Chimeric Peptide into Acute Myelogenous Leukemia Cell Strain U937)

TPR-TAMRA (TAMRA labeled body) or Antp-TPR-TAMRA (TAMRA labeled body) was added to $1 \times 10^6$ U937 cells to a final concentration of 10 µM; the mixture was cultured for one hour; and then the behavior of the peptide incorporated into the cell or the influx of the medium into the cell after peptide penetration was observed under a confocal microscope (Olympus FV1000 (Olympus)), using a calcein-containing medium.

Figure 13A:
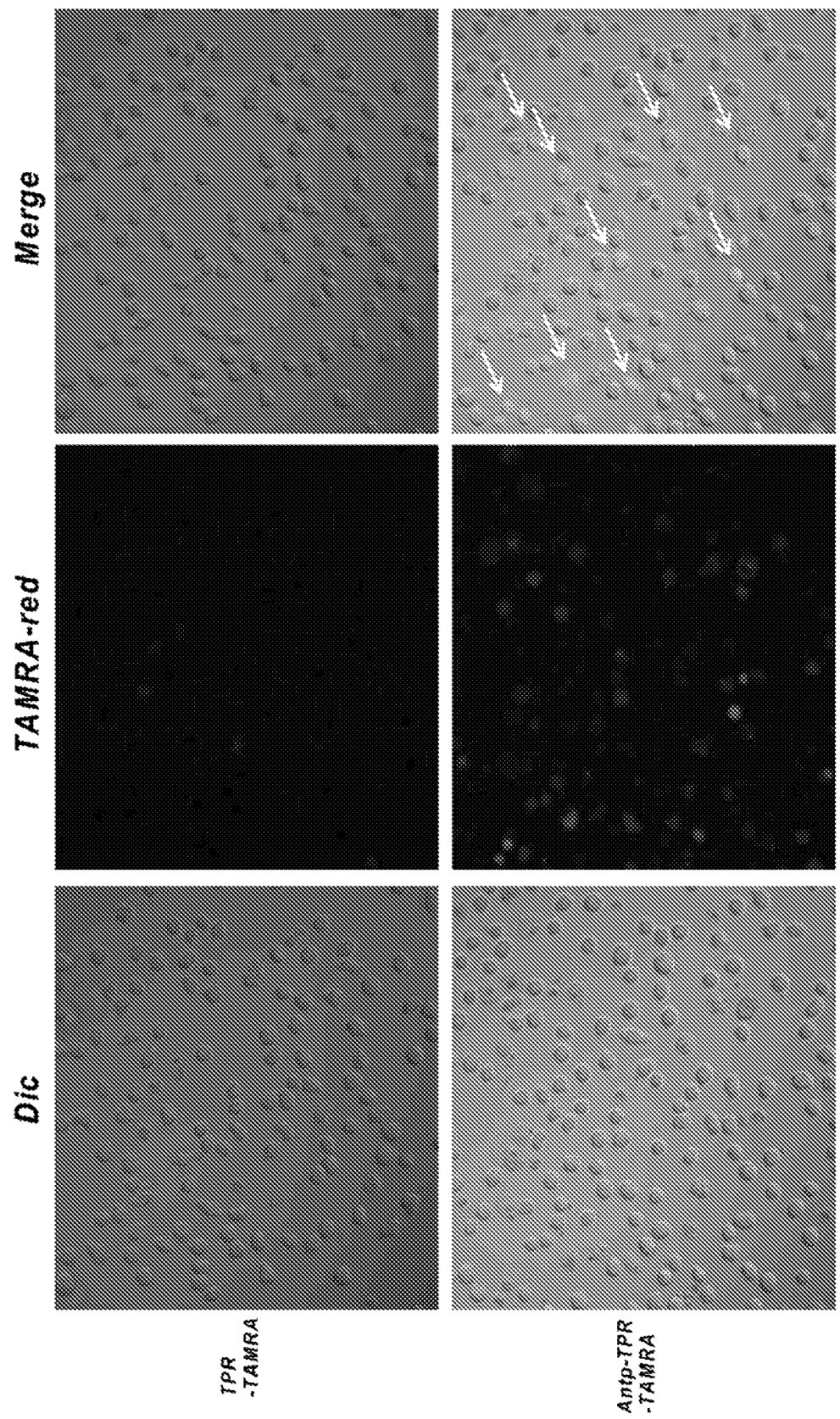
FIG. 13 shows the results of a penetration experiment of the Antp-TPR chimeric peptide on an acute myelogenous leukemia cell strain U937. Photograph (A): intracellular penetration of the TAMRA-labeled Antp-TPR was confirmed, but the intracellular penetration of the TPR peptide was not confirmed. The arrow in the figure indicates the cells into which the peptide had penetrated.
Figure 13B:
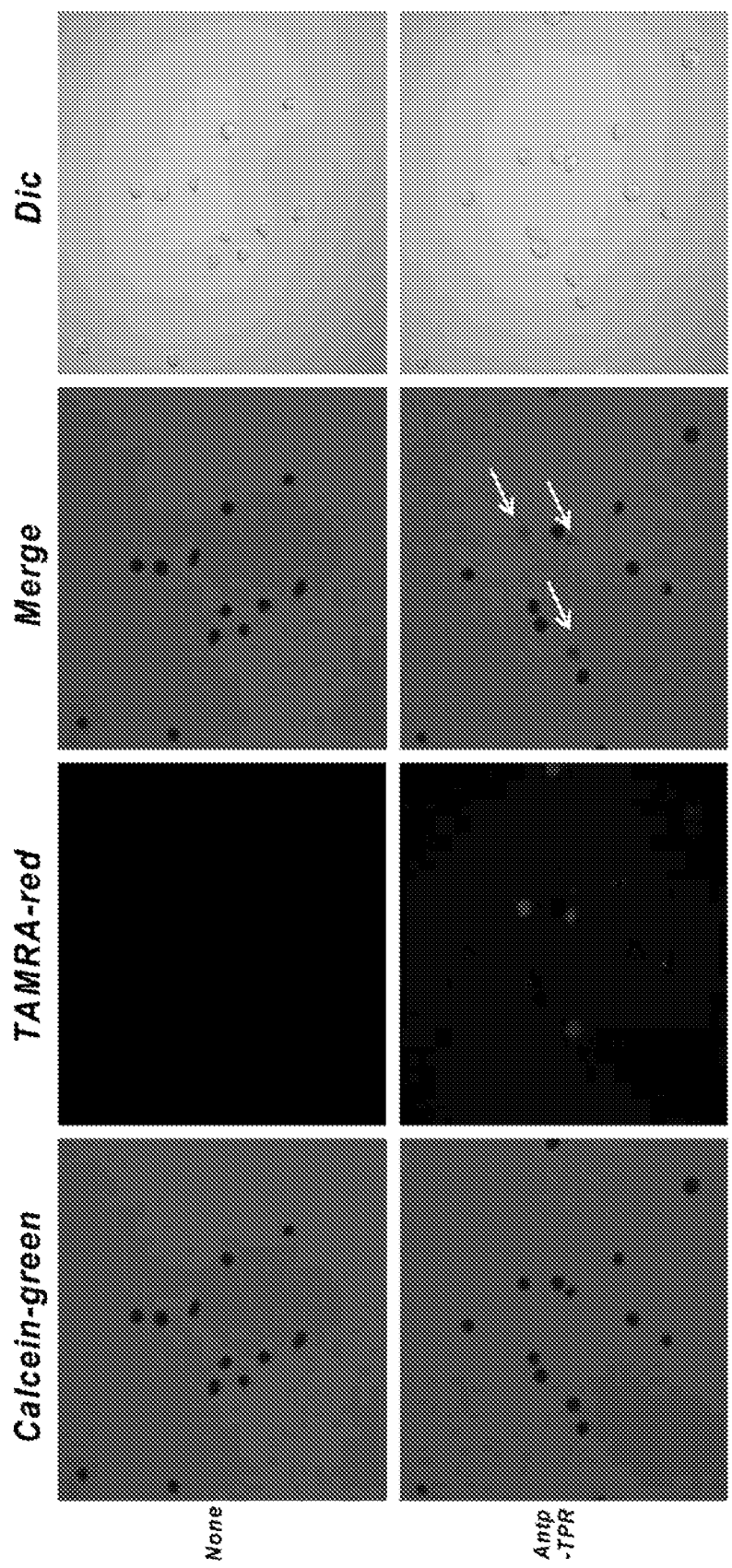

As shown in FIG. 13(A), it was confirmed that the TAMRA-labeled Antp-TPR penetrated into the cell, but the TPR peptide without Antp did not penetrate into the cell. As shown in FIG. 13(B), since no influx of calcein (green) into the cell was observed after penetration of the Antp-TPR chimeric peptide into the cell, it was found that the Antp-TPR chimeric peptide penetrated into the cell without destruction of the cell membrane. In addition, the membrane was not destructed even after penetration of the peptide. The arrows in the figure indicate the cells into which the peptide has penetrated.

(Analysis of Cancer Cell-Killing Effect of Antp-TPR Chimeric Peptide to Leukemia Cell Strain U937)

Figure 14:
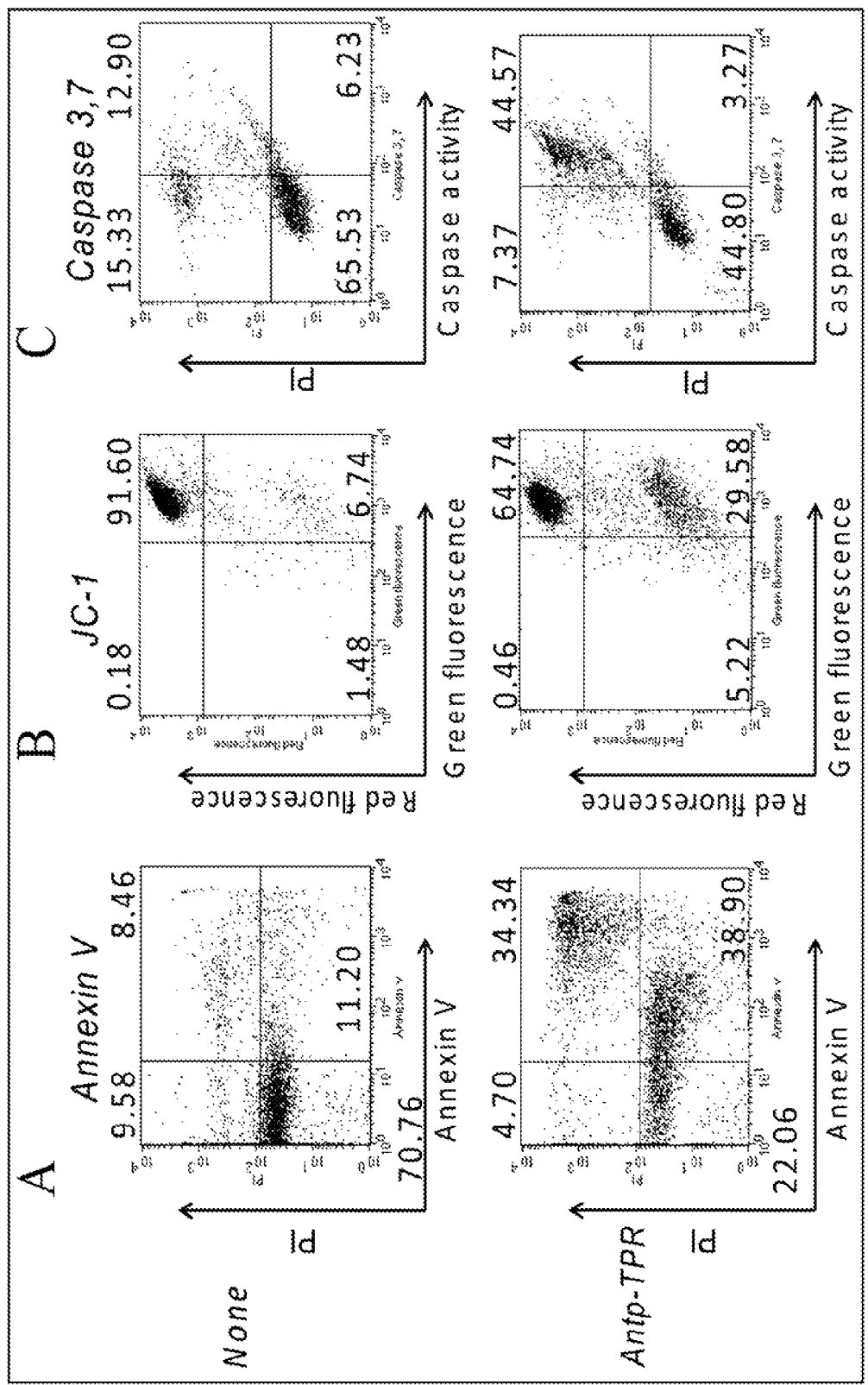
FIG. 14 shows the results obtained by examining the cancer cell-killing effect of the Antp-TPR chimeric peptide on a leukemia cell strain U937. Graph (A) shows the results obtained by incubating U937 cells with 50 µM of Antp-TPR chimeric peptide at 37° C. overnight, staining the cells with propidium iodide (PI), and analyzing annexin V labeled and PI stained cells by multiparametric flow cytometry. Increase in annexin V positive cells was observed in the Antp-TPR-treated group, as shown in the top right quarter panel of the graph. Graph (B) shows the results obtained from pre-treating U937 cells with the chimeric peptide in a manner similar to (A) with JC-1 for 15 minutes and analyzing the green and red fluorescence by multiparametric flow cytometry. Change in the mitochondria membrane potential was observed in the Antp-TPR-treated group, as shown in the bottom right quarter panel of the graph. Graph (C) shows the results obtained by determining the caspase activity and the PI staining of the chimeric peptide-treated U937 cells similarly to (A) by using carboxyfluorescein FLICA caspase 3,7 assay and by multiparametric flow cytometry. Increase in the caspase 3 and 7-active cells were observed in the Antp-TPR-treated group, as shown in the top right quarter panel of the graph.

FIG. 14 shows the results obtained by flow cytometry assay.

FIG. 14(A) shows the results obtained by incubating U937 cells with 50 µM of Antp-TPR chimeric peptide at 37° C. overnight, staining the cells with propidium iodide (PI), and analyzing annexin V labeling and PI staining of the cells by multiparametric flow cytometry. Increase of annexin V-positive cells (killed) was observed after Antp-TPR-treatment, as shown in the top right quarter panel of the graph.

FIG. 14(B) shows the results obtained by mixing the U937 cells similarly treated with the chimeric peptide with JC-1 for 15 minutes and analyzing the green and red fluorescence by multiparametric flow cytometry. Change of the mitochondria membrane potential was observed in the Antp-TPR-treated group, as shown in the bottom right quarter panel of the graph.

Further, FIG. 14(C) shows the results obtained by determining the caspase activity and the PI staining of the U937 cells similarly treated with the chimeric peptide by using carboxyfluorescein FLICA caspase 3,7 assay and by multiparametric flow cytometry. Increase of the caspase 3 and 7-active cells was observed in the Antp-TPR-treated group, as shown in the top right quarter panel of the graph.

The results above showed that the Antp-TPR chimeric peptide induces apoptosis of the leukemia cell strain U937 by activation of caspase 3,7 and causes the change of the electric potential of the mitochondrial membrane.

(Loss of Hsp90 Client Protein Caused by Antp-TPR Chimeric Peptide)

Figure 15:
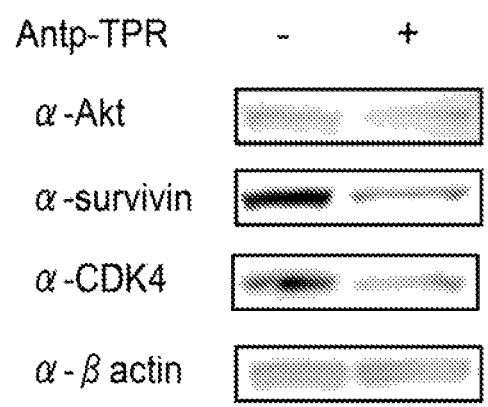
FIG. 15 shows the loss of the Hsp90 client proteins caused by the Antp-TPR chimeric peptide. U937 cells were incubated with the Antp-TPR chimeric peptide at 37° C. overnight; the cell extract was then subjected to Western blotting with antibodies respectively to the proteins shown. As shown in the figure, the expression amounts of the peptides were lower in the Antp-TPR (+) sample than in the Antp-TPR (−) sample, indicating that the Antp-TPR chimeric peptide exerts an influence on the folding of the Hsp90's client proteins in the leukemia cell strain U937, and actually, production of respective proteins were found to be reduced. "α-" in the figure means that it is the antibody used during Western blotting.

U937 cells were incubated with the Antp-TPR chimeric peptide at 37° C. overnight; the cell extract was then subjected to Western blotting with antibodies to respective proteins. As shown in FIG. 15, the amounts of respective proteins expressed are reduced in Antp-TPR (+), compared to Antp-TPR (−), expecting that the Antp-TPR chimeric peptide exerts influence on the folding of Hsp90's client protein in the leukemia cell strain U937, and it was found that the amounts of respective proteins were reduced.

(Influence on Cell-Killing Effect of Antp-TPR Chimeric Peptide to U937 Cell Strain Caused by Mutation of Each Amino Acid)

Figure 16:
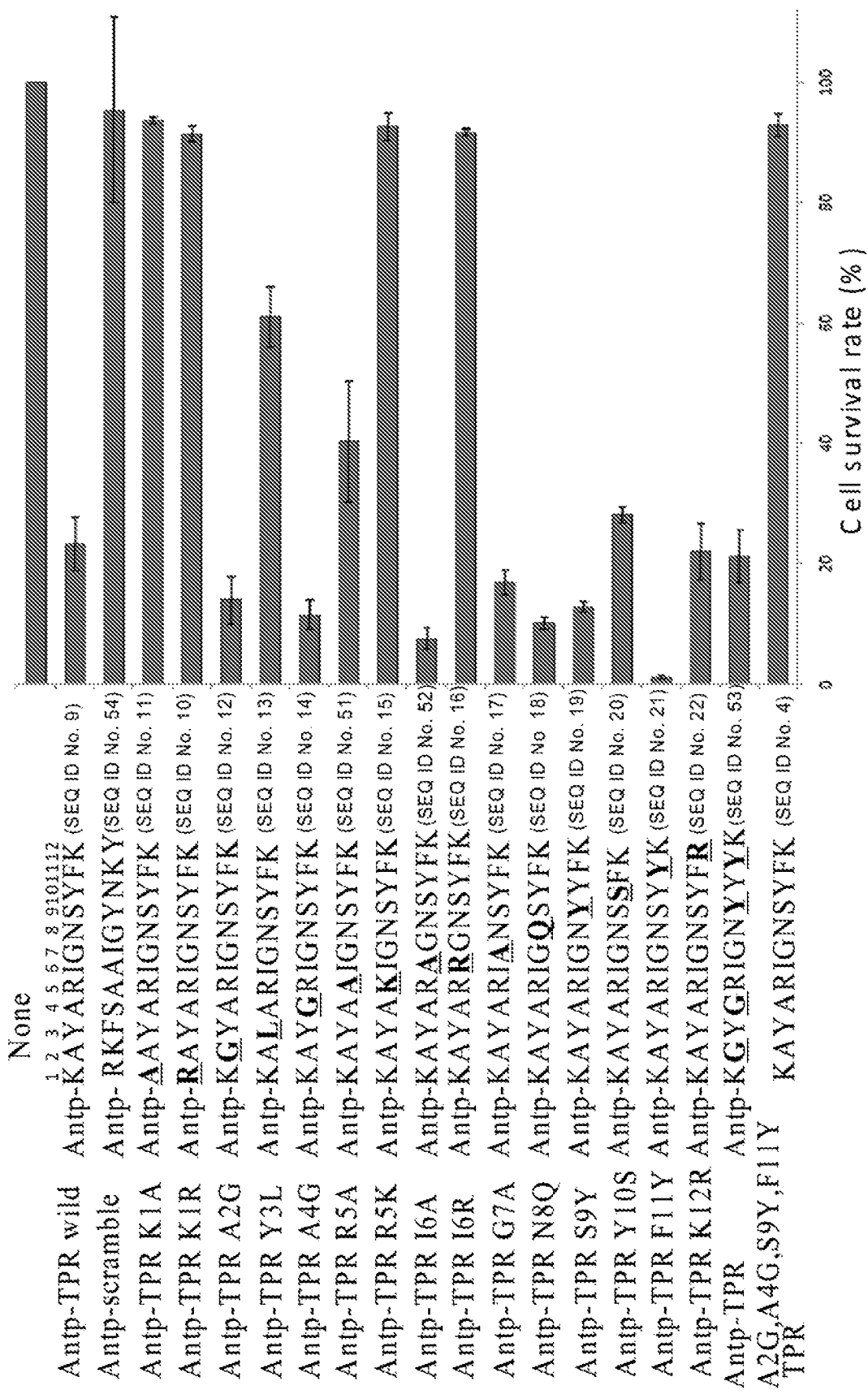
FIG. 16 shows the influence of the cell-killing effect of U937 cell strains by the Antp-TPR chimeric peptides containing mutation on each amino acid. It shows the results of a test for determining the cell-killing effect on U937 by chimeric peptides containing an amino acid mutation. The results of analysis of the sites of each amino acid mutation showed that the introduction of conservative mutation at the respective amino acid sites resulted in the retention of the cell-killing ability.

The cell-killing effect to U937 of each of the chimeric peptides containing amino acid mutation shown in FIG. 16 was examined. As a result, it was found that a conservative amino acid mutation at each site results in preservation of the cell-killing ability. Relative values, when the wild-type peptide is assumed to be 100%, are shown in the following table. For evaluation, the values of the decrease in cell survival rate and the killing rate of the cancer cells, i.e., anti-cancer activity are shown in numerical form. Those stronger than the wild-type peptide, it is possible to evaluate for improvement in the activity of an anti-cancer agent more efficiently by examining the reduction of cell survival rate.

cator. In addition, Antp-Y10S (SEQ ID NO: 20) was also found to show an effect similar to that of the wild-type peptide. It was found that mutations other than these have a weak killing effect. Thus, it is demonstrated that the cancer cell-killing effect of the present invention is preserved, as long as the cell permeability of the cell-penetrating peptide is assured. For example, it was also demonstrated that substitution with an amino acid similar in properties, such as conservative substitution, based on active peptides is effective.

As described above, it is understood that the cell permeability effect is preserved even for the mutants of the cell-penetrating peptide.

(Examination of Cell-Killing Effect to Various Species)

The cell-killing effect of the Antp-TPR chimeric peptide to peripheral blood mononuclear cells (PBMCs) containing normal lymph cells collected from mouse peripheral blood, human normal B cells and mouse leukemia cell strain EL4 was examined.

Figure 17:
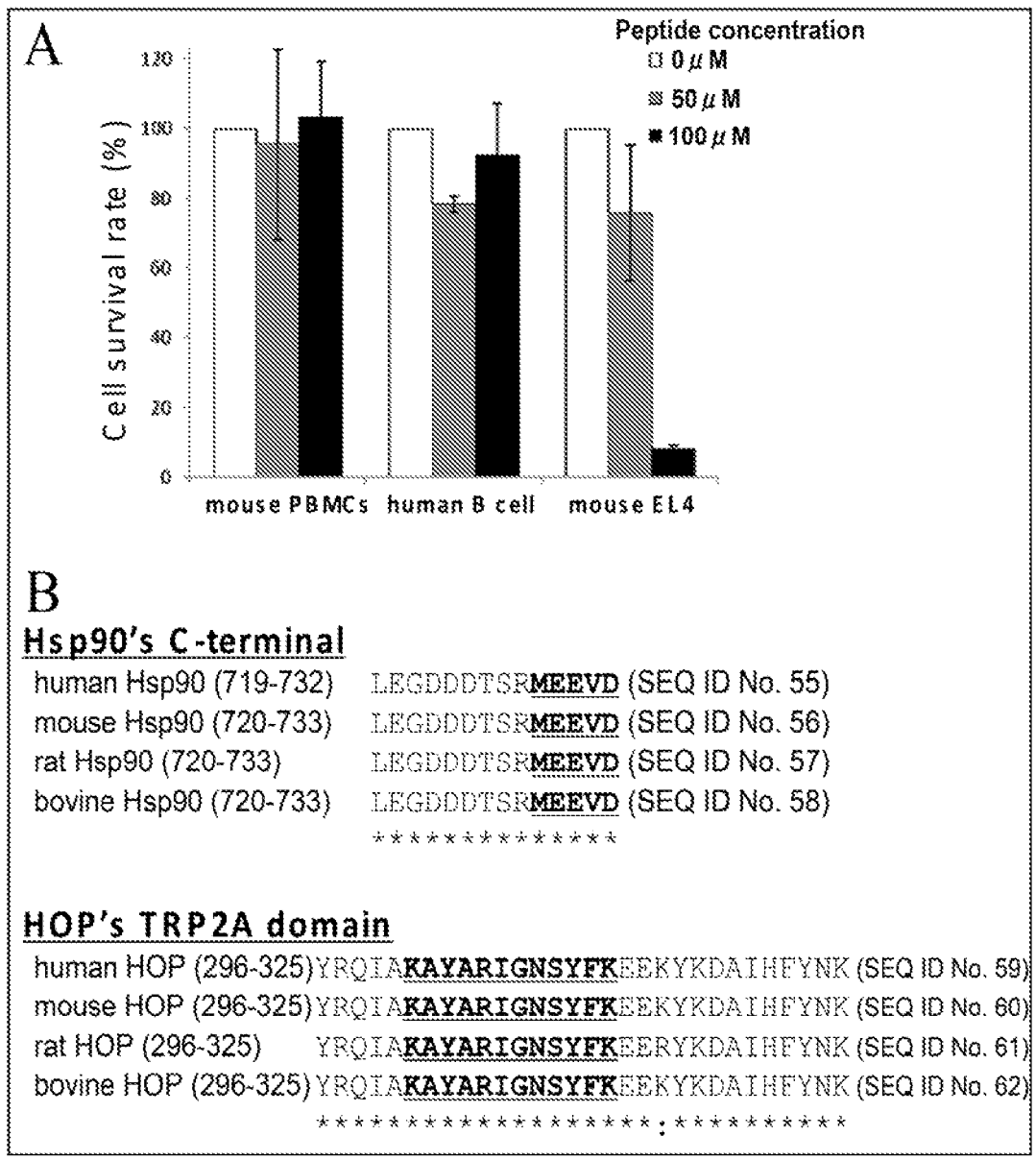
FIG. 17 shows the results obtained by analysis of the differences in cell-killing effect between species. Graph (A) shows the cell-killing effect of the Antp-TPR chimeric peptide to peripheral blood mononuclear cells (PBMCs) collected from mouse peripheral blood containing normal lymph cells, human normal B cells and mouse leukemia cell strain EL4. It was found that the Antp-TPR chimeric peptide does not show the cell-killing effect on mouse PBMCs or human normal B cells but has cell-killing effect on mouse leukemia cell strain. (B) The C-terminal amino acid sequences and the amino acid sequences of the HOP's TPR2A domain of human, mouse, rat and bovine Hsp90's are compared. The sequence of the region important for the anti-cancer action of the Antp-TPR chimeric peptide (Hsp90's C-terminal sequence MEEVD (SEQ ID NO: 64) and the TPR2A domain sequence in HOP KAYARIGNSYFK (SEQ ID NO: 4)) are preserved completely among the species of human, mouse, rat and bovine.

Results are shown in FIG. 17(A) and the table below. It was found that the Antp-TPR chimeric peptide has no cell-killing effect on mouse PBMCs or on human normal B cells, but has a cell-killing effect on mouse leukemia cell strain.

TABLE 9

| Peptide | Antp-wild | Antp-scramble | Antp-K1A | Antp-K1R | Antp-A2G | Antp-Y3L | Antp-A4G | Antp-R5A | Antp-R5K | Antp-I6A |
|---|---|---|---|---|---|---|---|---|---|---|
| SEQ ID No. | 9 | 54 | 11 | 10 | 12 | 13 | 14 | 51 | 15 | 52 |
| Cell survival rate (%) | 23.24 | 95.30 | 93.55 | 91.39 | 13.90 | 60.94 | 11.42 | 40.24 | 92.57 | 7.48 |
| [SD] | 4.43 | 15.4 | 0.68 | 1.24 | 3.99 | 5.08 | 2.48 | 10.09 | 2.29 | 1.86 |
| Decrease in cell survival rate (% relative to wild-type peptide) | 100 | 24.39 | 24.84 | 25.43 | 167.23 | 38.14 | 203.46 | 57.74 | 25.10 | 310.88 |
| Anti-cancer activity (% relative to wild-type peptide) | 100 | 6.13 | 8.41 | 11.22 | 112.17 | 50.89 | 115.40 | 77.85 | 9.68 | 120.54 |

| Peptide | Antp-I6R | Antp-G7A | Antp-N8Q | Antp-S9Y | Antp-Y10S | Antp-F11Y | Antp-K12R | Antp-A2G, A4G, S9Y, F11Y | TPR | None |
|---|---|---|---|---|---|---|---|---|---|---|
| SEQ ID No. | 16 | 17 | 18 | 19 | 20 | 21 | 22 | 53 | 4 | — |
| Cell survival rate (%) | 91.60 | 16.85 | 10.06 | 12.73 | 28.05 | 1.10 | 21.95 | 21.14 | 92.79 | 100 |
| [SD] | 0.64 | 2.12 | 1.09 | 0.85 | 1.33 | 0.39 | 4.7 | 4.35 | 1.94 | — |
| Decrease in cell survival rate (% relative to wild-type peptide) | 25.36 | 137.88 | 230.94 | 182.60 | 82.83 | 2116.95 | 105.89 | 109.90 | 25.04 | — |
| Anti-cancer activity (% relative to wild-type peptide) | 10.92 | 108.32 | 117.17 | 113.69 | 93.73 | 128.84 | 101.68 | 102.73 | 9.39 | — |

All the values above can be considered positive, because the "anti-cancer activity" may be considered present, if about 1(%) of the wild-type peptide that has a very high activity remains, and to be enhanced if it is higher than that of the scramble peptide, and all the values above satisfy this standard.

For peptides Antp-A2G (SEQ ID NO: 2), Antp-16A (SEQ ID NO: 52), Antp-G7A (SEQ ID NO: 17), Antp-N8Q (SEQ ID NO: 18), Antp-S9Y (SEQ ID NO: 19), Atnp-F11Y (SEQ ID NO: 21), Antp-K12R (SEQ ID NO: 22) and Atnp-A2G, A4G, S9Y, F11Y (SEQ ID NO: 53), an increase in effect was observed compared to the wild-type peptide. These peptides were found to have an activity of as high as more than 2000%, if the decrease of the cell survival rate was used as the indi-

TABLE 10

| Peptide | Cell survival rate (%) | | |
|---|---|---|---|
| Concentration | Mouse PBMCs | Human B cells | Mouse EL4 |
| 0 μM | 100 | 100 | 100 |
| [SD] | 0 | 0 | 0 |
| 50 μM | 95.65 | 78.39 | 75.82 |
| [SD] | 27.38 | 2.29 | 19.58 |
| 100 μM | 103.41 | 92.61 | 8.16 |
| [SD] | 15.94 | 14.68 | 1.27 |

As shown in (B), if the Hsp90's C-terminal amino acid sequence and the amino acid sequence of the TPR2A domain in HOP are compared among human, mouse, rat and bovine, it is found that the sequence important for the chimeric peptide showing anti-cancer action (Hsp90's C-terminal sequence MEEVD (SEQ ID NO: 64) and the TPR2A domain sequence KAYARIGNSYFK (SEQ ID NO: 4) in HOP) are completely preserved among the species of human, mouse, rat and bovine. The results above indicate that the Antp-TPR chimeric peptide according to the present invention shows the cell-killing effect is independent of species.

(Penetration Experiment of Antp-TPR Chimeric Peptide into Mouse Leukemia Cell Strain EL4 and PBMCs)

TPR-TAMRA (TAMRA labeled body) or Antp-TPR-TAMRA (TAMRA labeled body) was added to $1 \times 10^6$ cells of mouse leukemia cell strain EL4 or mouse peripheral blood mononuclear cells (PBMCs) at a final concentration of 10 μM; the mixture was cultured for one hour; and then the activity of the peptide which has been incorporated into the cell or the influx of the medium into the cell after peptide penetration was observed under a confocal microscope (Olympus FV1000 (Olympus)), using a calcein-containing medium.

Figure 18:
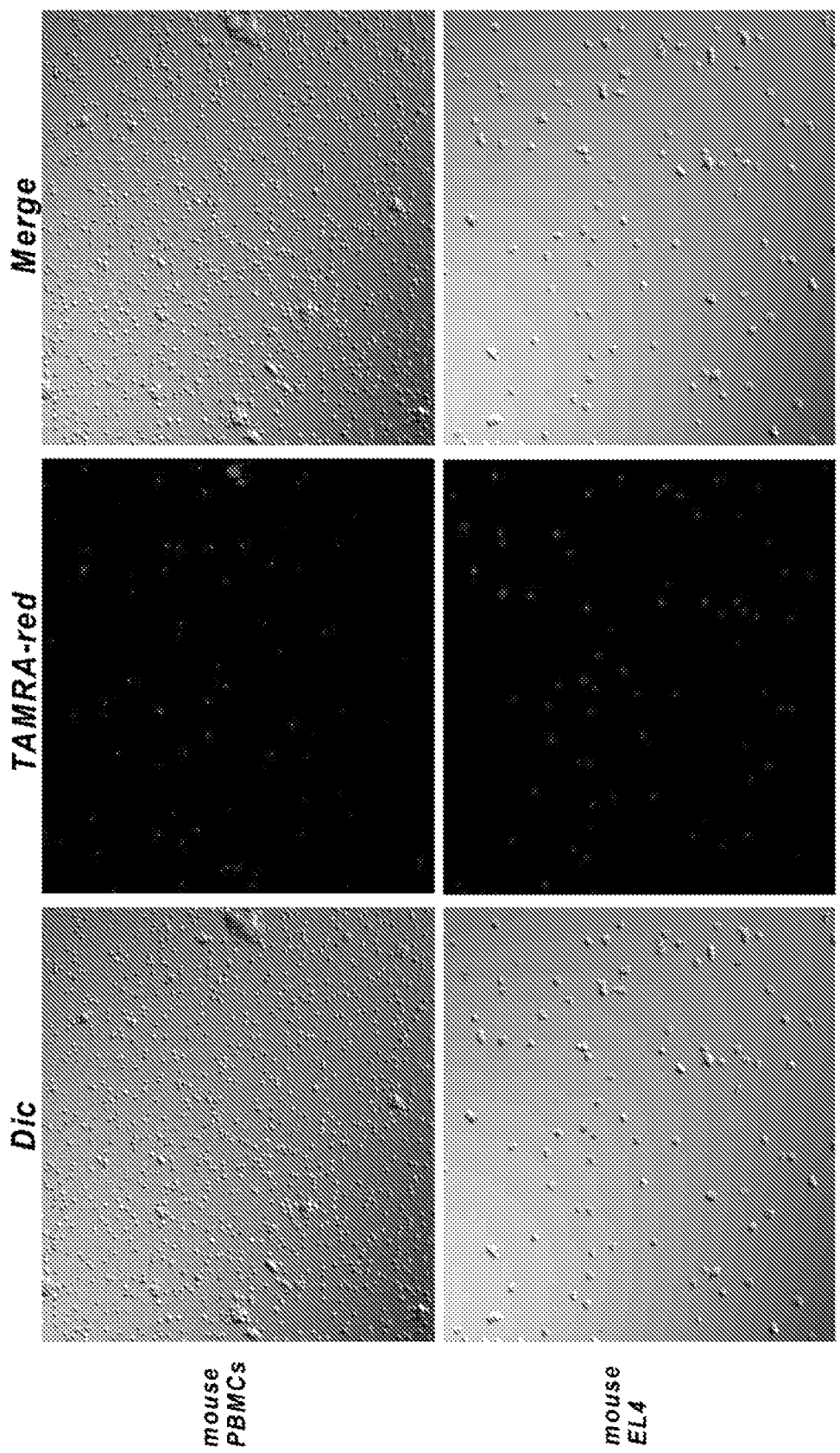
FIG. 18 shows the results of a penetration experiment of the Antp-TPR chimeric peptide into a mouse leukemia cell strain EL4 and PBMCs. It was observed that the Antp-TPR chimeric peptide had penetrated into the mouse cell strain and that the Antp-TPR chimeric peptide does not show cell-killing effect on normal cell PBMCs but shows cell-killing effect on mouse leukemia cell strain.

As shown in FIG. 18, since the Antp-TPR chimeric peptide had penetrated into the mouse cell strain and even if it had penetrated, it showed no cell-killing effect on normal PBMCs, but showed the cell-killing effect on mouse leukemia cell strain. This demonstrated that the peptide has the ability to selectively differentiate between normal and cancer cell in blood cancer cells, similar to that observed in solid cancer cells.

The present invention has been exemplified so far with reference to the favorable embodiments of the present invention, but it should not be construed that the present invention is restricted by the embodiments. It is understood that the scope of the present invention is construed only by the claims. It is understood that those who are skilled in the art can carry out an equivalent range based on the description of the present specification and technical common sense from the description of the specific favorable embodiments of the present invention. It should be interpreted that the contents of the patents, patent applications and literatures herein cited are herein incorporated by reference, similarly to the case where the contents themselves are described specifically in the present specification.

This application claims the priority to the Japanese Patent Application No. 2008-292849, filed in Japan on Nov. 14, 2008. It will be understood that the content of the Japanese Patent Application No. 2008-292849 is hereby incorporated by reference in its entirety and constitutes part of the present specification.

INDUSTRIAL APPLICABILITY

The present invention provides an anti-cancer agent with reduced adverse reaction.

What is claimed is:

1. A chimeric peptide, said peptide comprising a TPR (tetratricopeptide repeat) domain peptide that binds to Hsp90 and a cell-penetrating peptide, wherein the TPR domain peptide comprises the amino acid sequence:

$X_1X_2X_3X_4X_5X_6X_7X_8X_9X_{10}X_{11}X_{12}$ (SEQ ID NO: 1), wherein:
$X_1$ is K, R, or A
$X_2$ is A or G;
$X_3$ is Y or L;
$X_4$ is A or G;
$X_5$ is R, A, or K;
$X_6$ is I, A, or R;
$X_7$ is G or A;
$X_8$ is N or Q;
$X_9$ is S or Y;
$X_{10}$ is Y or S;
$X_{11}$ is F or Y; and
$X_{12}$ is K or R.

2. The chimeric peptide of claim 1, wherein said TPR domain peptide comprises the amino acid sequence of KAYARIGNSYFK (SEQ ID NO:4).

3. The chimeric peptide of claim 1, wherein said TPR domain peptide comprises the amino acid sequence of RQIAKAYARIGNSYFKEEKYK (SEQ ID NO: 43).

4. The chimeric peptide of claim 1, wherein said cell penetrating peptide is an antennapedia homeobox sequence (Antp) having the amino acid sequence of RQIKIWFQNRRMKWKK (SEQ ID NO: 5) or a variant thereof, said variant antennapedia homeobox sequence having the amino acid sequence of $Y_1Y_2Y_3Y_4Y_5Y_6Y_7Y_8Y_9Y_{10}Y_{11}Y_{12}Y_{13}Y_{14}Y_{15}Y_{16}$ (SEQ ID NO: 8), wherein:
$Y_1$ is R or K;
$Y_2$ is Q or N;
$Y_3$ is I or L;
$Y_4$ is K or R;
$Y_5$ is I or L;
$Y_6$ is W or Y;
$Y_7$ is F or Y;
$Y_8$ is Q or N;
$Y_9$ is N or Q;
$Y_{10}$ is R or K;
$Y_{11}$ is R or K;
$Y_{12}$ is M or C;
$Y_{13}$ is K or R;
$Y_{14}$ is W or Y;
$Y_{15}$ is K or R; and
$Y_{16}$ is K or R.

5. The chimeric peptide of claim 1, wherein said cell penetrating peptide is a TAT sequence having the amino acid sequence of YGRKKRRQRRR (SEQ ID NO: 6).

6. The chimeric peptide of claim 1, wherein said cell penetrating peptide is an Arg sequence having the amino acid sequence of RRRRRRRRRRR (SEQ ID NO: 7).

7. The chimeric peptide of claim 1, wherein said chimeric peptide comprises an amino acid sequence selected from the group consisting of:

| | |
|---|---|
| RQIKIWFQNRRMKWKKKAYARIGNSYFK, | (SEQ ID No. 9) |
| RQIKIWFQNRRMKWKKRAYARIGNSYFK, | (SEQ ID No. 10) |
| RQIKIWFQNRRMKWKKAAYARIGNSYFK, | (SEQ ID No. 11) |
| RQIKIWFQNRRMKWKKKGYARIGNSYFK, | (SEQ ID No. 12) |
| RQIKIWFQNRRMKWKKKALARIGNSYFK, | (SEQ ID No. 13) |
| RQIKIWFQNRRMKWKKKAYGRIGNSYFK, | (SEQ ID No. 14) |
| RQIKIWFQNRRMKWKKKAYAKIGNSYFK, | (SEQ ID No. 15) |
| RQIKIWFQNRRMKWKKKAYARRGNSYFK, | (SEQ ID No. 16) |
| RQIKIWFQNRRMKWKKKAYARIGNSYFK, | (SEQ ID No. 17) |
| RQIKIWFQNRRMKWKKKAYARIGQSYFK, | (SEQ ID No. 18) |
| RQIKIWFQNRRMKWKKKAYARIGNYYFK, | (SEQ ID No. 19) |
| RQIKIWFQNRRMKWKKKAYARIGNSSFK, | (SEQ ID No. 20) |
| RQIKIWFQNRRMKWKKKAYARIGNSYYK, | (SEQ ID No. 21) |
| RQIKIWFQNRRMKWKKKAYARIGNSYFR, | (SEQ ID No. 22) |
| KQIKIWFQNRRMKWKKKAYARIGNSYFK, | (SEQ ID No. 23) |
| RNIKIWFQNRRMKWKKKAYARIGNSYFK, | (SEQ ID No. 24) |
| RQLKIWFQNRRMKWKKKAYARIGNSYFK, | (SEQ ID No. 25) |
| RQIRIWFQNRRMKWKKKAYARIGNSYFK, | (SEQ ID No. 26) |
| RQIKLWFQNRRMKWKKKAYARIGNSYFK, | (SEQ ID No. 27) |
| RQIKIYFQNRRMKWKKKAYARIGNSYFK, | (SEQ ID No. 28) |
| RQIKIWYQNRRMKWKKKAYARIGNSYFK, | (SEQ ID No. 29) |
| RQIKIWFNNRRMKWKKKAYARIGNSYFK, | (SEQ ID No. 30) |
| RQIKIWFQQRRMKWKKKAYARIGNSYFK, | (SEQ ID No. 31) |
| RQIKIWFQNKRMKWKKKAYARIGNSYFK, | (SEQ ID No. 32) |
| RQIKIWFQNRKMKWKKKAYARIGNSYFK, | (SEQ ID No. 33) |
| RQIKIWFQNRRCKWKKKAYARIGNSYFK, | (SEQ ID No. 34) |
| RQIKIWFQNRRMRWKKKAYARIGNSYFK, | (SEQ ID No. 35) |
| RQIKIWFQNRRMKYKKKAYARIGNSYFK, | (SEQ ID No. 36) |
| RQIKIWFQNRRMKWRKKAYARIGNSYFK, | (SEQ ID No. 37) |
| RQIKIWFQNRRMKWKRKAYARIGNSYFK, | (SEQ ID No. 38) |
| RQIKIWFQNRRMKWKKRQIAKAYARIGNSYFK, | (SEQ ID No. 39) |
| or | |
| RRRRRRRRRRRKAYARIGNSYFK. | (SEQ ID No. 40) |

8. A composition comprising the chimeric peptide of claim 1 and a pharmaceutically acceptable carrier.

9. A method for treating cancer, said method comprising administering the chimeric peptide according to claim 1 to a subject in need thereof.

10. The method according to claim 9, wherein the cancer includes solid cancers and blood cancers.

11. The method according to claim 9, wherein the cancer is a solid cancer.

12. The method according to claim 9, wherein the cancer is a blood cancer.

* * * * *